United States Patent [19]
Story et al.

[11] Patent Number: 6,024,952
[45] Date of Patent: Feb. 15, 2000

| [54] | ANIONIC/CATIONIC MOISTURIZING COMPLEX |
|---|---|
| [75] | Inventors: David C. Story; Robert E. Gott, both of Cincinnati; M. Tobias Asbury, Milford; Kevin Phifer; F. Anthony Simion, both of Cincinnati, all of Ohio |
| [73] | Assignee: The Andrew Jergens Company, Cincinnati, Ohio |
| [21] | Appl. No.: 08/928,726 |
| [22] | Filed: Sep. 12, 1997 |
| [51] | Int. Cl.[7] .................... A61K 7/48; A61K 7/00 |
| [52] | U.S. Cl. ............. 424/78.03; 514/846; 514/897; 424/70.17 |
| [58] | Field of Search ............... 514/846, 897; 424/70.1, 70.11, 70.17, 70.28, 70.39, 78.03 |

[56] References Cited

U.S. PATENT DOCUMENTS

| 4,663,158 | 5/1987 | Wolfram | 424/70 |
| 4,668,508 | 5/1987 | Grollier | 424/70 |
| 4,719,104 | 1/1988 | Patel | 424/70 |
| 5,417,965 | 5/1995 | Janchitraponvej et al. | 424/70.12 |

*Primary Examiner*—Sally Gardner-Lane
*Attorney, Agent, or Firm*—Oblon, Spivak, McClelland, Maier & Neustadt, P.C.

[57] ABSTRACT

A personal hand or body washing formulation includes a cationic polymer and an anionic emollient which apparently combine to give a sparingly soluble complex, which is deposited on the skin and is difficult to remove. The deposition results in improved skin feel, including skin softness, skin moisture, skin hydration and skin smoothness. Skin appearance is approved as well. Exemplary cationic polymers include polyquaternium 6, while a preferred anionic emollient is sulfated castor oil. The complex also finds use as the conditioning agent of a cleansing and conditioning shampoo.

10 Claims, 144 Drawing Sheets

SENSORY EVALUATION OF COMPLEX VERSUS COMPONENTS
28-JUL-97
CONTRASTING HANDWASH FORMULAS: ONE WITH 2% POLYQUATERNIUM 6 ONLY, ONE WITH 2% POLYQUATERNIUM 6 AND 4% SULFATED CASTOR OIL
POLYQUAT. 6 PLUS SCO, N=10
POLYQUAT. 6 ONLY, N=10

Average Scores

| Attribute | Product | Baseline | 5 min | 10 min | 20 min |
|---|---|---|---|---|---|
| Moisturize | polyquat. 6 plus SCO | 3.45 | 4.2 | 4.2 | 3.9 |
| | polyquat. 6 only | 3.3 | 3.2 | 2.95 | 2.85 |

SENSORY EVALUATION OF COMPLEX VERSUS COMPONENTS
28-JUL-97

CONTRASTING HANDWASH FORMULAS: ONE WITH 2% POLYQUATERNIUM 6 ONLY, ONE WITH 2% POLYQUATERNIUM 6 AND 4% SULFATED CASTOR OIL

POLYQUAT. 6 PLUS SCO, N=10
POLYQUAT. 6 ONLY, N=10

Average Scores

| Attribute | Product | Baseline | 5 min | 10 min | 20 min |
|---|---|---|---|---|---|
| Moisturize | polyquat. 6 plus SCO | 3.45 | 4.2 | 4.2 | 3.9 |
| | polyquat. 6 only | 3.3 | 3.2 | 2.95 | 2.85 |

SENSORY EVALUATION OF COMPLEX VERSUS COMPONENTS
28-JUL-97

CONTRASTING HANDWASH FORMULAS: ONE WITH 2% POLYQUATERNIUM 6 ONLY, ONE WITH 2% POLYQUATERNIUM 6 AND 4% SULFATED CASTOR OIL

POLYQUAT. 6 PLUS SCO, N=10
POLYQUAT. 6 ONLY, N=10

Average Scores

| Attribute | Product | Baseline | 5 min | 10 min | 20 min |
|---|---|---|---|---|---|
| Plump / Hy | polyquat. 6 plus SCO | 3.1 | 3.7 | 3.9 | 3.55 |
| | polyquat. 6 only | 2.95 | 2.9 | 2.65 | 2.65 |

SENSORY EVALUATION OF COMPLEX VERSUS COMPONENTS
 28-JUL-97

CONTRASTING HANDWASH FORMULAS: ONE WITH 2% POLYQUATERNIUM 6 ONLY, ONE WITH
2% POLYQUATERNIUM 6 AND 4% SULFATED CASTOR OIL

POLYQUAT. 6 PLUS SCO, N=10
POLYQUAT. 6 ONLY, N=10
Average Scores

| Attribute | Product | Baseline | 5 min | 10 min | 20 min |
|---|---|---|---|---|---|
| Smooth | polyquat. 6 plus SCO | 3.2 | 2.4 | 2.45 | 2.45 |
|  | polyquat. 6 only | 3 | 3.1 | 3.1 | 2.9 |

SENSORY EVALUATION OF COMPLEX VERSUS COMPONENTS
28-JUL-97

CONTRASTING HANDWASH FORMULAS: ONE WITH 2% POLYQUATERNIUM 6 ONLY, ONE WITH 2% POLYQUATERNIUM 6 AND 4% SULFATED CASTOR OIL

POLYQUAT. 6 PLUS SCO, N=10
POLYQUAT. 6 ONLY, N=10

Average Scores

| Attribute | Product | Baseline | 5 min | 10 min | 20 min |
|---|---|---|---|---|---|
| Soft | polyquat. 6 plus SCO | 3.8 | 3.75 | 3.85 | 3.2 |
| | polyquat. 6 only | 3.6 | 3.2 | 3.05 | 2.75 |

SENSORY EVALUATION OF COMPLEX VERSUS COMPONENTS
28-JUL-97

Average Scores

| Attribute | Product | Baseline | 5 min | 10 min | 20 min |
|---|---|---|---|---|---|
| Tight | polyquat. 6 plus SCO | 0.7 | 1.2 | 1.2 | 1.6 |
| | polyquat. 6 only | 0.75 | 1.1 | 1.35 | 1.3 |

SENSORY EVALUATION OF COMPLEX VERSUS COMPONENTS
28-JUL-97

Average Scores

| Attribute | Product | Baseline | 5 min | 10 min | 20 min |
|---|---|---|---|---|---|
| Residue/C | polyquat. 6 plus SCO | 0.7 | 3.9 | 4 | 4.1 |
| | polyquat. 6 only | 0.7 | 1.5 | 1.1 | 1.2 |

SENSORY EVALUATION OF COMPLEX VERSUS COMPONENTS
28-JUL-97

Average Scores

| Attribute | Product | Baseline | 5 min | 10 min | 20 min |
|---|---|---|---|---|---|
| Looks Dry | polyquat. 6 plus SCO | 0.8 | 0.5 | 0.5 | 0.5 |
| | polyquat. 6 only | 0.9 | 0.45 | 0.65 | 0.65 |

SENSORY EVALUATION OF COMPLEX VERSUS COMPONENTS
28-JUL-97

Average Scores

| Attribute | Product | Baseline | 5 min | 10 min | 20 min |
|---|---|---|---|---|---|
| Feels Dry | polyquat. 6 plus SCO | 0.6 | 0.95 | 0.95 | 0.85 |
| | polyquat. 6 only | 0.65 | 0.9 | 0.95 | 0.85 |

SENSORY EVALUATION OF COMPLEX VERSUS COMPONENTS
28-JUL-97

Change from Baseline

| Attribute | Product | Baseline | 5 min | 10 min | 20 min |
|---|---|---|---|---|---|
| Moisturized | polyquat. 6 plus SCO | 0 | 0.75 | 0.75 | 0.45 |
|  | polyquat. 6 only | 0 | -0.1 | -0.35 | -0.45 |

SENSORY EVALUATION OF COMPLEX VERSUS COMPONENTS
28-JUL-97

Change from Baseline

| Attribute | Product | Baseline | 5 min | 10 min | 20 min |
|---|---|---|---|---|---|
| Plump / Hy | polyquat. 6 plus SCO | 0 | 0.6 | 0.8 | 0.45 |
| | polyquat. 6 only | 0 | -0.05 | -0.3 | -0.3 |

SENSORY EVALUATION OF COMPLEX VERSUS COMPONENTS
28-JUL-97

Change from Baseline

| Attribute | Product | Baseline | 5 min | 10 min | 20 min |
|---|---|---|---|---|---|
| Smooth | polyquat. 6 plus SCO | 0 | -0.8 | -0.75 | -0.75 |
| | polyquat. 6 only | 0 | 0.1 | 0.1 | -0.1 |

SENSORY EVALUATION OF COMPLEX VERSUS COMPONENTS
28-JUL-97

Change from Baseline

| Attribute | Product | Baseline | 5 min | 10 min | 20 min |
|---|---|---|---|---|---|
| Soft | polyquat. 6 plus SCO | 0 | -0.05 | 0.05 | -0.6 |
| | polyquat. 6 only | 0 | -0.4 | -0.55 | -0.85 |

SENSORY EVALUATION OF COMPLEX VERSUS COMPONENTS
28-JUL-97

Change from Baseline

| Attribute | Product | Baseline | 5 min | 10 min | 20 min |
|---|---|---|---|---|---|
| Tight | polyquat. 6 plus SCO | 0 | 0.5 | 0.5 | 0.9 |
| | polyquat. 6 only | 0 | 0.35 | 0.6 | 0.55 |

SENSORY EVALUATION OF COMPLEX VERSUS COMPONENTS
28-JUL-97

Change from Baseline

| Attribute | Product | Baseline | 5 min | 10 min | 20 min |
|---|---|---|---|---|---|
| Residue/C | polyquat. 6 plus SCO | 0 | 3.2 | 3.3 | 3.4 |
|  | polyquat. 6 only | 0 | 0.8 | 0.4 | 0.5 |

SENSORY EVALUATION OF COMPLEX VERSUS COMPONENTS
28-JUL-97

Change from Baseline

| Attribute | Product | Baseline | 5 min | 10 min | 20 min |
|---|---|---|---|---|---|
| Looks Dry | polyquat. 6 plus SCO | 0 | -0.3 | -0.3 | -0.3 |
|  | polyquat. 6 only | 0 | -0.45 | -0.25 | -0.25 |

SENSORY EVALUATION OF COMPLEX VERSUS COMPONENTS
28-JUL-97

Change from Baseline

| Attribute | Product | Baseline | 5 min | 10 min | 20 min |
|---|---|---|---|---|---|
| Feels Dry | polyquat. 6 plus SCO | 0 | 0.35 | 0.35 | 0.25 |
| | polyquat. 6 only | 0 | 0.25 | 0.3 | 0.2 |

SENSORY EVALUATION OF COMPLEX RATIOS
29-JUL-97

CONTRASTING HANDWASH FORMULAS: ONE WITH 2% POLYQUAT 6 AND 4% SULFATED CASOR OIL ONE WITH 2% POLYQUATERNIUM 6 AND 2% SULFATED CASTOR OIL

2% POLYQUAT 6 AND 4% SULFATED CASTOR OIL, N=10
2% POLYQUAT 6 AND 2% SULFATED CASTOR OIL, N=10

Average Scores

| Attribute | Product | Baseline | 5 min | 10 min | 20 min |
|---|---|---|---|---|---|
| Moisturize | 2% polquat. 6, 4% SCO | 3.4 | 4.5 | 4.4 | 4.1 |
| | 2% polquat. 6, 2% SCO | 3.4 | 4.4 | 4.4 | 4 |

SENSORY EVALUATION OF COMPLEX RATIOS
29-JUL-97

CONTRASTING HANDWASH FORMULAS: ONE WITH 2% POLYQUAT 6 AND 4% SULFATED CASOR OIL ONE WITH 2% POLYQUATERNIUM 6 AND 2% SULFATED CASTOR OIL

2% POLYQUAT 6 AND 4% SULFATED CASTOR OIL, N=10
2% POLYQUAT 6 AND 2% SULFATED CASTOR OIL, N=10

Average Scores

| Attribute | Product | Baseline | 5 min | 10 min | 20 min |
|---|---|---|---|---|---|
| Plump / Hy | 2% polquat. 6, 4% SCO | 3.1 | 4.4 | 4.3 | 4 |
|  | 2% polquat. 6, 2% SCO | 3.15 | 4.3 | 4.3 | 3.9 |

SENSORY EVALUATION OF COMPLEX RATIOS
29-JUL-97

CONTRASTING HANDWASH FORMULAS: ONE WITH 2% POLYQUAT 6 AND 4% SULFATED CASOR OIL ONE WITH 2% POLYQUATERNIUM 6 AND 2% SULFATED CASTOR OIL

2% POLYQUAT 6 AND 4% SULFATED CASTOR OIL, N=10
2% POLYQUAT 6 AND 2% SULFATED CASTOR OIL, N=10

Average Scores

| Attribute | Product | Baseline | 5 min | 10 min | 20 min |
|---|---|---|---|---|---|
| Smooth | 2% polquat. 6, 4% SCO | 3.9 | 2.6 | 3.1 | 3.05 |
|  | 2% polyquat. 6, 2% SCO | 3.8 | 3.75 | 4.1 | 4 |

SENSORY EVALUATION OF COMPLEX RATIOS
29-JUL-97

CONTRASTING HANDWASH FORMULAS: ONE WITH 2% POLYQUAT 6 AND 4% SULFATED CASOR OIL ONE WITH 2% POLYQUATERNIUM 6 AND 2% SULFATED CASTOR OIL

2% POLYQUAT 6 AND 4% SULFATED CASTOR OIL, N=10
2% POLYQUAT 6 AND 2% SULFATED CASTOR OIL, N=10

Average Scores

| Attribute | Product | Baseline | 5 min | 10 min | 20 min |
|---|---|---|---|---|---|
| Soft | 2% polquat. 6, 4% SCO | 3.4 | 4.1 | 4 | 4 |
|  | 2% polyquat. 6, 2% SCO | 3.4 | 4 | 4 | 3.9 |

SENSORY EVALUATION OF COMPLEX RATIOS
29-JUL-97

Average Scores

| Attribute | Product | Baseline | 5 min | 10 min | 20 min |
|---|---|---|---|---|---|
| Tight | 2% polquat. 6, 4% SCO | 1.6 | 1.7 | 1.6 | 1.4 |
| | 2% polyquat. 6, 2% SCO | 1.6 | 1.75 | 1.85 | 1.4 |

SENSORY EVALUATION OF COMPLEX RATIOS
29-JUL-97

Average Scores

| Attribute | Product | Baseline | 5 min | 10 min | 20 min |
|---|---|---|---|---|---|
| Residue/C | 2% polquat. 6, 4% SCO | 0.85 | 4.15 | 4.05 | 3.85 |
|  | 2% polyquat. 6, 2% SCO | 0.9 | 3.05 | 2.9 | 2.6 |

SENSORY EVALUATION OF COMPLEX RATIOS
29-JUL-97

Average Scores

| Attribute | Product | Baseline | 5 min | 10 min | 20 min |
|---|---|---|---|---|---|
| Looks Dry | 2% polquat. 6, 4% SCO | 1.45 | 1.25 | 1.35 | 1.25 |
| | 2% polyquat. 6, 2% SCO | 1.4 | 1.15 | 1.25 | 1.15 |

SENSORY EVALUATION OF COMPLEX RATIOS
29-JUL-97

Average Scores

| Attribute | Product | Baseline | 5 min | 10 min | 20 min |
|---|---|---|---|---|---|
| Feels Dry | 2% polquat. 6, 4% SCO | 1.45 | 1.1 | 1.15 | 1.3 |
| | 2% polyquat. 6, 2% SCO | 1.4 | 1.2 | 1.25 | 1.4 |

SENSORY EVALUATION OF COMPLEX RATIOS
29-JUL-97

Change from Baseline

| Attribute | Product | Baseline | 5 min | 10 min | 20 min |
|---|---|---|---|---|---|
| Moisturize | 2% polquat. 6, 4% SCO | 0 | 1.1 | 1 | 0.7 |
| | 2% polyquat. 6, 2% SCO | 0 | 1 | 1 | 0.6 |

SENSORY EVALUATION OF COMPLEX RATIOS
29-JUL-97

Change from Baseline

| Attribute | Product | Baseline | 5 min | 10 min | 20 min |
|---|---|---|---|---|---|
| Plump / Hy | 2% polquat. 6, 4% SCO | 0 | 1.3 | 1.2 | 0.9 |
| | 2% polyquat. 6, 2% SCO | 0 | 1.15 | 1.15 | 0.75 |

SENSORY EVALUATION OF COMPLEX RATIOS
29-JUL-97

Change from Baseline

| Attribute | Product | Baseline | 5 min | 10 min | 20 min |
|---|---|---|---|---|---|
| Smooth | 2% polquat. 6, 4% SCO | 0 | -1.3 | -0.8 | -0.85 |
| | 2% polyquat. 6, 2% SCO | 0 | -0.05 | 0.3 | 0.2 |

SENSORY EVALUATION OF COMPLEX RATIOS
29-JUL-97

Change from Baseline

| Attribute | Product | Baseline | 5 min | 10 min | 20 min |
|---|---|---|---|---|---|
| Soft | 2% polquat. 6, 4% SCO | 0 | 0.7 | 0.6 | 0.6 |
|  | 2% polyquat. 6, 2% SCO | 0 | 0.6 | 0.6 | 0.5 |

SENSORY EVALUATION OF COMPLEX RATIOS
29-JUL-97

Change from Baseline

| Attribute | Product | Baseline | 5 min | 10 min | 20 min |
|---|---|---|---|---|---|
| Tight | 2% polquat. 6, 4% SCO | 0 | 0.1 | 0 | -0.2 |
|  | 2% polyquat. 6, 2% SCO | 0 | 0.15 | 0.25 | -0.2 |

SENSORY EVALUATION OF COMPLEX RATIOS
29-JUL-97

Change from Baseline

| Attribute | Product | Baseline | 5 min | 10 min | 20 min |
|---|---|---|---|---|---|
| Residue/C | 2% polquat. 6, 4% SCO | 0 | 3.3 | 3.2 | 3 |
| | 2% polyquat. 6, 2% SCO | 0 | 2.15 | 2 | 1.7 |

SENSORY EVALUATION OF COMPLEX RATIOS
29-JUL-97

Change from Baseline

| Attribute | Product | Baseline | 5 min | 10 min | 20 min |
|---|---|---|---|---|---|
| Looks Dry | 2% polquat. 6, 4% SCO | 0 | -0.2 | -0.1 | -0.2 |
| | 2% polyquat. 6, 2% SCO | 0 | -0.25 | -0.15 | -0.25 |

SENSORY EVALUATION OF COMPLEX RATIOS
29-JUL-97

Change from Baseline

| Attribute | Product | Baseline | 5 min | 10 min | 20 min |
|---|---|---|---|---|---|
| Feels Dry | 2% polquat. 6, 4% SCO | 0 | -0.35 | -0.3 | -0.15 |
|  | 2% polyquat. 6, 2% SCO | 0 | -0.2 | -0.15 | 0 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Average Scores

| Attribute | Product | Baseline | 5 min | 10 min | 20 min |
|---|---|---|---|---|---|
| Moisturize | 2% polquat. 6, 4% SCO | 2.7 | 3.8 | 3.8 | 3.25 |
| | 2% polyquat. 6, 1% SCO | 2.7 | 3.05 | 3 | 2.8 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Average Scores

| Attribute | Product | Baseline | 5 min | 10 min | 20 min |
|---|---|---|---|---|---|
| Plump / Hy | 2% polquat. 6, 4% SCO | 2.75 | 3.8 | 3.75 | 3.2 |
|  | 2% polyquat. 6, 1% SCO | 2.65 | 2.9 | 2.9 | 2.65 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Average Scores

| Attribute | Product | Baseline | 5 min | 10 min | 20 min |
|---|---|---|---|---|---|
| Smooth | 2% polquat. 6, 4% SCO | 3.6 | 2.75 | 3.1 | 2.9 |
|  | 2% polyquat. 6, 1% SCO | 3.5 | 3.05 | 3.2 | 3.05 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Average Scores

| Attribute | Product | Baseline | 5 min | 10 min | 20 min |
|---|---|---|---|---|---|
| Soft | 2% polquat. 6, 4% SCO | 3.3 | 3.55 | 3.5 | 3.55 |
| | 2% polyquat. 6, 1% SCO | 3.3 | 3.3 | 3.3 | 3.45 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Average Scores

| Attribute | Product | Baseline | 5 min | 10 min | 20 min |
|---|---|---|---|---|---|
| Tight | 2% polquat. 6, 4% SCO | 0.65 | 0.9 | 0.9 | 1.05 |
| | 2% polyquat. 6, 1% SCO | 0.65 | 0.85 | 1.2 | 1.05 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Average Scores

| Attribute | Product | Baseline | 5 min | 10 min | 20 min |
|---|---|---|---|---|---|
| Residue/C | 2% polquat. 6, 4% SCO | 0.3 | 3.35 | 3.15 | 3.05 |
|  | 2% polyquat. 6, 1% SCO | 0.2 | 1.15 | 1 | 1.05 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Average Scores

| Attribute | Product | Baseline | 5 min | 10 min | 20 min |
|---|---|---|---|---|---|
| Looks Dry | 2% polquat. 6, 4% SCO | 0.3 | 0.25 | 0.25 | 0.25 |
| | 2% polyquat. 6, 1% SCO | 0.35 | 0.3 | 0.4 | 0.3 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Average Scores

| Attribute | Product | Baseline | 5 min | 10 min | 20 min |
|---|---|---|---|---|---|
| Feels Dry | 2% polquat. 6, 4% SCO | 0.3 | 0.45 | 0.55 | 0.55 |
| | 2% polyquat. 6, 1% SCO | 0.35 | 1.15 | 0.8 | 0.55 |

SENSORY EVALUATION OF COMPLEX VERSUS COMPONENTS
28-JUL-97
CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Change from Baseline

| Attribute | Product | Baseline | 5 min | 10 min | 20 min |
|---|---|---|---|---|---|
| Moisturize | 2% polquat. 6, 4% SCO | 0 | 1.1 | 1.1 | 0.55 |
| | 2% polyquat. 6, 1% SCO | 0 | 0.35 | 0.3 | 0.1 |

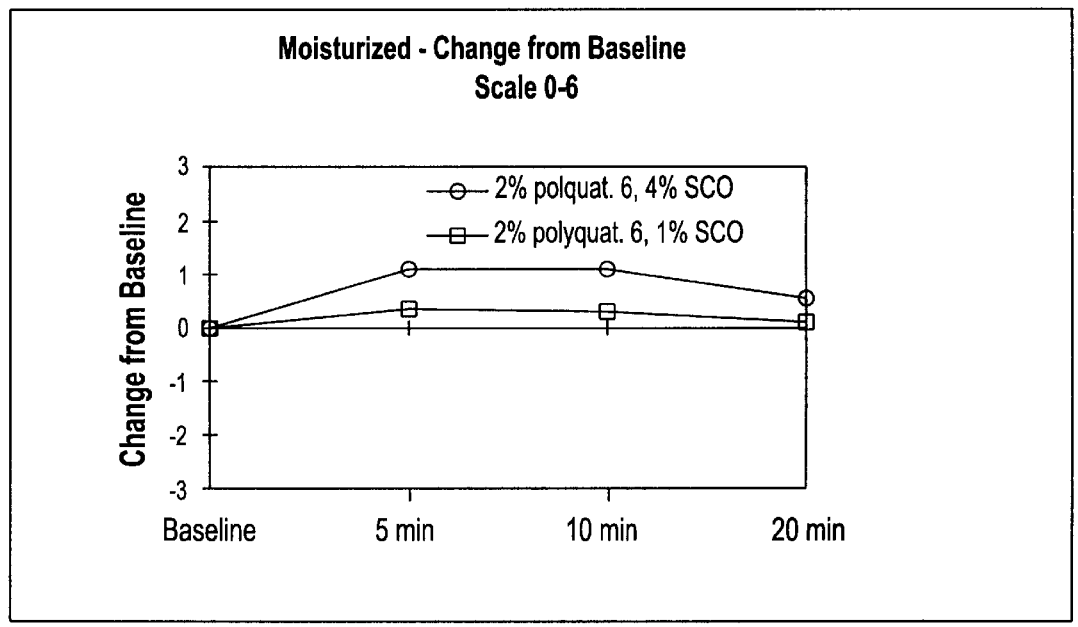

FIG.31

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Change from Baseline

| Attribute | Product | Baseline | 5 min | 10 min | 20 min |
|---|---|---|---|---|---|
| Plump / Hy | 2% polquat. 6, 4% SCO | 0 | 1.05 | 1 | 0.45 |
| | 2% polyquat. 6, 1% SCO | 0 | 0.25 | 0.25 | 0 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Change from Baseline

| Attribute | Product | Baseline | 5 min | 10 min | 20 min |
|---|---|---|---|---|---|
| Smooth | 2% polquat. 6, 4% SCO | 0 | -0.85 | -0.5 | -0.7 |
|  | 2% polyquat. 6, 1% SCO | 0 | -0.45 | -0.3 | -0.45 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Change from Baseline

| Attribute | Product | Baseline | 5 min | 10 min | 20 min |
|---|---|---|---|---|---|
| Soft | 2% polquat. 6, 4% SCO | 0 | 0.25 | 0.2 | 0.25 |
| | 2% polyquat. 6, 1% SCO | 0 | 0 | 0 | 0.15 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Change from Baseline

| Attribute | Product | Baseline | 5 min | 10 min | 20 min |
|---|---|---|---|---|---|
| Tight | 2% polquat. 6, 4% SCO | 0 | 0.25 | 0.25 | 0.4 |
|  | 2% polyquat. 6, 1% SCO | 0 | 0.2 | 0.55 | 0.4 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Change from Baseline

| Attribute | Product | Baseline | 5 min | 10 min | 20 min |
|---|---|---|---|---|---|
| Residue/C | 2% polquat. 6, 4% SCO | 0 | 3.05 | 2.85 | 2.75 |
|  | 2% polyquat. 6, 1% SCO | 0 | 0.95 | 0.8 | 0.85 |

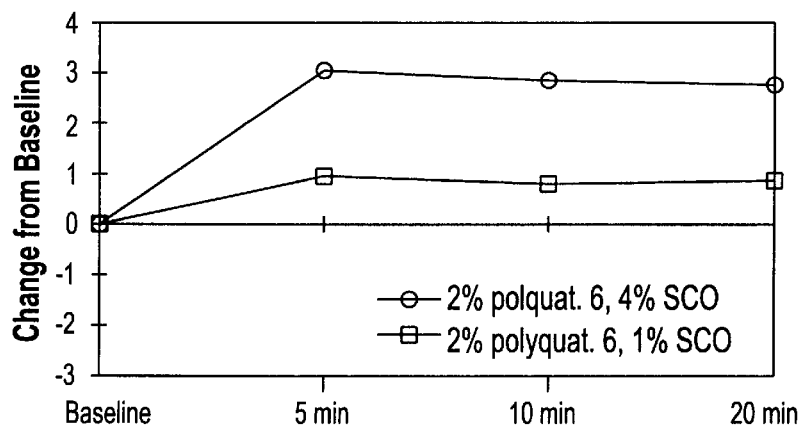

FIG.3N

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Change from Baseline

| Attribute | Product | Baseline | 5 min | 10 min | 20 min |
|---|---|---|---|---|---|
| Looks Dry | 2% polquat. 6, 4% SCO | 0 | -0.05 | -0.05 | -0.05 |
| | 2% polyquat. 6, 1% SCO | 0 | -0.05 | 0.05 | -0.05 |

SENSORY EVALUATION OF COMPLEX VERSUS COMPONENTS
28-JUL-97

CONTRASTING HANDWASH FORMULAS: ONE WITH 2% POLYQUAT 6 AND 4% SULFATED CASOR OIL ONE WITH 2% POLYQUATERNIUM 6 AND 1% SULFATED CASTOR OIL

2% POLYQUAT 6 AND 4% SULFATED CASTOR OIL, N=10
2% POLYQUAT 6 AND 1% SULFATED CASTOR OIL, N=10

Change from Baseline

| Attribute | Product | Baseline | 5 min | 10 min | 20 min |
|---|---|---|---|---|---|
| Feels Dry | 2% polquat. 6, 4% SCO | 0 | 0.15 | 0.25 | 0.25 |
|  | 2% polquat. 6, 1% SCO | 0 | 0.8 | 0.45 | 0.2 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=1
0% POLYQUAT 6 AND 0% SULFATED CASTOR OIL, N=10

Average Scores

| Attribute | Product | Baseline | 5 min | 10 min | 20 min |
|---|---|---|---|---|---|
| Moisturize | 0.5% polquat. 6, 0.5% SCO | 2.35 | 2.95 | 2.7 | 2.55 |
| | 0% polyquat. 6, 0% SCO | 2.4 | 3.3 | 2.9 | 2.75 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=1
0% POLYQUAT 6 AND 0% SULFATED CASTOR OIL, N=10

Average Scores

| Attribute | Product | Baseline | 5 min | 10 min | 20 min |
|---|---|---|---|---|---|
| Plump / Hy | 0.5% polquat. 6, 0.5% SCO | 2.15 | 2.7 | 2.2 | 2.15 |
| | 0% polquat. 6, 0% SCO | 2.2 | 2.95 | 2.4 | 2.35 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=1
0% POLYQUAT 6 AND 0% SULFATED CASTOR OIL, N=10

Average Scores

| Attribute | Product | Baseline | 5 min | 10 min | 20 min |
|---|---|---|---|---|---|
| Smooth | 0.5% polquat. 6, 0.5% SCO | 2.9 | 3.3 | 3.2 | 2.95 |
| | 0% polyquat. 6, 0% SCO | 2.9 | 3.65 | 3.4 | 3.3 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=1
0% POLYQUAT 6 AND 0% SULFATED CASTOR OIL, N=10

Average Scores

| Attribute | Product | Baseline | 5 min | 10 min | 20 min |
|---|---|---|---|---|---|
| Soft | 0.5% polquat. 6, 0.5% SCO | 2.55 | 2.8 | 2.8 | 2.6 |
| | 0% polquat. 6, 0% SCO | 2.55 | 2.95 | 2.8 | 2.65 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Average Scores

| Attribute | Product | Baseline | 5 min | 10 min | 20 min |
|---|---|---|---|---|---|
| Tight | 0.5% polquat. 6, 0.5% SCO | 0.95 | 1.1 | 1.25 | 1.25 |
|  | 0% polquat. 6, 0% SCO | 0.95 | 1.2 | 1.3 | 1.35 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Average Scores

| Attribute | Product | Baseline | 5 min | 10 min | 20 min |
|---|---|---|---|---|---|
| Residue/C | 0.5% polquat. 6, 0.5% SCO | 0.3 | 1.05 | 0.75 | 0.75 |
| | 0% polyquat. 6, 0% SCO | 0.35 | 1 | 0.6 | 0.6 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Average Scores

| Attribute | Product | Baseline | 5 min | 10 min | 20 min |
|---|---|---|---|---|---|
| Looks Dry | 0.5% polquat. 6, 0.5% SCO | 1 | 0.55 | 0.7 | 1.05 |
| | 0% polquat. 6, 0% SCO | 0.95 | 0.7 | 0.95 | 1.25 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Average Scores

| Attribute | Product | Baseline | 5 min | 10 min | 20 min |
|---|---|---|---|---|---|
| Feels Dry | 0.5% polquat. 6, 0.5% SCO | 1.15 | 0.9 | 1.25 | 1.25 |
| | 0% polyquat. 6, 0% SCO | 1.1 | 0.95 | 1.3 | 1.35 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Change from Baseline

| Attribute | Product | Baseline | 5 min | 10 min | 20 min |
|---|---|---|---|---|---|
| Moisturize | 0.5% polquat. 6, 0.5% SCO | 0 | 0.6 | 0.35 | 0.2 |
| | 0% polyquat. 6, 0% SCO | 0 | 0.9 | 0.5 | 0.35 |

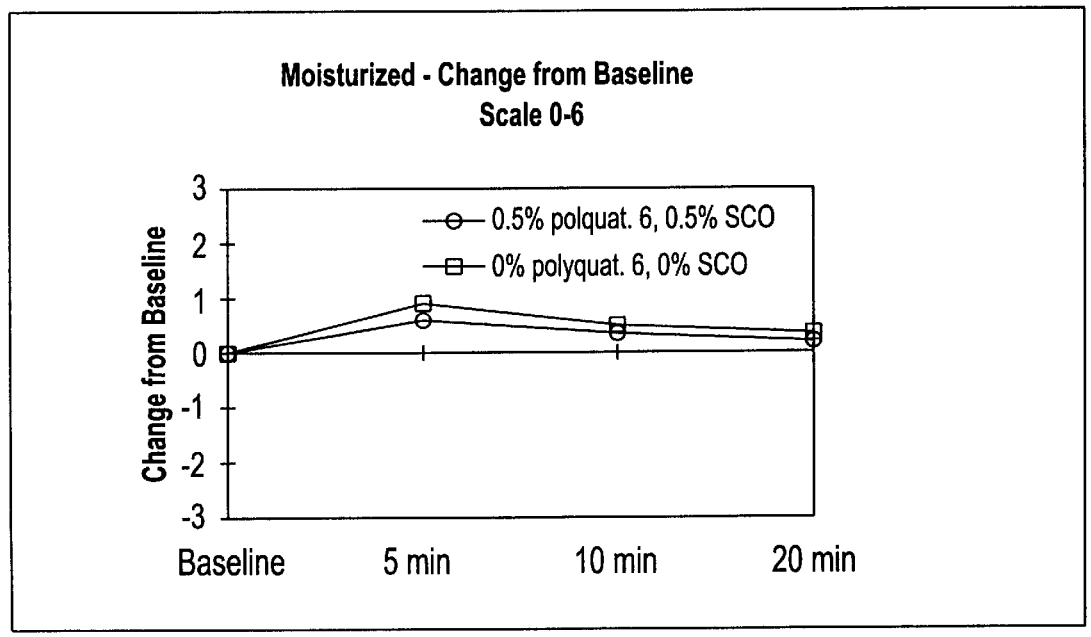

FIG.41

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Change from Baseline

| Attribute | Product | Baseline | 5 min | 10 min | 20 min |
|---|---|---|---|---|---|
| Plump / Hy | 0.5% polquat. 6, 0.5% SCO | 0 | 0.55 | 0.05 | 0 |
| | 0% polquat. 6, 0% SCO | 0 | 0.75 | 0.2 | 0.15 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Change from Baseline

| Attribute | Product | Baseline | 5 min | 10 min | 20 min |
|---|---|---|---|---|---|
| Smooth | 0.5% polquat. 6, 0.5% SCO | 0 | 0.4 | 0.3 | 0.05 |
| | 0% polquat. 6, 0% SCO | 0 | 0.75 | 0.5 | 0.4 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Change from Baseline

| Attribute | Product | Baseline | 5 min | 10 min | 20 min |
|---|---|---|---|---|---|
| Soft | 0.5% polquat. 6, 0.5% SCO | 0 | 0.25 | 0.25 | 0.05 |
|  | 0% polquat. 6, 0% SCO | 0 | 0.4 | 0.25 | 0.1 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Change from Baseline

| Attribute | Product | Baseline | 5 min | 10 min | 20 min |
|---|---|---|---|---|---|
| Tight | 0.5% polquat. 6, 0.5% SCO | 0 | 0.15 | 0.3 | 0.3 |
|  | 0% polyquat. 6, 0% SCO | 0 | 0.25 | 0.35 | 0.4 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Change from Baseline

| Attribute | Product | Baseline | 5 min | 10 min | 20 min |
|---|---|---|---|---|---|
| Residue/C | 0.5% polquat. 6, 0.5% SCO | 0 | 0.75 | 0.45 | 0.45 |
| | 0% polquat. 6, 0% SCO | 0 | 0.65 | 0.25 | 0.25 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Change from Baseline

| Attribute | Product | Baseline | 5 min | 10 min | 20 min |
|---|---|---|---|---|---|
| Looks Dry | 0.5% polquat. 6, 0.5% SCO | 0 | -0.45 | -0.3 | 0.05 |
|  | 0% polyquat. 6, 0% SCO | 0 | -0.25 | 0 | 0.3 |

SENSORY EVALUATION OF COMPLEX (DIFFERING LEVELS)
30-JUL-97

CONTRASTING HANDWASH FORMULAS: ONE WITH 0.5% POLYQUAT 6 AND 0.5% SULFATED CASOR OIL ONE WITH 0% POLYQUATERNIUM 6 AND 0% SULFATED CASTOR OIL 0.5% POLYQUAT 6 AND 0.5% SULFATED CASTOR OIL, N=10
0% POLYQUAT 6 AND 0% SULFATED CASTOR OIL, N=10

Change from Baseline

| Attribute | Product | Baseline | 5 min | 10 min | 20 min |
|---|---|---|---|---|---|
| Feels Dry | 0.5% polquat. 6, 0.5% SCO | 0 | -0.25 | 0.1 | 0.1 |
| | 0% polyquat. 6, 0% SCO | 0 | -0.15 | 0.2 | 0.25 |

SENSORY EVALUATION OF COMPLEX (DIFFERING ANIONICS)
31-JUL-97

CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Moisturize | 2% polquat. 6, 4% anionic silicone | 2.6 | 3.4 | 3.28 | 3.05 |
|  | 0% polquat. 6, 0% anionic silicone | 2.5 | 2.9 | 3.22 | 2.65 |

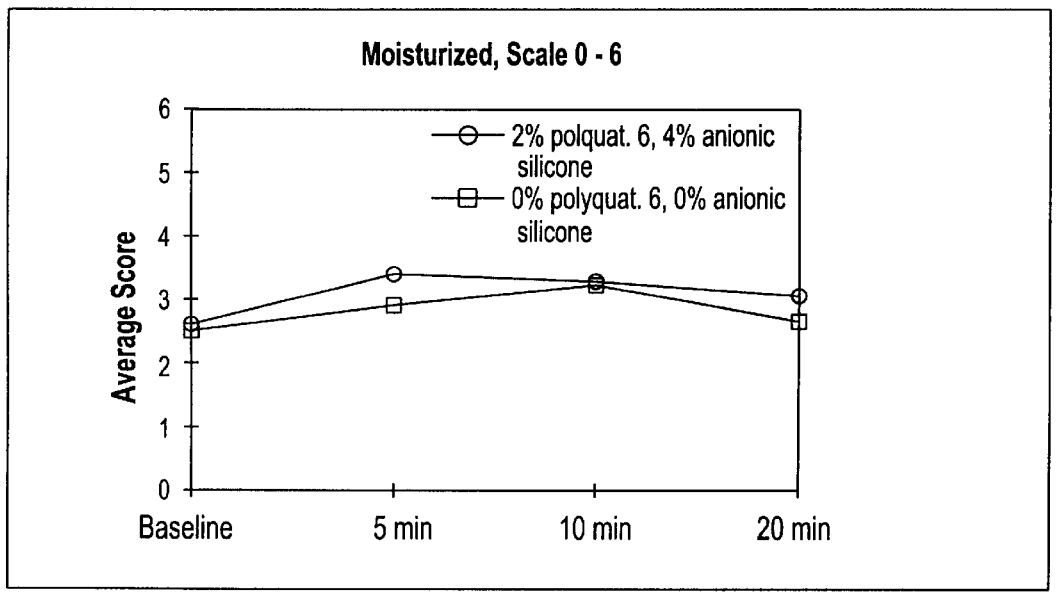

FIG.5A

SENSORY EVALUATION OF COMPLEX (DIFFERING ANIONICS)
31-JUL-97

CONTRASTING HANDWASH FORMULAS: ONE WITH 2% POLYQUAT. 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Plump / Hy | 2% polquat. 6, 4% anionic silicone | 2.5 | 3.35 | 3.22 | 3.1 |
|  | 0% polyquat. 6, 0% anionic silicone | 2.45 | 2.75 | 3.06 | 2.4 |

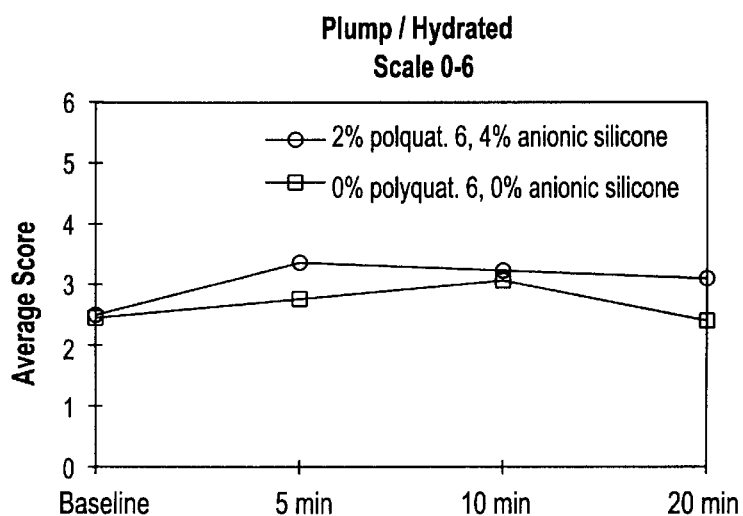

FIG.5B

SENSORY EVALUATION OF COMPLEX (DIFFERING ANIONICS)
31-JUL-97

CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Smooth | 2% polquat. 6, 4% anionic silicone | 3.4 | 3.7 | 3.61 | 3.7 |
|  | 0% polquat. 6, 0% anionic silicone | 3.5 | 3.3 | 3.56 | 3.4 |

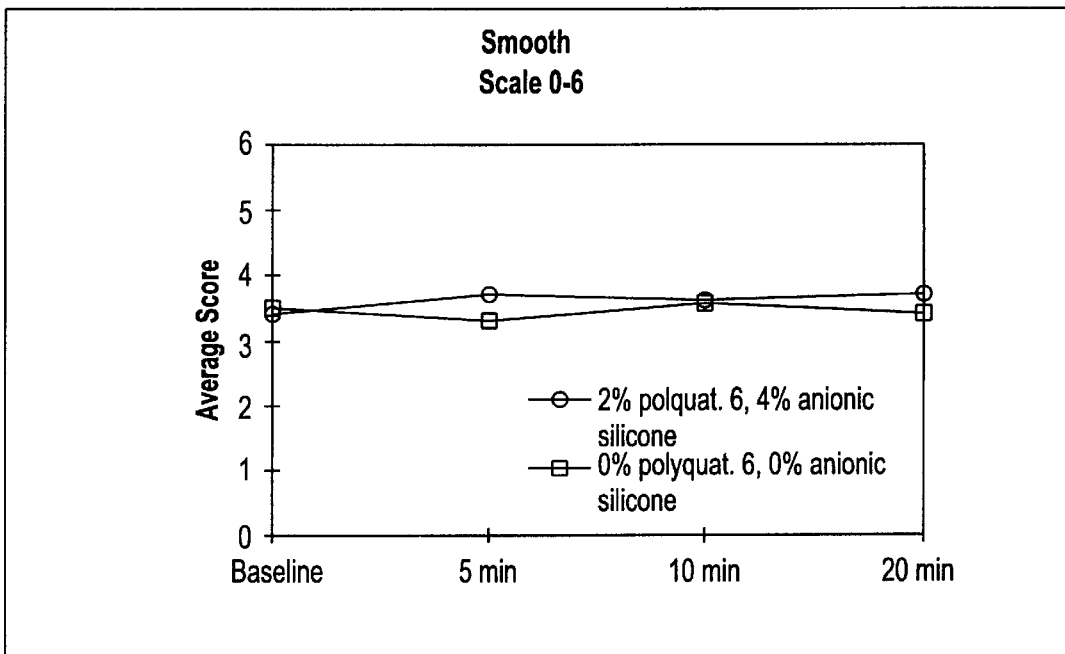

FIG.5C

SENSORY EVALUATION OF COMPLEX (DIFFERING ANIONICS)
  31-JUL-97

CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Soft | 2% polquat. 6, 4% anionic silicone | 2.9 | 3.55 | 3.56 | 3.35 |
|  | 0% polyquat. 6, 0% anionic silicone | 2.9 | 3.25 | 3.11 | 2.8 |

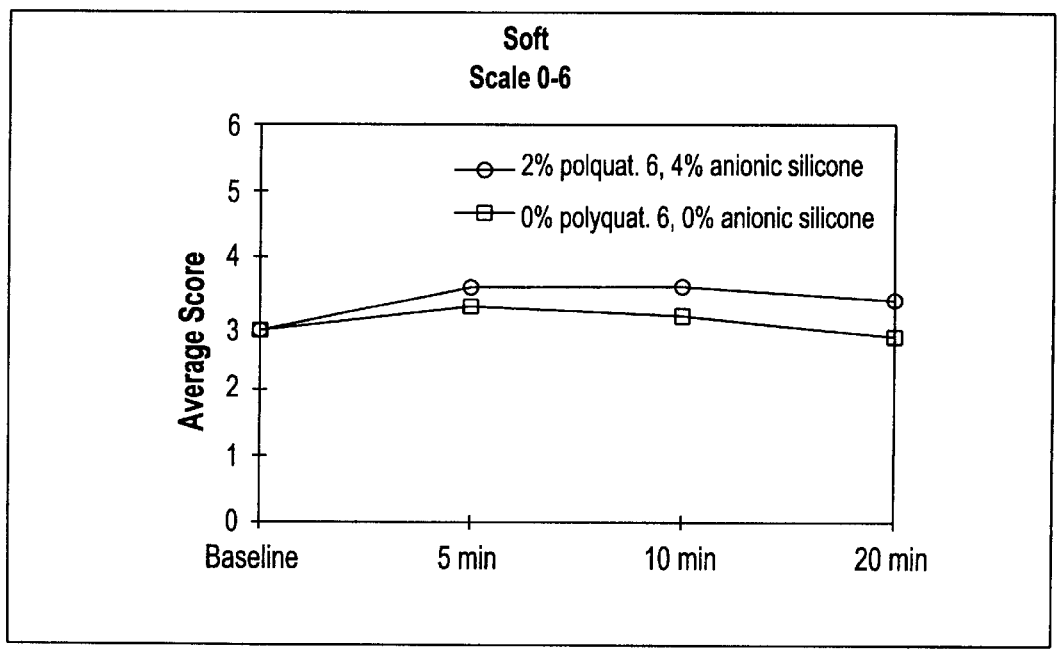

FIG.5D

SENSORY EVALUATION OF COMPLEX (DIFFERING ANIONICS)
31-JUL-97

CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Tight | 2% polquat. 6, 4% anionic silicone | 0.75 | 0.7 | 0.56 | 0.75 |
| | 0% polyquat. 6, 0% anionic silicone | 0.75 | 0.6 | 0.72 | 0.85 |

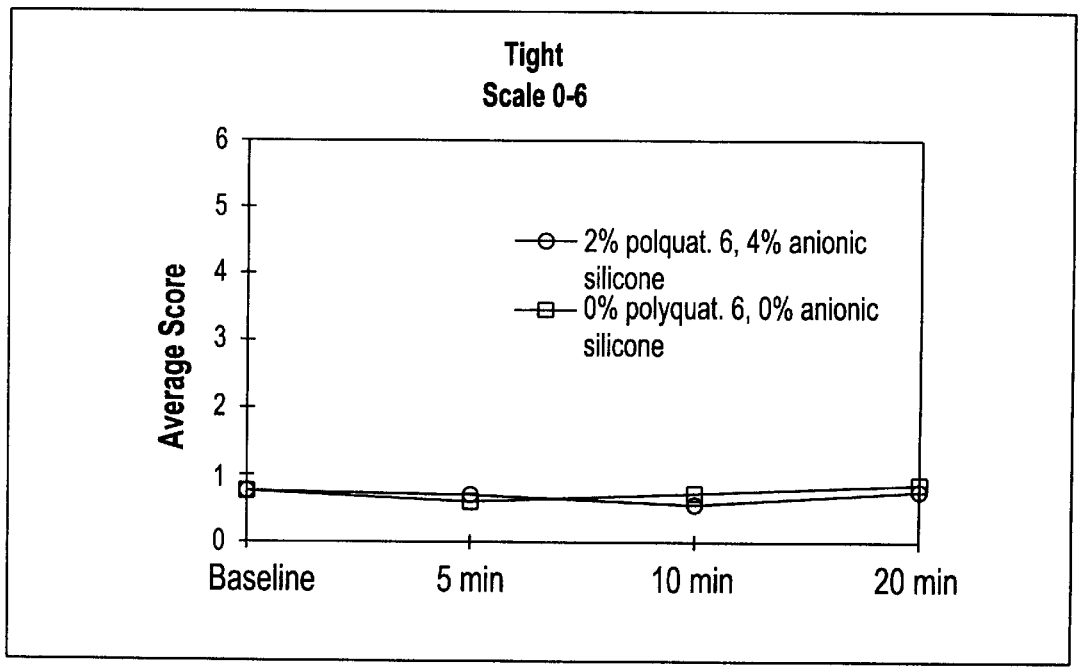

FIG.5E

SENSORY EVALUATION OF COMPLEX (DIFFERING ANIONICS)
31-JUL-97

CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Residue/C | 2% polquat. 6, 4% anionic silicone | 0.9 | 2 | 1.94 | 1.7 |
| | 0% polyquat. 6, 0% anionic silicone | 0.9 | 1.6 | 1.44 | 1.3 |

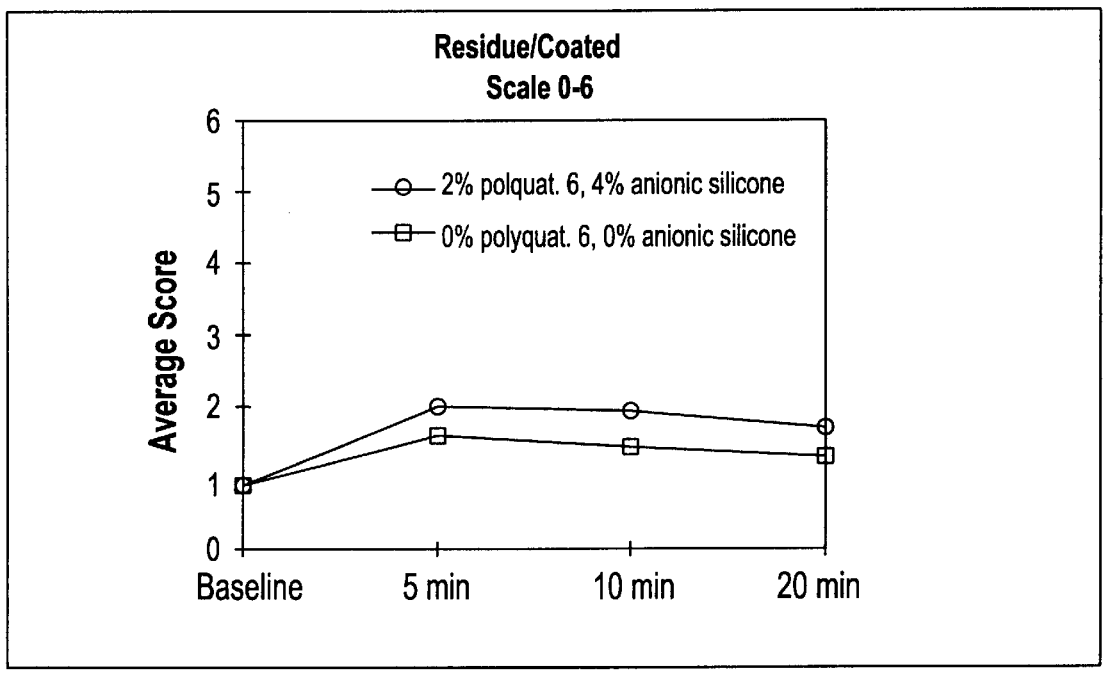

FIG.5F

SENSORY EVALUATION OF COMPLEX (DIFFERING ANIONICS)
31-JUL-97
CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE
2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Looks Dry | 2% polquat. 6, 4% anionic silicone | 1.15 | 0.9 | 1 | 0.9 |
| | 0% polyquat. 6, 0% anionic silicone | 1.2 | 0.9 | 1.17 | 1.2 |

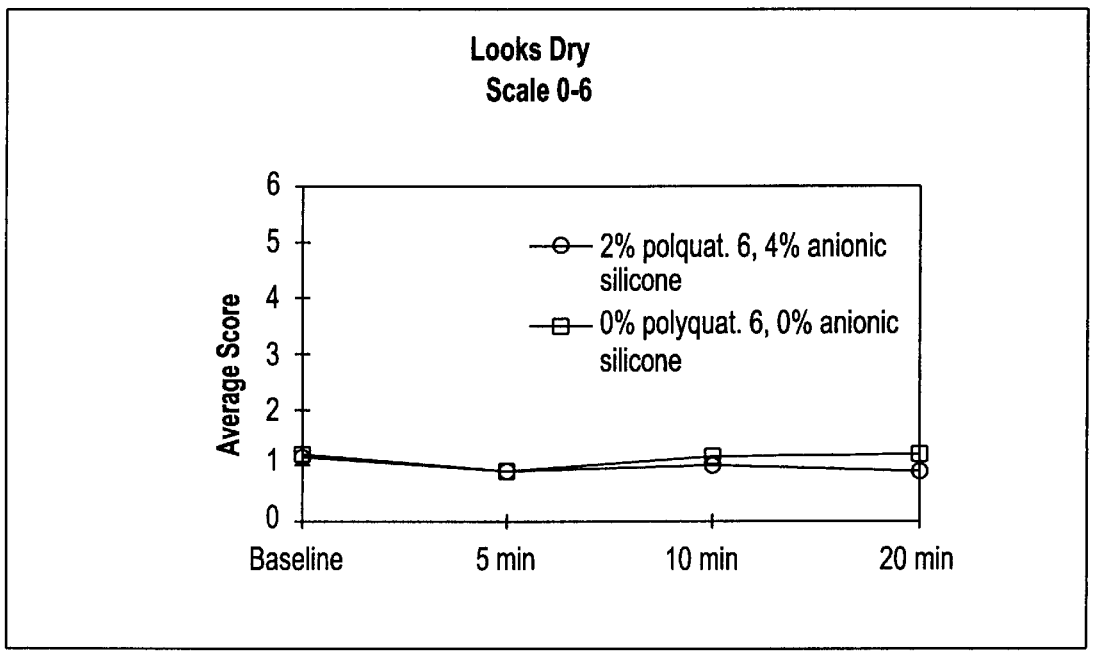

FIG.5G

SENSORY EVALUATION OF COMPLEX (DIFFERING ANIONICS)
31-JUL-97
CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE
2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Feels Dry | 2% polquat. 6, 4% anionic silicone | 1.45 | 0.9 | 0.89 | 0.9 |
| | 0% polyquat. 6, 0% anionic silicone | 1.5 | 1.05 | 1.06 | 1.25 |

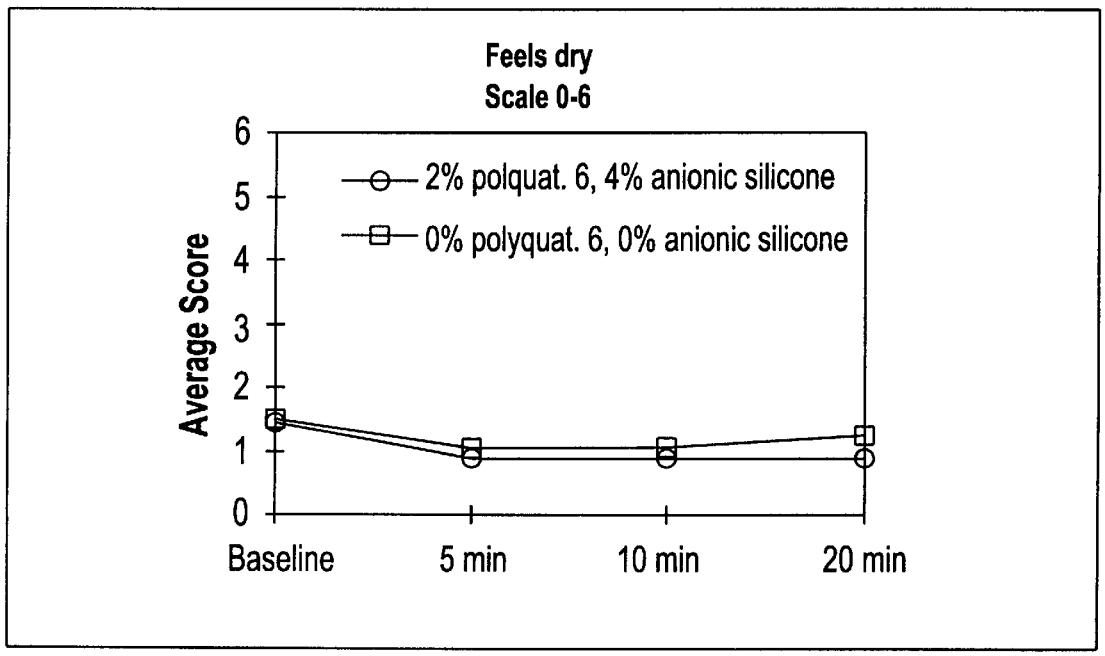

FIG.5H

SENSORY EVALUATION OF COMPLEX (DIFFERING ANIONICS)
31-JUL-97

CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Moisturize | 2% polquat. 6, 4% anionic silicone | 0 | 0.8 | 0.39 | 0.45 |
|  | 0% polyquat. 6, 0% anionic silicone | 0 | 0.4 | 0.44 | 0.15 |

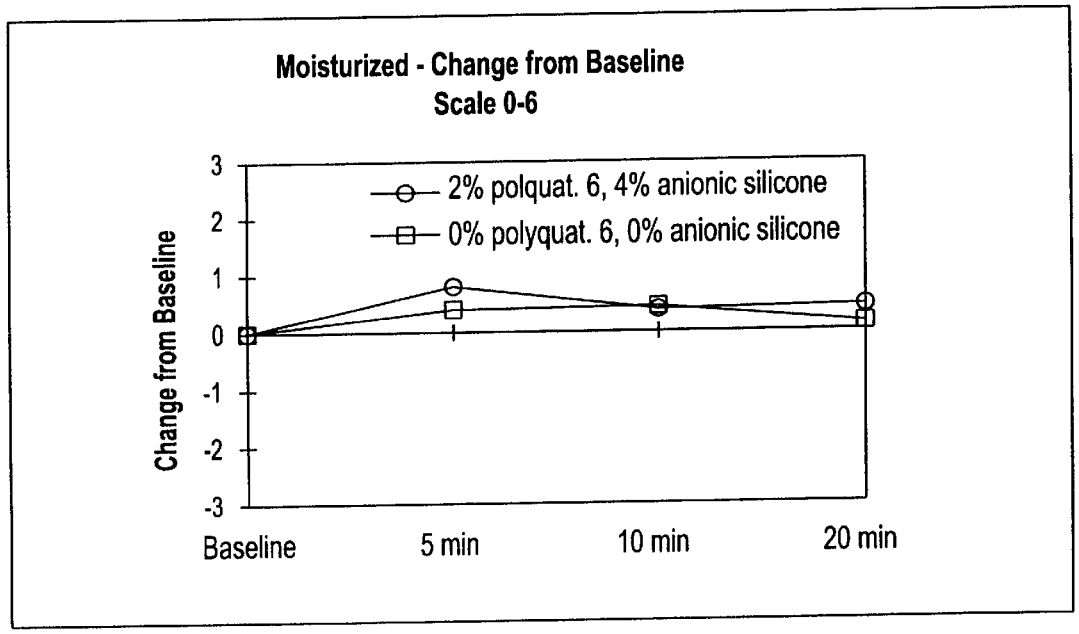

FIG.51

SENSORY EVALUATION OF COMPLEX (DIFFERING ANIONICS)
31-JUL-97

CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Plump / Hy | 2% polquat. 6, 4% anionic silicone | 0 | 0.85 | 0.56 | 0.6 |
|  | 0% polyquat. 6, 0% anionic silicone | 0 | 0.3 | 0.39 | -0.05 |

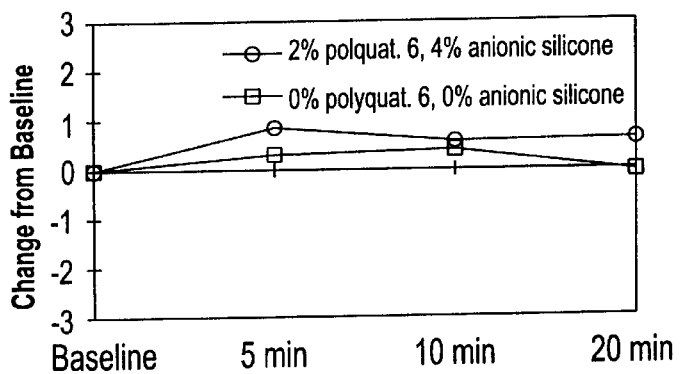

FIG.5J

SENSORY EVALUATION OF COMPLEX (DIFFERING ANIONICS)
31-JUL-97

CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Smooth | 2% polquat. 6, 4% anionic silicone | 0 | 0.3 | 0.28 | 0.3 |
|  | 0% polyquat. 6, 0% anionic silicone | 0 | -0.2 | 0.22 | -0.1 |

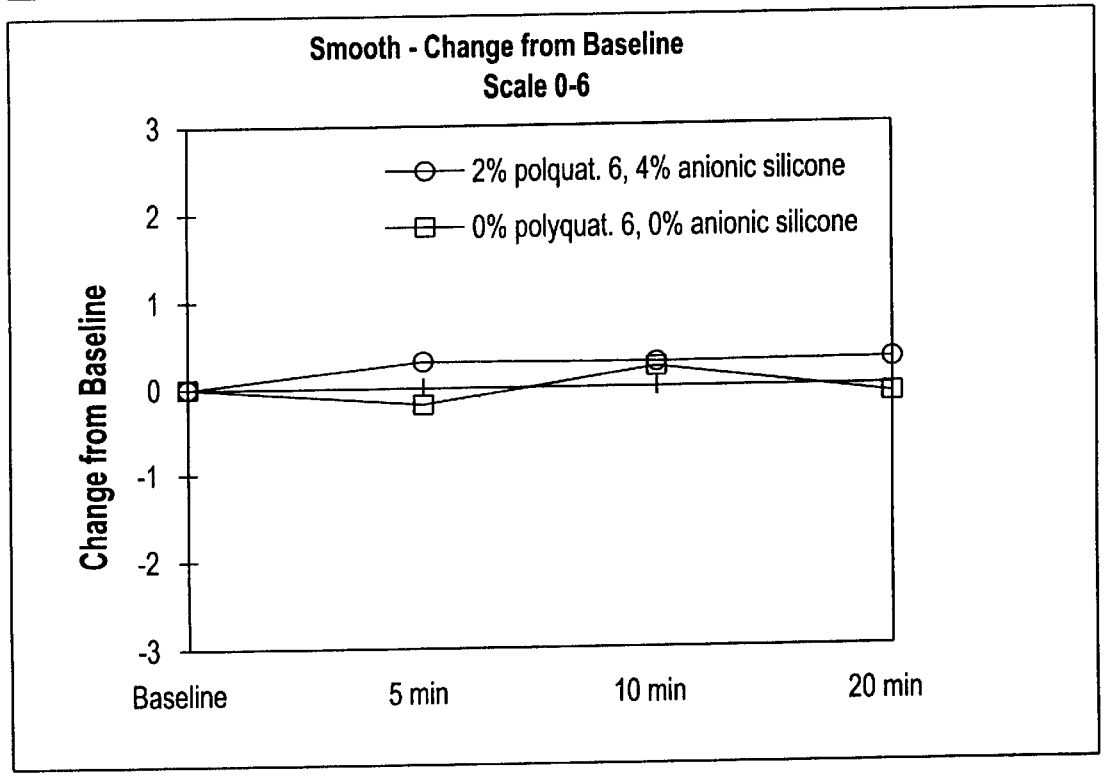

FIG.5K

SENSORY EVALUATION OF COMPLEX (DIFFERING ANIONICS)
31-JUL-97

CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Soft | 2% polquat. 6, 4% anionic silicone | 0 | 0.65 | 0.67 | 0.45 |
|  | 0% polyquat. 6, 0% anionic silicone | 0 | 0.35 | 0.22 | -0.1 |

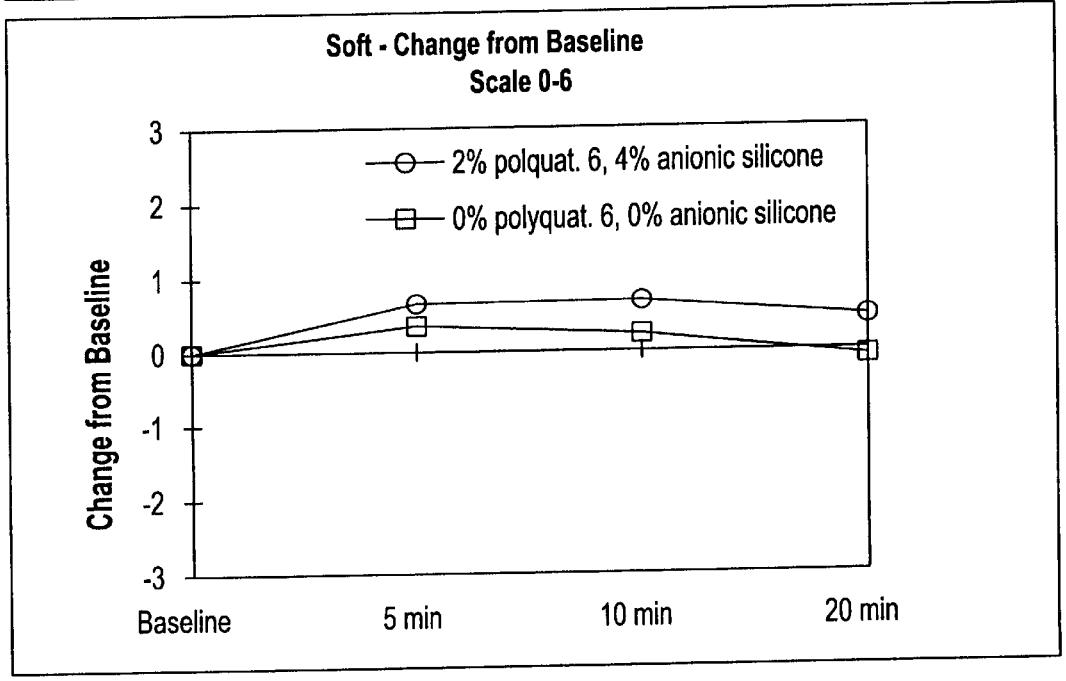

FIG.5L

SENSORY EVALUATION OF COMPLEX (DIFFERING ANIONICS)
31-JUL-97
CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Tight | 2% polquat. 6, 4% anionic silicone | 0 | -0.05 | -0.28 | 0 |
| | 0% polyquat. 6, 0% anionic silicone | 0 | -0.15 | -0.11 | 0.1 |

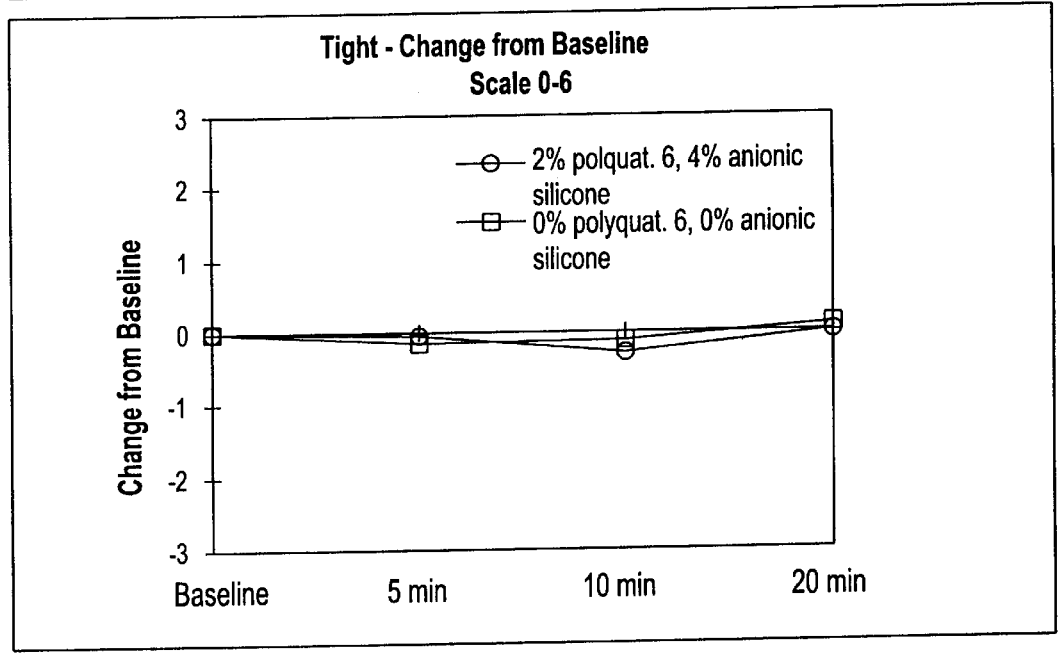

FIG.5M

SENSORY EVALUATION OF COMPLEX (DIFFERING ANIONICS)
31-JUL-97
CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Residue/C | 2% polquat. 6, 4% anionic silicone | 0 | 1.1 | 1.17 | 0.8 |
|  | 0% polyquat. 6, 0% anionic silicone | 0 | 0.7 | 0.67 | 0.4 |

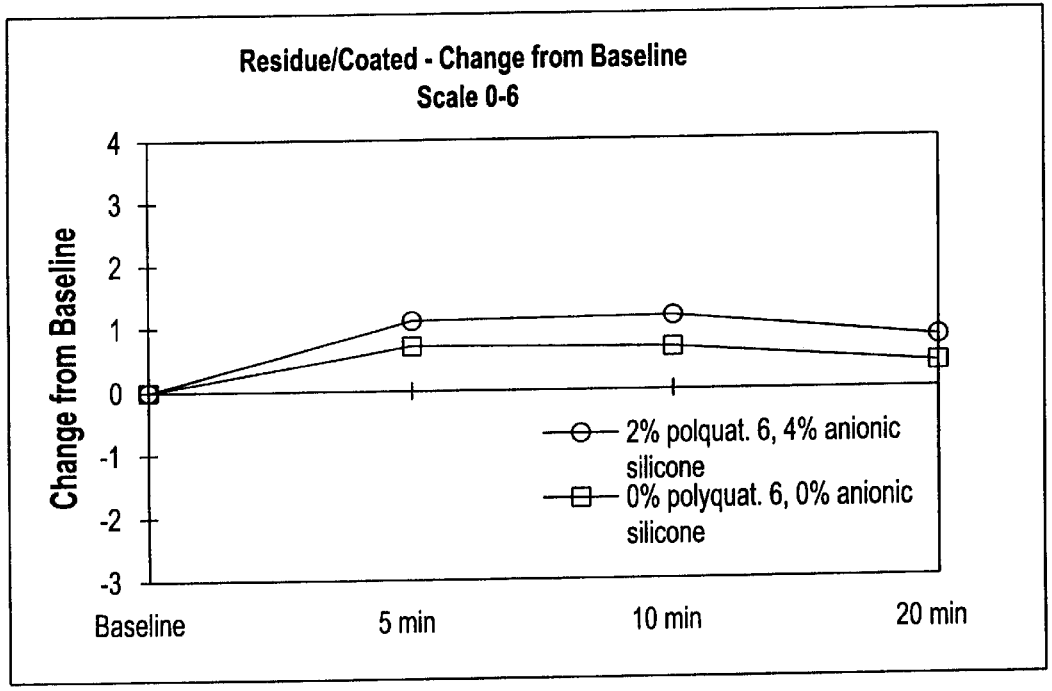

FIG.5N

SENSORY EVALUATION OF COMPLEX (DIFFERING ANIONICS)
31-JUL-97
CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Looks Dry | 2% polquat. 6, 4% anionic silicone | 0 | -0.25 | -0.22 | -0.25 |
| | 0% polyquat. 6, 0% anionic silicone | 0 | -0.3 | -0.11 | 0 |

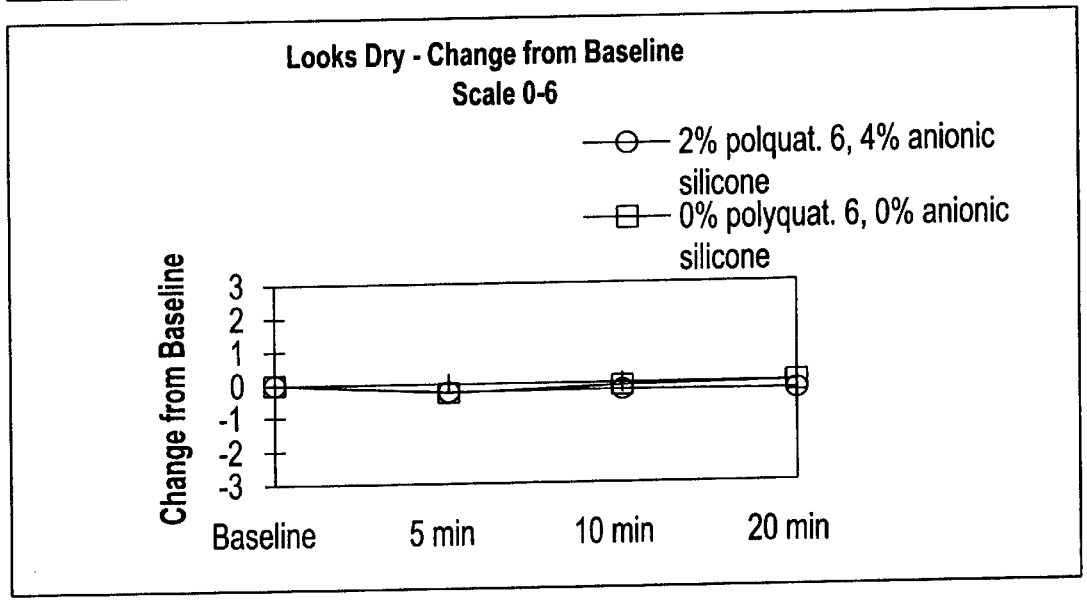

FIG.50

SENSORY EVALUATION OF COMPLEX (DIFFERING ANIONICS)
31-JUL-97
CONTRASTING HANDWASH FORMULAS: ONE WITH 2% POLYQUAT 6 AND 4% DIMETHICONE COPOLYOL PTHALATE ONE WITH 0% POLYQUATERNIUM 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Feels Dry | 2% polquat. 6, 4% anionic silicone | 0 | -0.55 | -0.39 | -0.55 |
|  | 0% polyquat. 6, 0% anionic silicone | 0 | -0.45 | -0.28 | -0.25 |

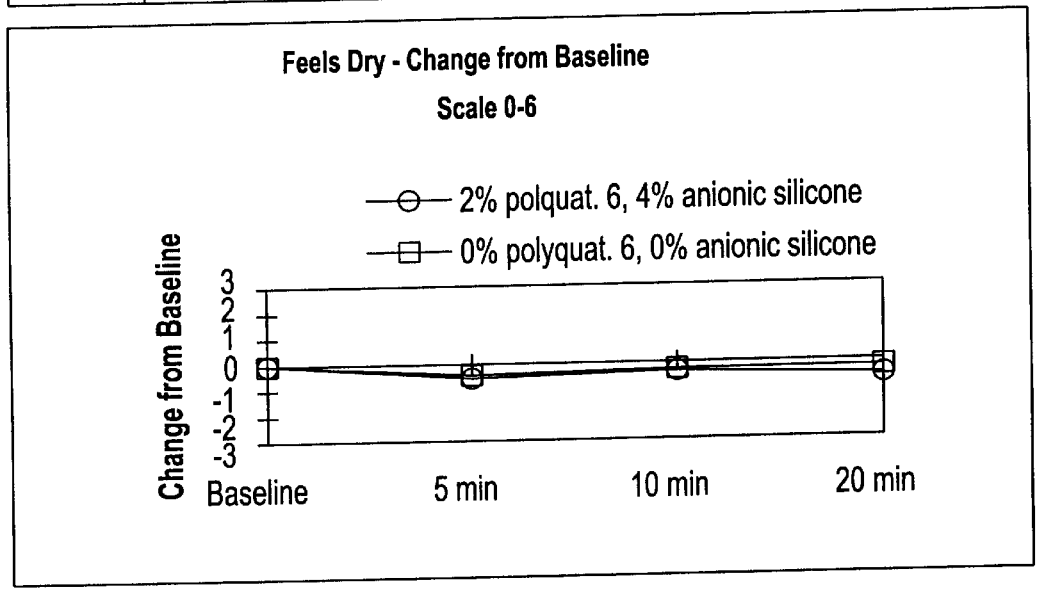

FIG.5P

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Average Scores

| Attribute | Product | Baseline | 5 min | 10 min | 20 min |
|---|---|---|---|---|---|
| Moisturize | 2% polquat. 6, 4% anionic ester | 2.9 | 2.95 | 2.5 | 2.6 |
|  | 0% polquat. 6, 0% anionic ester | 2.85 | 3.2 | 2.9 | 2.85 |

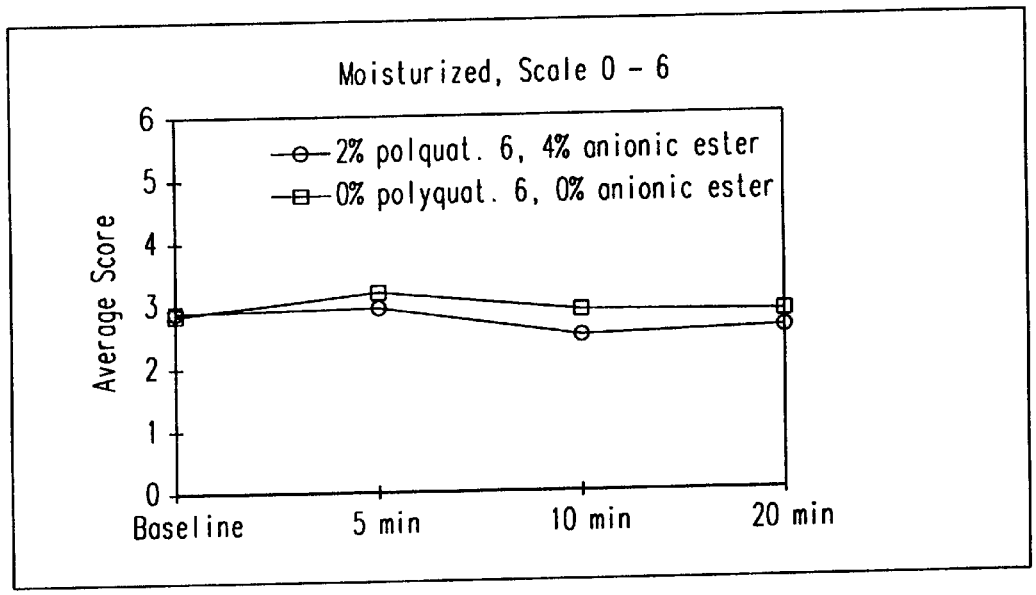

FIG.6A

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7
CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Average Scores

| Attribute | Product | Baseline | 5 min | 10 min | 20 min |
|---|---|---|---|---|---|
| Plump/Hy | 2% polquat. 6, 4% anionic | 2.4 | 2.8 | 2.6 | 2.6 |
| | 0% polyquat. 6, 0% anionic | 2.45 | 2.85 | 2.85 | 2.9 |

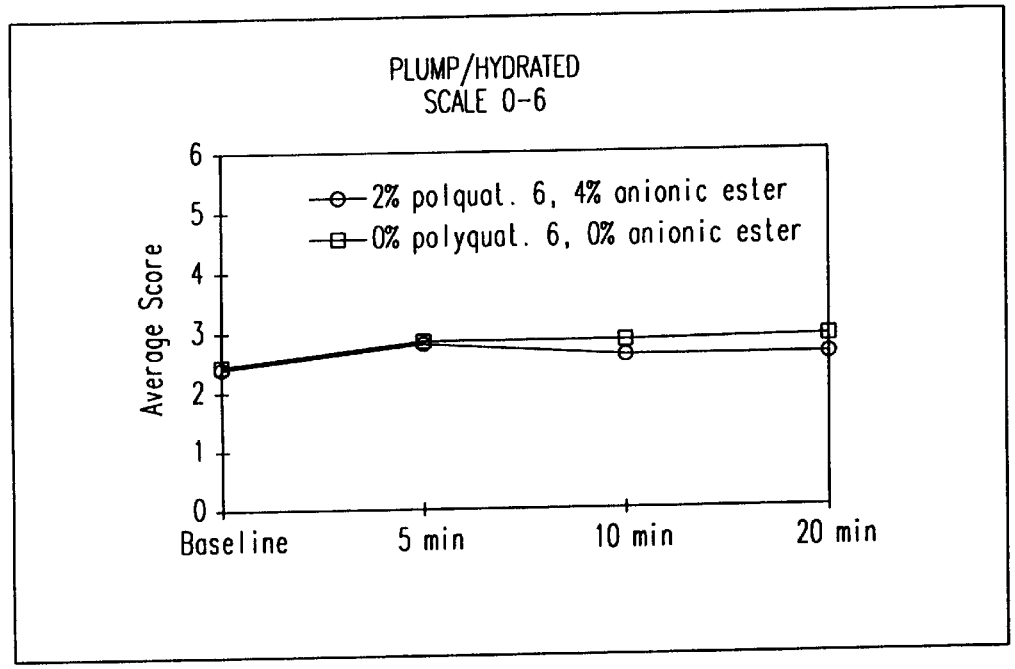

FIG.6B

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Average Scores

| Attribute | Product | Baseline | 5 min | 10 min | 20 min |
|---|---|---|---|---|---|
| Smooth | 2% polyquat. 6, 4% anionic | 3.55 | 3.75 | 3.4 | 3.25 |
| | 0% polyquat. 6, 0% anionic | 3.3 | 3.25 | 3.05 | 3.1 |

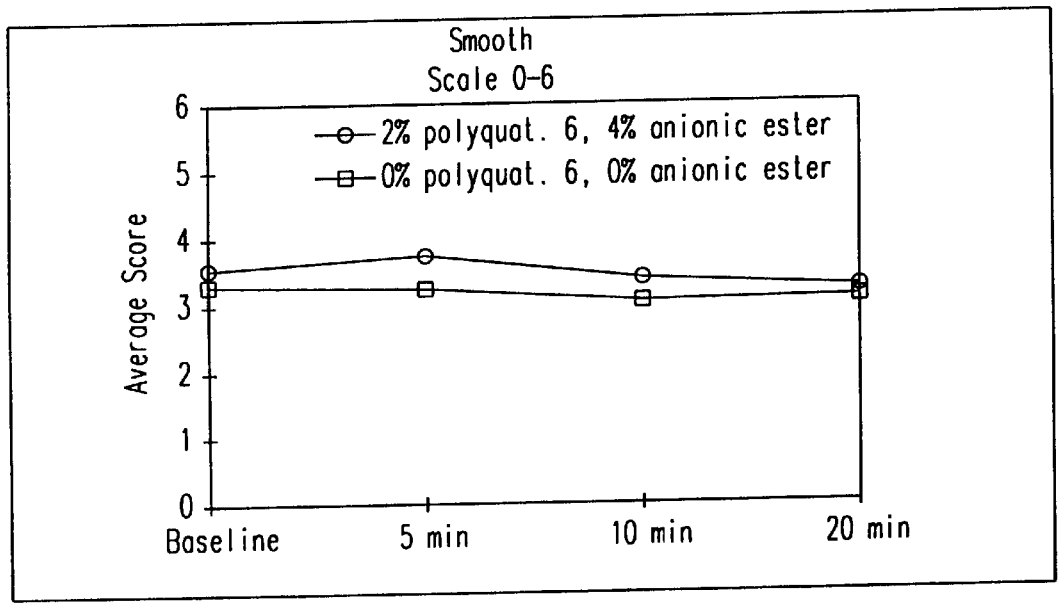

FIG.6C

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Average Scores

| Attribute | Product | Baseline | 5 min | 10 min | 20 min |
|---|---|---|---|---|---|
| Soft | 2% polquat. 6, 4% anionic | 3.28 | 3.25 | 3.05 | 3 |
|  | 0% polquat. 6, 0% anionic | 3.11 | 3.5 | 3.1 | 3.25 |

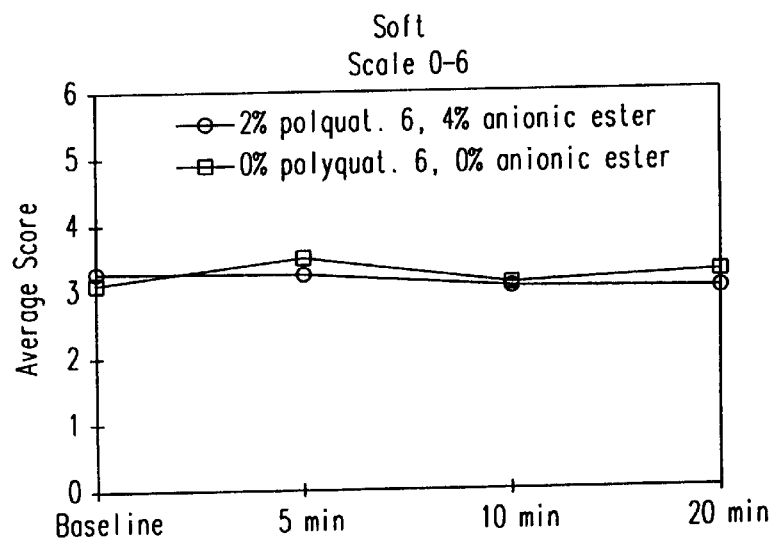

FIG.6D

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7
CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Average Scores

| Attribute | Product | Baseline | 5 min | 10 min | 20 min |
|---|---|---|---|---|---|
| Tight | 2% polquat. 6, 4% anionic | 0.75 | 1.25 | 1.45 | 1.3 |
|  | 0% polquat. 6, 0% anionic | 0.65 | 1.25 | 1.45 | 1.2 |

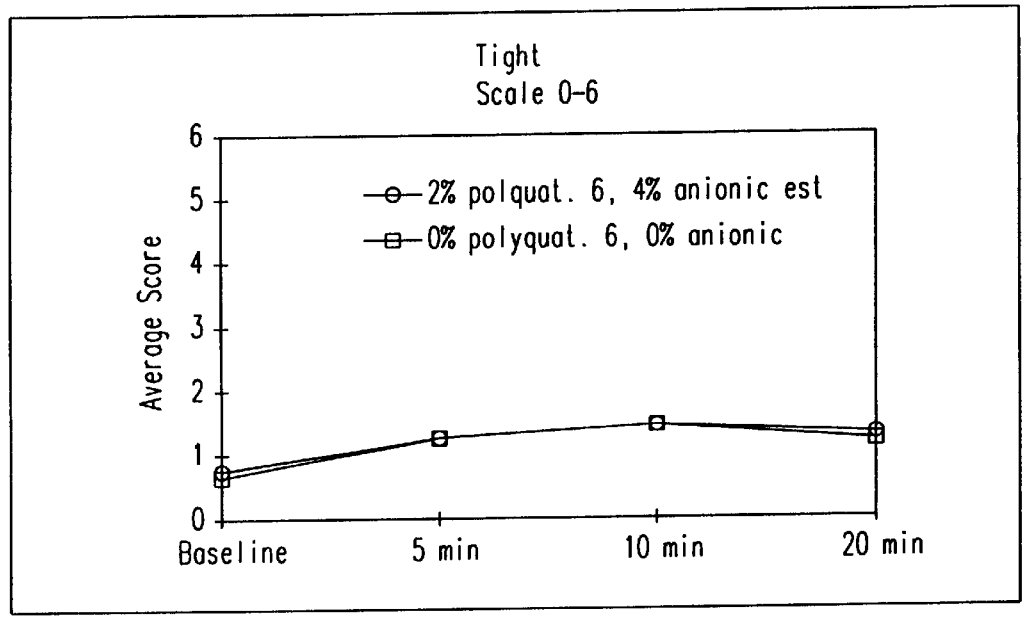

FIG.6E

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Average Scores

| Attribute | Product | Baseline | 5 min | 10 min | 20 min |
|---|---|---|---|---|---|
| Residue/C | 2% polquat. 6, 4% anionic | 0.25 | 0.75 | 1 | 0.75 |
|  | 0% polquat. 6, 0% anionic | 0.25 | 0.95 | 1.15 | 0.85 |

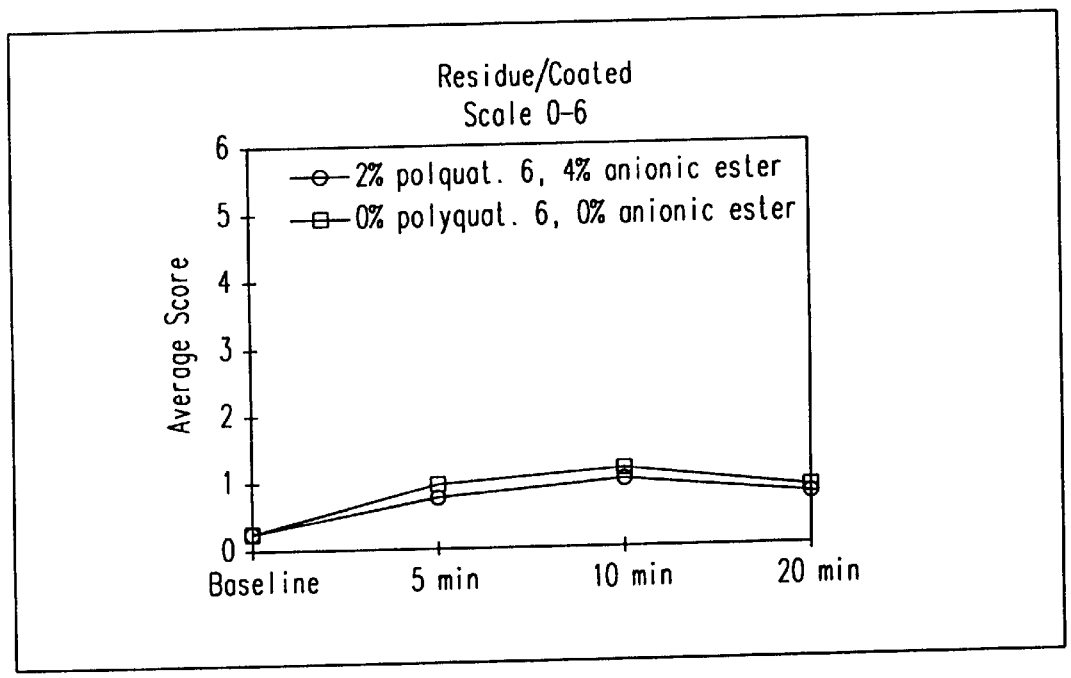

FIG.6F

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Average Scores

| Attribute | Product | Baseline | 5 min | 10 min | 20 min |
|---|---|---|---|---|---|
| Looks Dry | 2% polquat. 6, 4% anionic | 0.45 | 0.65 | 0.65 | 0.75 |
|  | 0% polyquat. 6, 0% anionic | 0.45 | 0.65 | 0.75 | 0.75 |

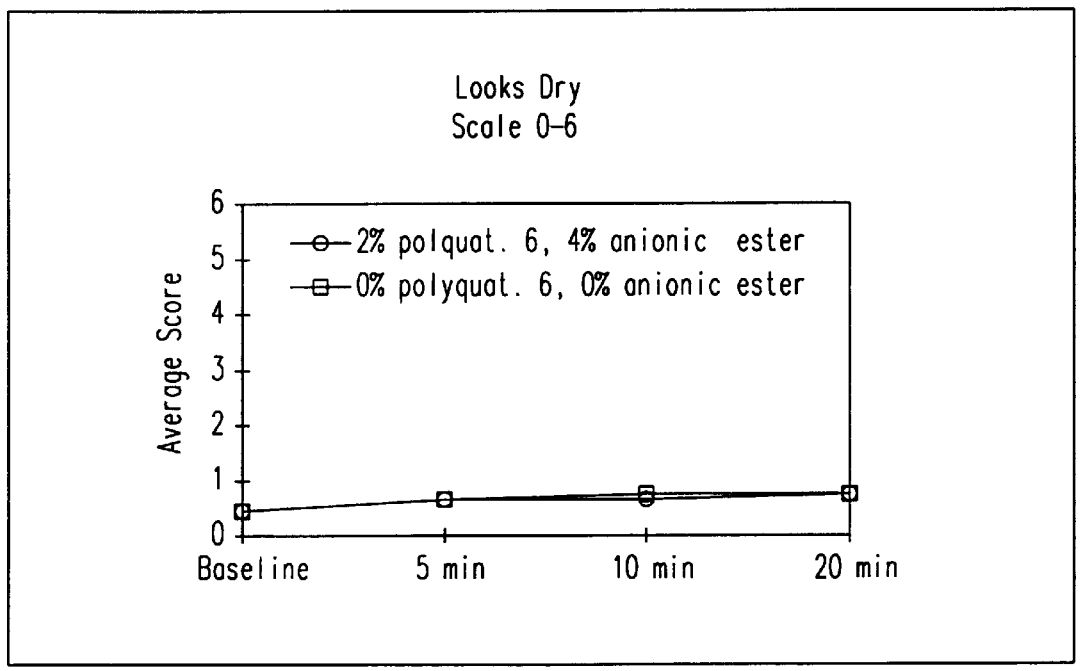

FIG.6G

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Average Scores

| Attribute | Product | Baseline | 5 min | 10 min | 20 min |
|---|---|---|---|---|---|
| Feels Dry | 2% polquat. 6, 4% anionic | 0.15 | 0.65 | 0.8 | 0.8 |
|  | 0% polyquat. 6, 0% anionic | 0.25 | 0.45 | 0.55 | 0.6 |

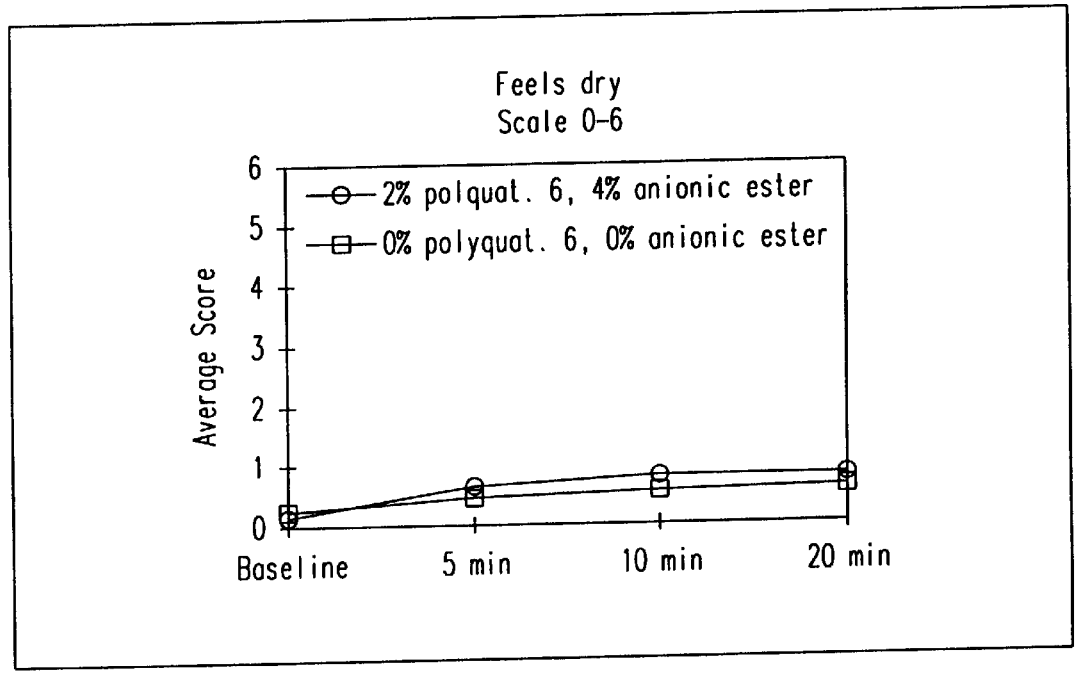

FIG.6H

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Change from Baseline

| Attribute | Product | Baseline | 5 min | 10 min | 20 min |
|---|---|---|---|---|---|
| Moisturize | 2% polquat. 6, 4% anionic | 0 | 0.05 | -0.4 | -0.3 |
| | 0% polyquat. 6, 0% anionic | 0 | 0.35 | 0.05 | 0 |

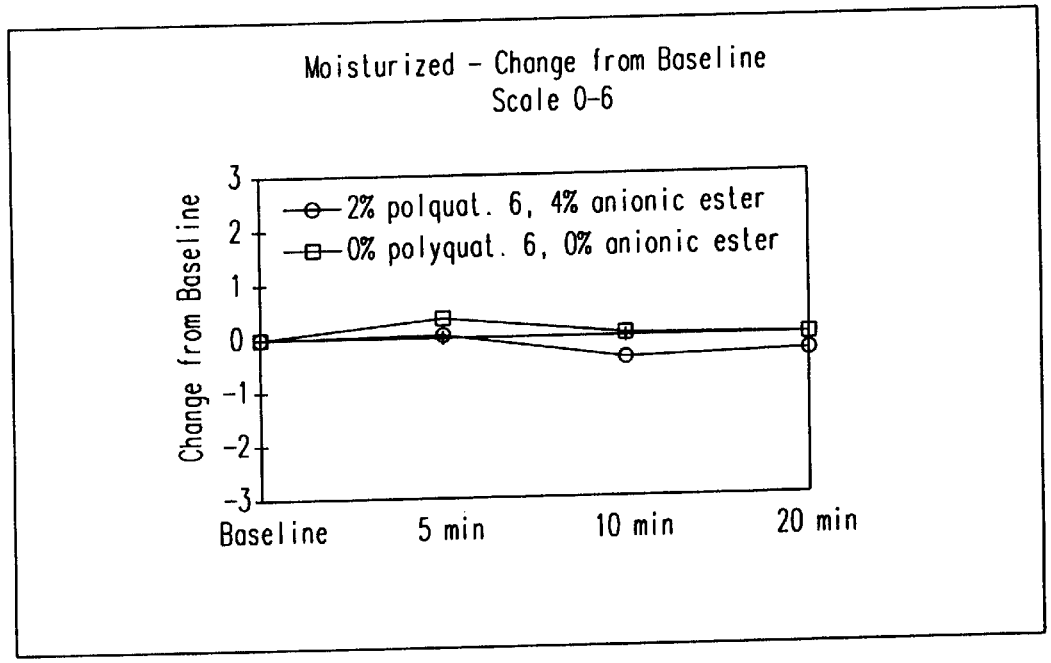

FIG. 61

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10
Change from Baseline

| Attribute | Product | Baseline | 5 min | 10 min | 20 min |
|---|---|---|---|---|---|
| Plump/Hy | 2% polquat. 6, 4% anionic | 0 | 0.4 | 0.2 | 0.2 |
|  | 0% polquat. 6, 0% anionic | 0 | 0.4 | 0.4 | 0.45 |

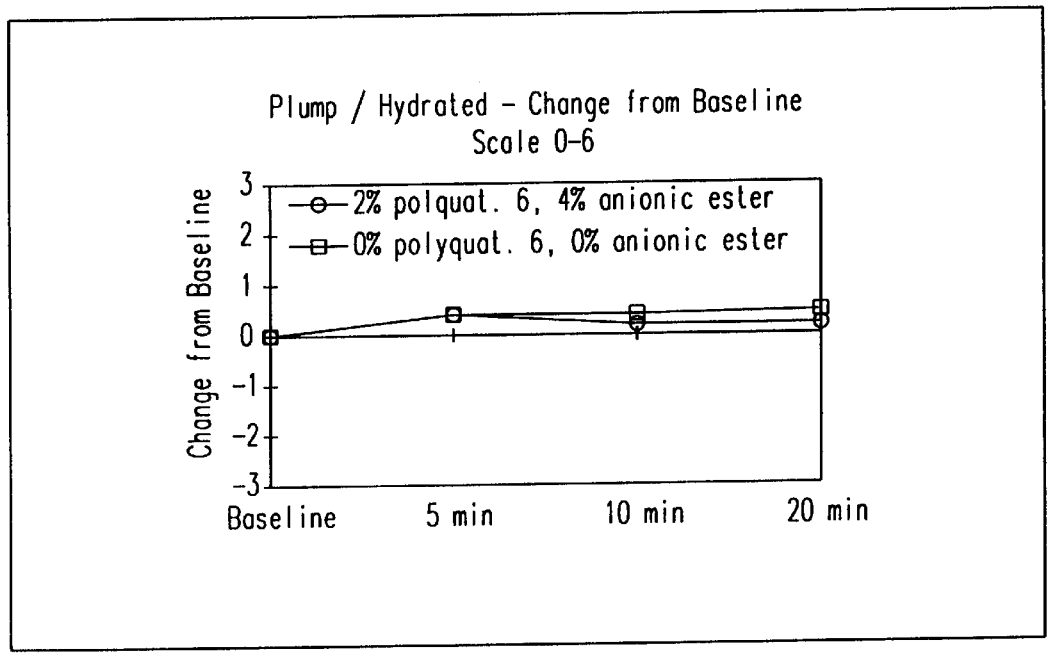

FIG.6J

SENSORY EVALUATION OF COMPLEX (DIFFERING ANIONICS)
31-JUL-97

CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Change from Baseline

| Attribute | Product | Baseline | 5 min | 10 min | 20 min |
|---|---|---|---|---|---|
| Smooth | 2% polquat. 6, 4% anionic | 0 | 0.2 | -0.15 | -0.3 |
| | 0% polyquat. 6, 0% anionic | 0 | -0.05 | -0.25 | -0.2 |

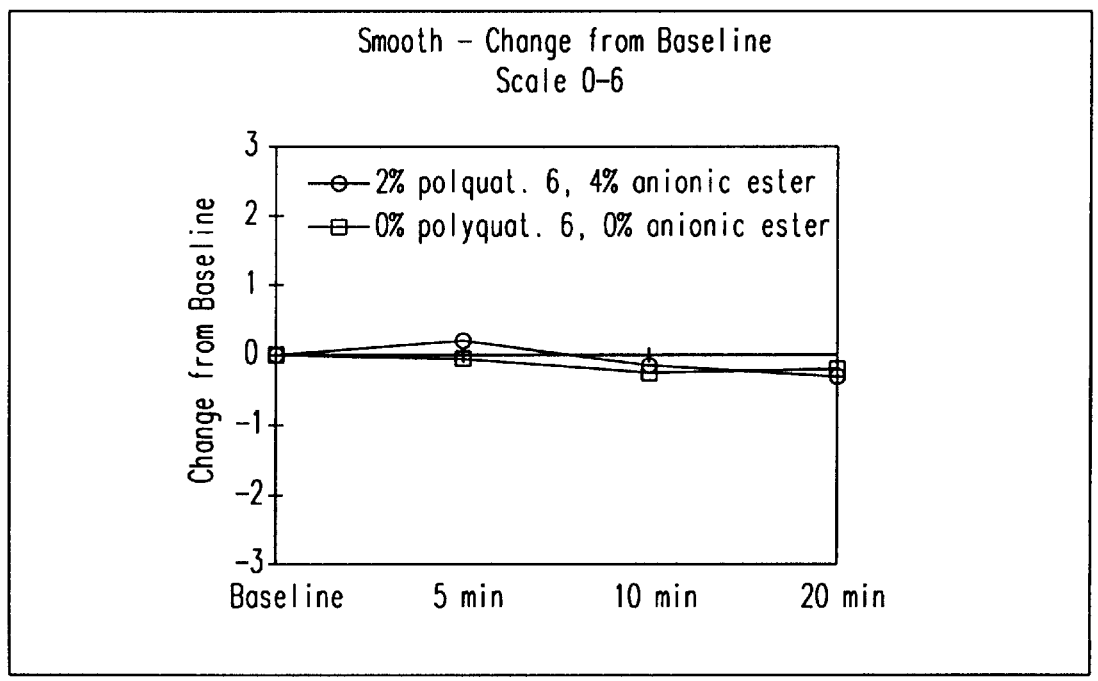

FIG.6K

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10
Change from Baseline

| Attribute | Product | Baseline | 5 min | 10 min | 20 min |
|---|---|---|---|---|---|
| Soft | 2% polquat. 6, 4% anionic | 0 | 0.3 | 0.1 | 0.05 |
|  | 0% polquat. 6, 0% anionic | 0 | 0.7 | 0.3 | 0.45 |

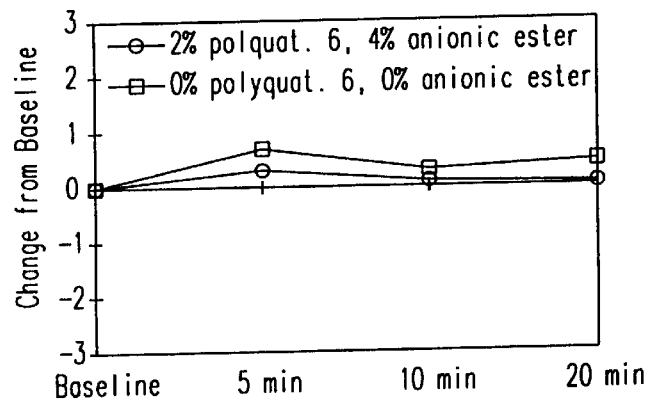

FIG.6L

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10
Change from Baseline

| Attribute | Product | Baseline | 5 min | 10 min | 20 min |
|---|---|---|---|---|---|
| Tight | 2% polquat. 6, 4% anionic | 0 | 0.5 | 0.7 | 0.55 |
|  | 0% polquat. 6, 0% anionic | 0 | 0.6 | 0.8 | 0.55 |

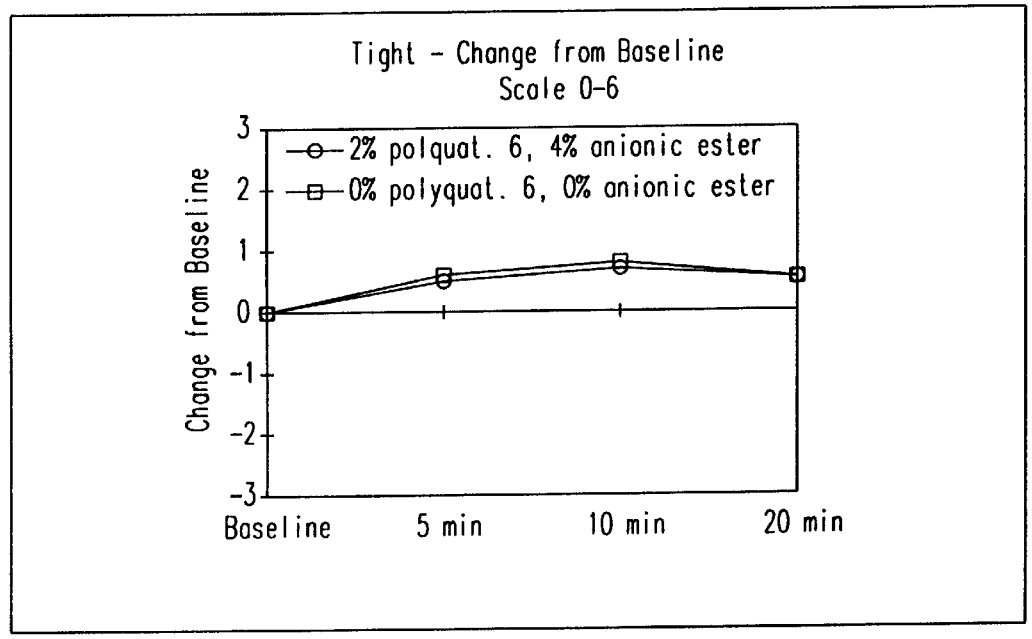

FIG.6M

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10
Change from Baseline

| Attribute | Product | Baseline | 5 min | 10 min | 20 min |
|---|---|---|---|---|---|
| Residue/C | 2% polquat. 6, 4% anionic | 0 | 0.5 | 0.75 | 0.5 |
|  | 0% polquat. 6, 0% anionic | 0 | 0.7 | 0.9 | 0.6 |

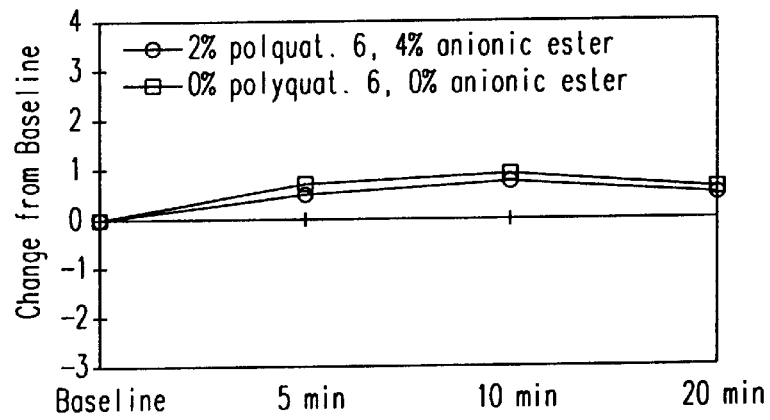

FIG.6N

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Change from Baseline

| Attribute | Product | Baseline | 5 min | 10 min | 20 min |
|---|---|---|---|---|---|
| Looks Dry | 2% polquat. 6, 4% anionic | 0 | 0.2 | 0.2 | 0.3 |
|  | 0% polyquat. 6, 0% anionic | 0 | 0.2 | 0.3 | 0.3 |

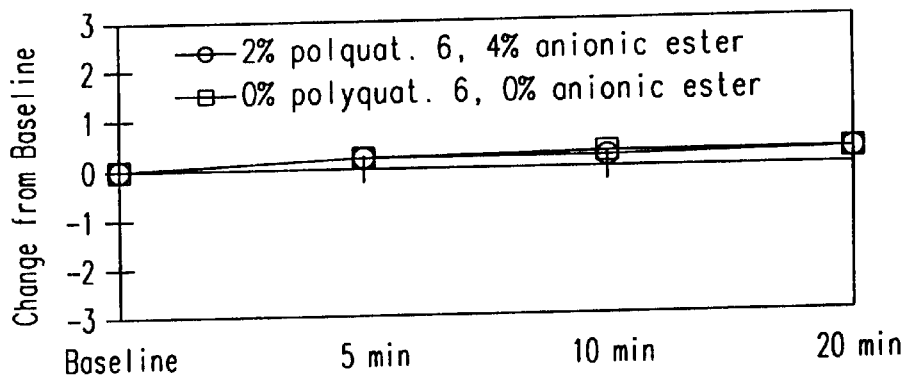

FIG.60

SENSORY EVALUATION OF COMPLEX (DIFFERING ANIONICS)
31-JUL-97
CONTRASTING HANDWASH FORMULAS: ONE WITH 2% POLYQUAT 6 AND 4% ISOPROPYL PPG-2-ISODECETH-7 CARBOXYLATE, ONE WITH 0% POLYQUATERNIUM 6 AND 0% ISOPROPYL PPG-2-ISODECETH-7 CARBOXYLATE

2% POLYQUAT 6 AND 4% ANIONIC ESTER, N=10
0% POLYQUAT 6 AND 0% ANIONIC ESTER, N=10

Change from Baseline

| Attribute | Product | Baseline | 5 min | 10 min | 20 min |
|---|---|---|---|---|---|
| Feels Dry | 2% polquat. 6, 4% anionic | 0 | 0.5 | 0.65 | 0.65 |
| | 0% polquat. 6, 0% anionic | 0 | 0.2 | 0.3 | 0.35 |

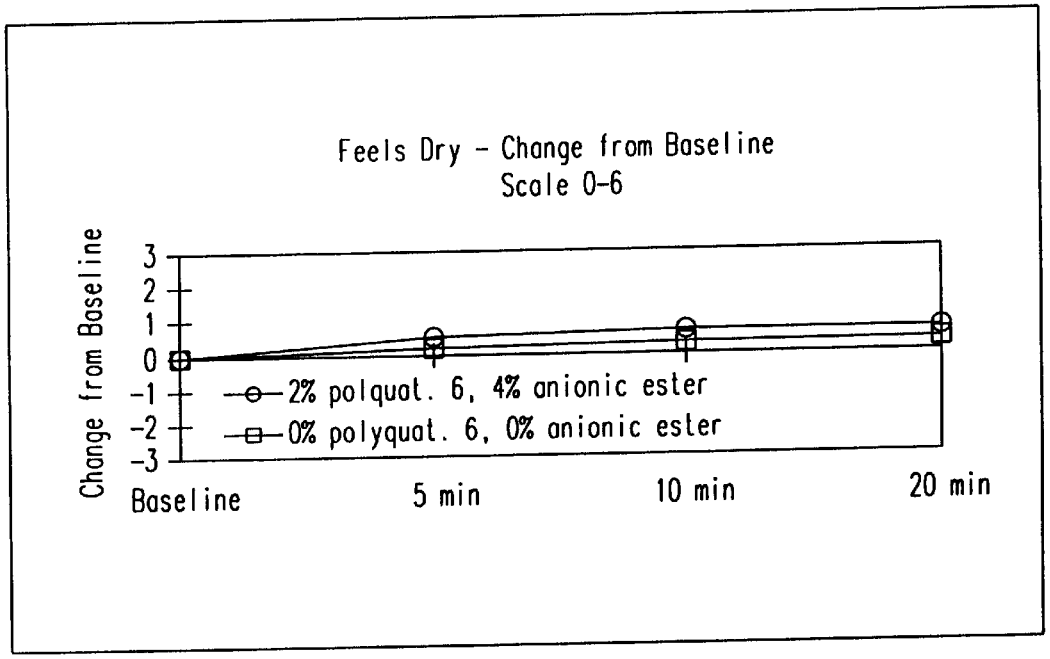

FIG.6P

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9

Average Scores

| Attribute | Product | Baseline | 5 min | 10 min | 20 min |
|---|---|---|---|---|---|
| Moisturize | 2% PEI, 4% SCO | 2.61 | 2.56 | 2.38 | 2.78 |
| | 0% PEI, 0% SCO | 2.61 | 2.67 | 2.75 | 2.78 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO

2% POLYQUAT 6 AND 4% ANIONIC ESTER, N=9
0% POLYQUAT 6 AND 0% ANIONIC ESTER, N=9

Average Scores

| Attribute | Product | Baseline | 5 min | 10 min | 20 min |
|---|---|---|---|---|---|
| Plump/Hy | 2% PEI, 4% SCO | 2.39 | 2.67 | 2.38 | 2.83 |
|  | 0% PEI, 0% SCO | 2.39 | 2.61 | 2.44 | 2.72 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9
Average Scores

| Attribute | Product | Baseline | 5 min | 10 min | 20 min |
|---|---|---|---|---|---|
| Smooth | 2% PEI, 4% SCO | 3.56 | 2.94 | 3 | 3.5 |
| | 0% PEI, 0% SCO | 3.56 | 3.33 | 3.44 | 3.83 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9
Average Scores

| Attribute | Product | Baseline | 5 min | 10 min | 20 min |
|---|---|---|---|---|---|
| Soft | 2% PEI, 4% SCO | 3.06 | 2.72 | 3.06 | 3.17 |
| | 0% PEI, 0% SCO | 3.06 | 3.06 | 3 | 3.28 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO

2% POLYQUAT 6 AND 4% ANIONIC ESTER, N=9
0% POLYQUAT 6 AND 0% ANIONIC ESTER, N=9

Average Scores

| Attribute | Product | Baseline | 5 min | 10 min | 20 min |
|---|---|---|---|---|---|
| Tight | 2% PEI, 4% SCO | 0.78 | 1.44 | 1.5 | 1.22 |
| | 0% PEI, 0% SCO | 0.78 | 1.88 | 1.5 | 1.11 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9

Average Scores

| Attribute | Product | Baseline | 5 min | 10 min | 20 min |
|---|---|---|---|---|---|
| Residue/Coated | 2% PEI, 4% SCO | 0.39 | 0.94 | 0.94 | 0.83 |
| | 0% PEI, 0% SCO | 0.39 | 1.25 | 0.81 | 0.61 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9

Average Scores

| Attribute | Product | Baseline | 5 min | 10 min | 20 min |
|---|---|---|---|---|---|
| Looks Dry | 2% PEI, 4% SCO | 0.78 | 1 | 1 | 0.89 |
|  | 0% PEI, 0% SCO | 0.78 | 0.81 | 0.94 | 0.94 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9

Average Scores

| Attribute | Product | Baseline | 5 min | 10 min | 20 min |
|---|---|---|---|---|---|
| Feels Dry | 2% PEI, 4% SCO | 0.83 | 1.75 | 1.63 | 1.11 |
| | 0% PEI, 0% SCO | 0.78 | 1.19 | 1.31 | 1 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9
Change from Baseline

| Attribute | Product | Baseline | 5 min | 10 min | 20 min |
|---|---|---|---|---|---|
| Moisturize | 2% PEI, 4% SCO | 0 | -0.05 | -0.22 | 0.15 |
| | 0% PEI, 0% SCO | 0 | 0.05 | 0.11 | 0.15 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO

2% POLYQUAT 6 AND 4% ANIONIC ESTER, N=9
0% POLYQUAT 6 AND 0% ANIONIC ESTER, N=9

Change from Baseline

| Attribute | Product | Baseline | 5 min | 10 min | 20 min |
|---|---|---|---|---|---|
| Plump/Hy | 2% PEI, 4% SCO | 0 | 0.25 | -0.06 | 0.4 |
|  | 0% PEI, 0% SCO | 0 | 0.2 | 0 | 0.3 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO

2% POLYQUAT 6 AND 4% ANIONIC ESTER, N=9
0% POLYQUAT 6 AND 0% ANIONIC ESTER, N=9

Change from Baseline

| Attribute | Product | Baseline | 5 min | 10 min | 20 min |
|---|---|---|---|---|---|
| Smooth | 2% PEI, 4% SCO | 0 | -0.55 | -0.33 | -0.05 |
| | 0% PEI, 0% SCO | 0 | -0.2 | 0.06 | 0.25 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9
Change from Baseline

| Attribute | Product | Baseline | 5 min | 10 min | 20 min |
|---|---|---|---|---|---|
| Soft | 2% PEI, 4% SCO | 0 | -0.3 | -0.11 | 0.1 |
| | 0% PEI, 0% SCO | 0 | 0 | -0.17 | 0.2 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9

Change from Baseline

| Attribute | Product | Baseline | 5 min | 10 min | 20 min |
|---|---|---|---|---|---|
| Tight | 2% PEI, 4% SCO | 0 | 0.45 | 0.67 | 0.4 |
| | 0% PEI, 0% SCO | 0 | 0.8 | 0.67 | 0.3 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO

2% POLYQUAT 6 AND 4% ANIONIC ESTER, N=9
0% POLYQUAT 6 AND 0% ANIONIC ESTER, N=9

Change from Baseline

| Attribute | Product | Baseline | 5 min | 10 min | 20 min |
|---|---|---|---|---|---|
| Residue/Coated | 2% PEI, 4% SCO | 0 | 0.4 | 0.44 | 0.4 |
| | 0% PEI, 0% SCO | 0 | 0.65 | 0.33 | 0.2 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO
2% POLYQUAT 6 AND 4% ANIONIC ESTER, N=9
0% POLYQUAT 6 AND 0% ANIONIC ESTER, N=9
Change from Baseline

| Attribute | Product | Baseline | 5 min | 10 min | 20 min |
|---|---|---|---|---|---|
| Looks Dry | 2% PEI, 4% SCO | 0 | 0.1 | 0.22 | 0.1 |
| | 0% PEI, 0% SCO | 0 | -0.05 | 0.17 | 0.15 |

SENSORY EVALUATION OF COMPLEX (USING PEI AS CATIONIC)
1-AUG-97
CONTRASTING HANDWASH FORMULAS: ONE WITH 2% NEUTRALIZED POLYETHYLENIMINE AND 4% SCO ONE WITH 0% POLYETHYLENIMINE AND 0% SCO

2% POLYQUAT 6 AND 4% ANIONIC ESTER, N=9
0% POLYQUAT 6 AND 0% ANIONIC ESTER, N=9

Change from Baseline

| Attribute | Product | Baseline | 5 min | 10 min | 20 min |
|---|---|---|---|---|---|
| Feels Dry | 2% PEI, 4% SCO | 0 | 0.65 | 0.72 | 0.25 |
|  | 0% PEI, 0% SCO | 0 | 0.25 | 0.5 | 0.2 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10

Average Scores

| Attribute | Product | Baseline | 5 min | 10 min | 20 min |
|---|---|---|---|---|---|
| Moisturize | 1.6% polyquat. 6, 3.5% SC | 2.45 | 3.65 | 3.45 | 3.25 |
|  | 0% polyquat. 6, 0% SCO | 2.6 | 3.4 | 3.2 | 3.1 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10
Average Scores

| Attribute | Product | Baseline | 5 min | 10 min | 20 min |
|---|---|---|---|---|---|
| Plump/Hy | 1.6% polyquat. 6, 3.5% SC | 1.85 | 2.9 | 2.9 | 2.6 |
|  | 0% polyquat. 6, 0% SCO | 2.1 | 3.45 | 2.95 | 2.85 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO 1.6% POLYQUAT. 6 AND 3.5% SCO, N=10
0% POLYQUAT. 6 AND 0% SCO, N=10

Average Scores

| Attribute | Product | Baseline | 5 min | 10 min | 20 min |
|---|---|---|---|---|---|
| Smooth | 1.6% polyquat. 6, 3.5% SC | 2.7 | 3.35 | 3.25 | 3.1 |
| | 0% polyquat. 6, 0% SCO | 3.05 | 3.45 | 3.8 | 3.35 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10
Average Scores

| Attribute | Product | Baseline | 5 min | 10 min | 20 min |
|---|---|---|---|---|---|
| Soft | 1.6% polyquat. 6, 3.5% SC | 2.45 | 3.4 | 3.35 | 3.25 |
| | 0% polyquat. 6, 0% SCO | 2.75 | 3.45 | 3.8 | 3.5 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10

Average Scores

| Attribute | Product | Baseline | 5 min | 10 min | 20 min |
|---|---|---|---|---|---|
| Tight | 1.6% polyquat. 6, 3.5% SC | 0.85 | 0.75 | 0.85 | 0.7 |
| | 0% polyquat. 6, 0% SCO | 0.6 | 0.55 | 0.95 | 0.8 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10

Average Scores

| Attribute | Product | Baseline | 5 min | 10 min | 20 min |
|---|---|---|---|---|---|
| Residue/Coated | 1.6% polyquat. 6, 3.5% SC | 0.4 | 2.15 | 2.05 | 1.5 |
|  | 0% polyquat. 6, 0% SCO | 0.3 | 1.55 | 1.55 | 1.3 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH
0% POLYQUAT. 6 AND 0% SCO
1.6% POLYQUAT. 6 AND 3.5% SCO, N=10
0% POLYQUAT. 6 AND 0% SCO, N=10
Average Scores

| Attribute | Product | Baseline | 5 min | 10 min | 20 min |
|---|---|---|---|---|---|
| Looks Dry | 1.6% polyquat. 6, 3.5% SC | 1.35 | 0.8 | 0.7 | 0.7 |
|  | 0% polyquat. 6, 0% SCO | 0.95 | 0.3 | 0.45 | 0.55 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH
0% POLYQUAT. 6 AND 0% SCO
1.6% POLYQUAT. 6 AND 3.5% SCO, N=10
0% POLYQUAT. 6 AND 0% SCO, N=10

Average Scores

| Attribute | Product | Baseline | 5 min | 10 min | 20 min |
|---|---|---|---|---|---|
| Feels Dry | 1.6% polyquat. 6, 3.5% SC | 1.55 | 0.8 | 0.7 | 1.05 |
| | 0% polyquat. 6, 0% SCO | 1.25 | 0.55 | 0.65 | 1.05 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10
Change from Baseline

| Attribute | Product | Baseline | 5 min | 10 min | 20 min |
|---|---|---|---|---|---|
| Moisturize | 1.6% polyquat. 6, 3.5% SC | 0 | 1.2 | 1.5 | 1.3 |
| | 0% polyquat. 6, 0% SCO | 0 | 0.8 | 1.2 | 1.1 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10
Change from Baseline

| Attribute | Product | Baseline | 5 min | 10 min | 20 min |
|---|---|---|---|---|---|
| Plump/Hy | 1.6% polyquat. 6, 3.5% SC | 0 | 1.05 | 1.45 | 1.15 |
| | 0% polyquat. 6, 0% SCO | 0 | 1.35 | 1.35 | 1.25 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO 1.6% POLYQUAT. 6 AND 3.5% SCO, N=10
0% POLYQUAT. 6 AND 0% SCO, N=10
Change from Baseline

| Attribute | Product | Baseline | 5 min | 10 min | 20 min |
|---|---|---|---|---|---|
| Smooth | 1.6% polyquat. 6, 3.5% SC | 0 | 0.65 | 1.15 | 1 |
|  | 0% polyquat. 6, 0% SCO | 0 | 0.4 | 1.45 | 1 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10
Change from Baseline

| Attribute | Product | Baseline | 5 min | 10 min | 20 min |
|---|---|---|---|---|---|
| Soft | 1.6% polyquat. 6, 3.5% SC | 0 | 0.95 | 1.4 | 1.3 |
|  | 0% polyquat. 6, 0% SCO | 0 | 0.7 | 1.65 | 1.35 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10
Change from Baseline

| Attribute | Product | Baseline | 5 min | 10 min | 20 min |
|---|---|---|---|---|---|
| Tight | 1.6% polyquat. 6, 3.5% SC | 0 | -0.1 | 0.2 | 0.05 |
|  | 0% polyquat. 6, 0% SCO | 0 | -0.05 | 0.45 | 0.3 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10
Change from Baseline

| Attribute | Product | Baseline | 5 min | 10 min | 20 min |
|---|---|---|---|---|---|
| Residue/Coated | 1.6% polyquat. 6, 3.5% SC | 0 | 1.75 | 1.75 | 1.2 |
| | 0% polyquat. 6, 0% SCO | 0 | 1.25 | 1.25 | 1 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO 1.6% POLYQUAT. 6 AND 3.5% SCO, N=10
0% POLYQUAT. 6 AND 0% SCO, N=10

Change from Baseline

| Attribute | Product | Baseline | 5 min | 10 min | 20 min |
|---|---|---|---|---|---|
| Looks Dry | 1.6% polyquat. 6, 3.5% SC | 0 | -0.55 | -0.35 | -0.35 |
| | 0% polyquat. 6, 0% SCO | 0 | -0.65 | -0.4 | -0.3 |

SENSORY EVALUATION OF COMPLEX (MODELING BATH BEADS)
1-AUG-97
CONTRASTING BATH FORMULAS: ONE WITH 1.6% POLYQUAT. 6 AND 3.5% SCO ONE WITH 0% POLYQUAT. 6 AND 0% SCO
1.6% POLYQUAT. 6 AND 3.5% SCO, N=10
0% POLYQUAT. 6 AND 0% SCO, N=10
Change from Baseline

| Attribute | Product | Baseline | 5 min | 10 min | 20 min |
|---|---|---|---|---|---|
| Feels Dry | 1.6% polyquat. 6, 3.5% SC | 0 | -0.75 | -0.55 | -0.2 |
|  | 0% polyquat. 6, 0% SCO | 0 | -0.7 | -0.4 | 0 |

SENSORY EVALUATION OF COMPLEX (ANIONIC SILICON IN AG BASE)
4-AUG-97

CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Moisturized | 2% polyquat.6, 4% anionic silicone | 2.5 | 3.55 | 3.05 | 2.75 |
| | 0% polyquat.6, 0% anionic silicone | 2.55 | 2.9 | 2.65 | 2.5 |

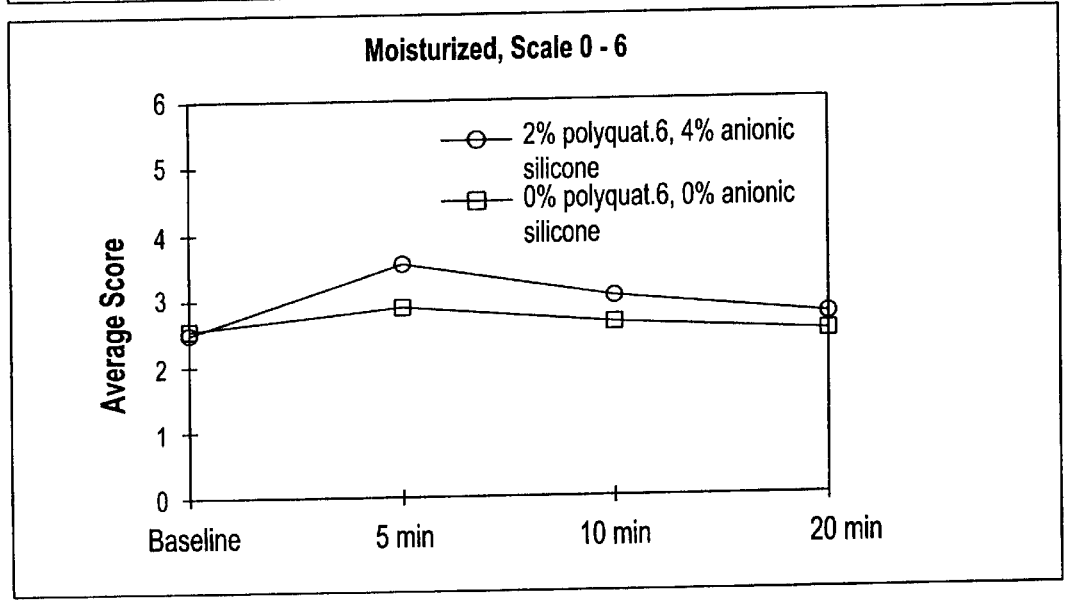

FIG.9A

SENSORY EVALUATION OF COMPLEX (ANIONIC SILICON IN AG BASE)
4-AUG-97

CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Plump / Hy | 2% polyquat.6, 4% anionic silicone | 2.3 | 3.3 | 2.6 | 2.5 |
| | 0% polyquat.6, 0% anionic silicone | 2.35 | 2.8 | 2.5 | 2.3 |

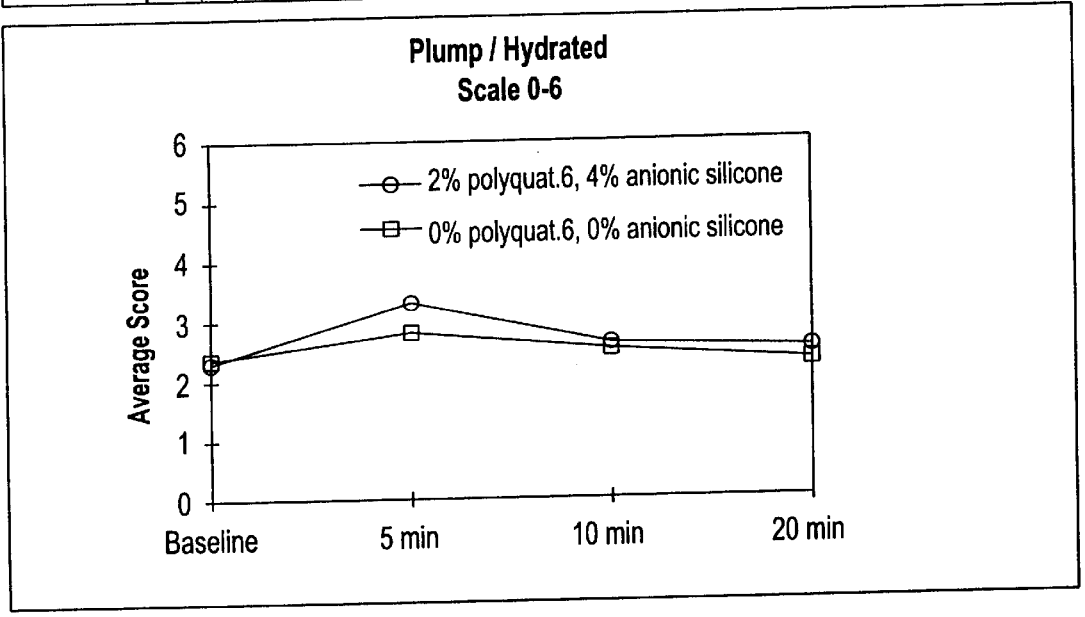

FIG.9B

SENSORY EVALUATION OF COMPLEX (ANIONIC SILICON IN AG BASE)
4-AUG-97
CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Smooth | 2% polyquat.6, 4% anionic silicone | 2.95 | 3.45 | 3.65 | 3.3 |
| | 0% polyquat.6, 0% anionic silicone | 3 | 3.35 | 3.35 | 3.15 |

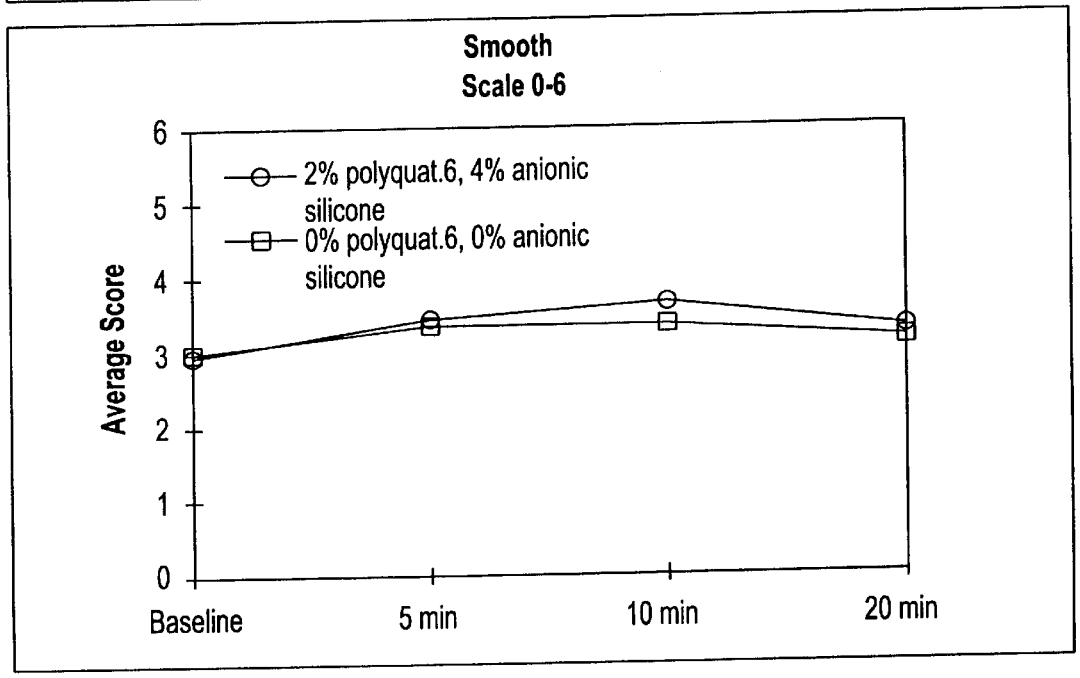

FIG.9C

SENSORY EVALUATION OF COMPLEX (ANIONIC SILICON IN AG BASE)
4-AUG-97

CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Soft | 2% polyquat.6, 4% anionic silicone | 3 | 3.95 | 3.35 | 3.15 |
| | 0% polyquat.6, 0% anionic silicone | 3.05 | 3.7 | 2.95 | 2.7 |

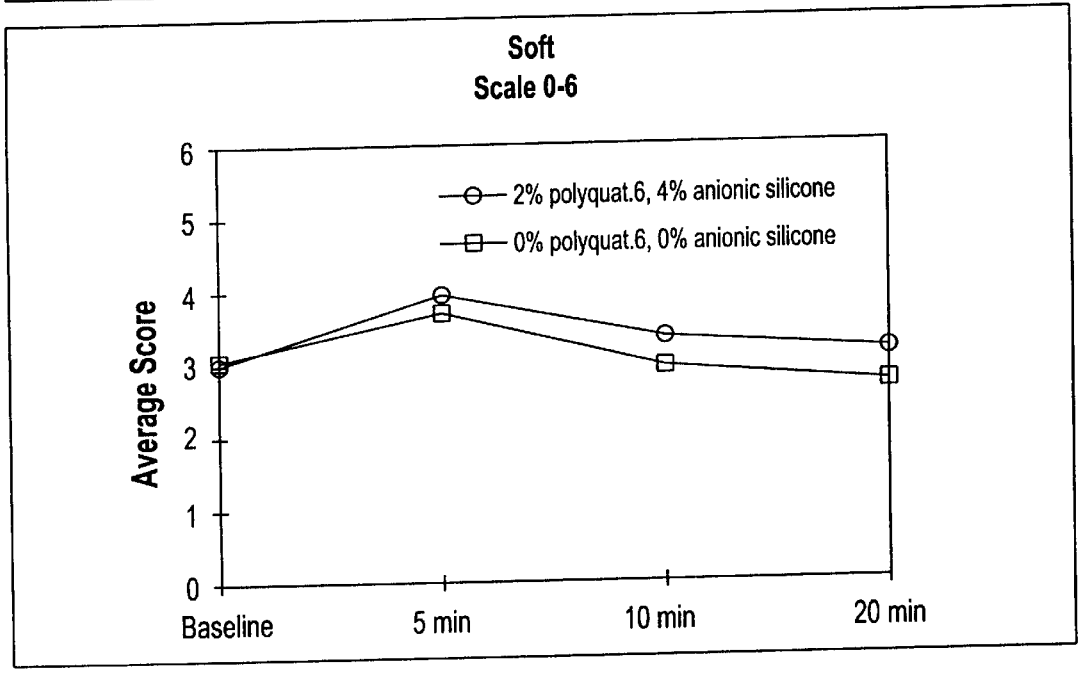

FIG.9D

SENSORY EVALUATION OF COMPLEX (ANIONIC SILICON IN AG BASE)
 4-AUG-97
CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Tight | 2% polyquat.6, 4% anionic silicone | 0.2 | 0.2 | 0.35 | 0.45 |
|  | 0% polyquat.6, 0% anionic silicone | 0.15 | 0.3 | 0.45 | 0.45 |

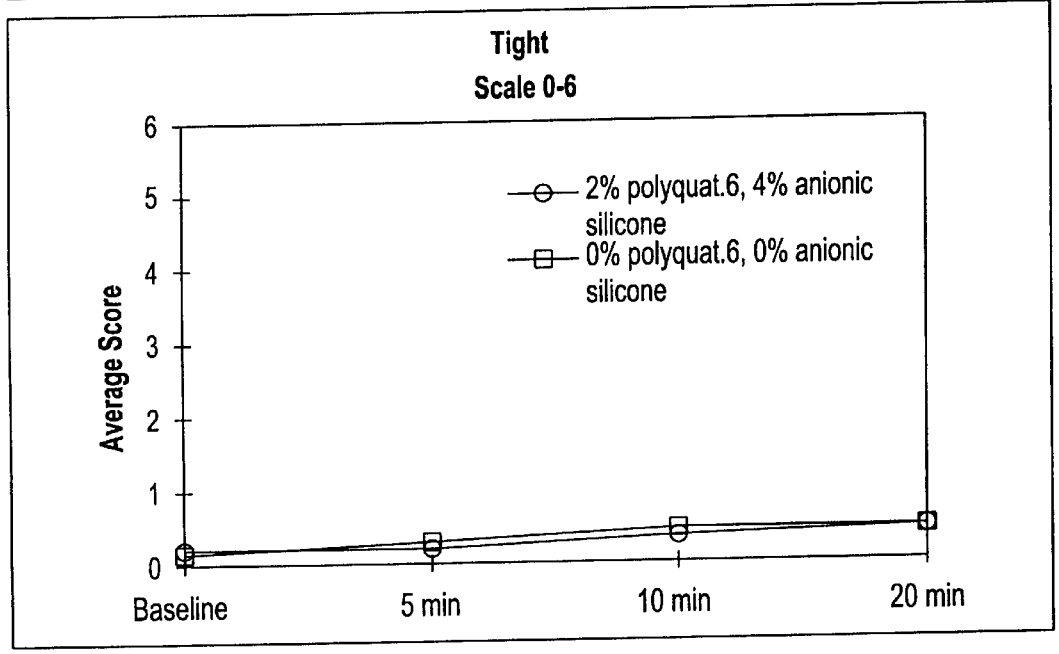

FIG.9E

SENSORY EVALUATION OF COMPLEX (ANIONIC SILICON IN AG BASE)
4-AUG-97

CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Residue/Coated | 2% polyquat.6, 4% anionic silicone | 0.4 | 1.5 | 1.25 | 0.9 |
| | 0% polyquat.6, 0% anionic silicone | 0.4 | 0.9 | 0.9 | 0.7 |

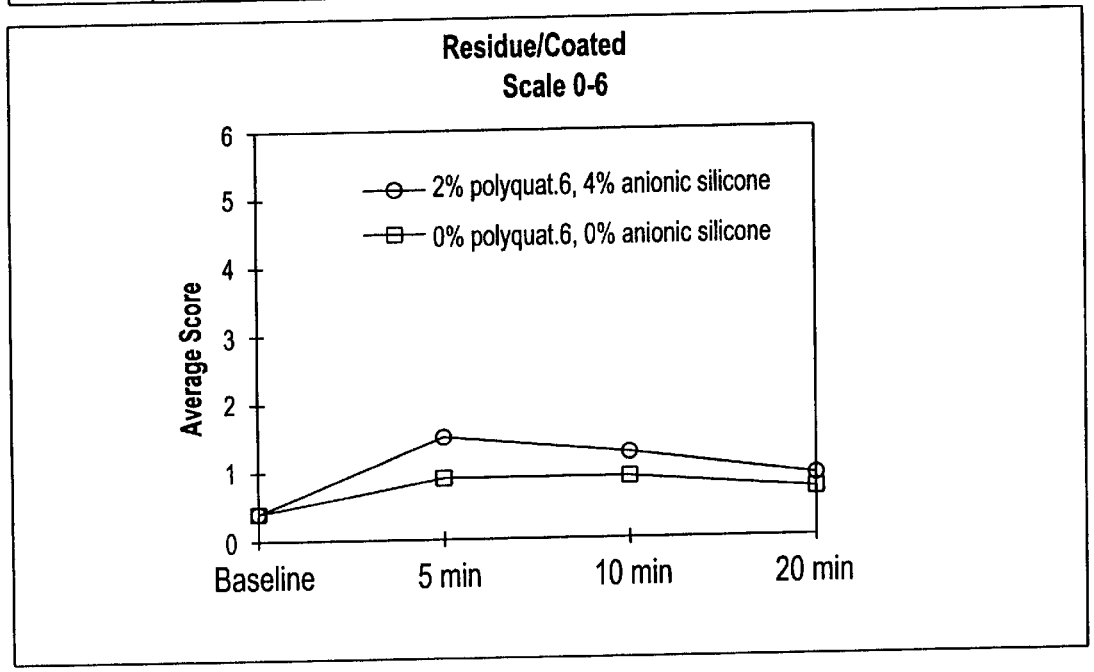

FIG.9F

SENSORY EVALUATION OF COMPLEX (ANIONIC SILICON IN AG BASE)
 4-AUG-97
CONTRASTING HANDWASH FORMULAS: ONE WITH 2% POLYQUAT 6. AND 4% DIMETHICONE COPOLYOL PTHALATE AND ONE WITH 0% POLYQUAT. 6 AND 0% DIMETHICONE COPOLYOL PTHALATE
2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Looks Dry | 2% polyquat.6, 4% anionic silicone | 0.5 | 0.2 | 0.3 | 0.45 |
|  | 0% polyquat.6, 0% anionic silicone | 0.4 | 0.25 | 0.4 | 0.5 |

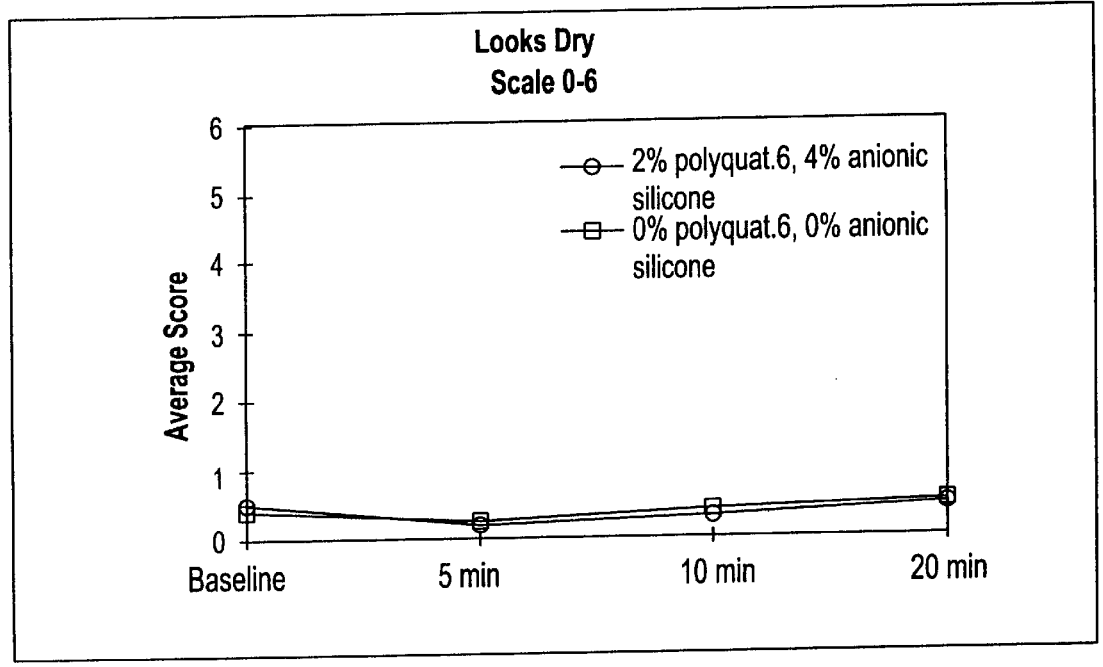

FIG.9G

SENSORY EVALUATION OF COMPLEX (ANIONIC SILICON IN AG BASE)
4-AUG-97
CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE
2% POLYQUAT 6 AND 4% ANIONIC SILICONE, N=10
0% POLYQUAT 6 AND 0% ANIONIC SILICONE, N=10

Average Scores

| Attribute | Product | Baseline | 5 min | 10 min | 20 min |
|---|---|---|---|---|---|
| Feels Dry | 2% polyquat.6, 4% anionic silicone | 0.35 | 0.25 | 0.3 | 0.55 |
| | 0% polyquat.6, 0% anionic silicone | 0.3 | 0.35 | 0.5 | 0.4 |

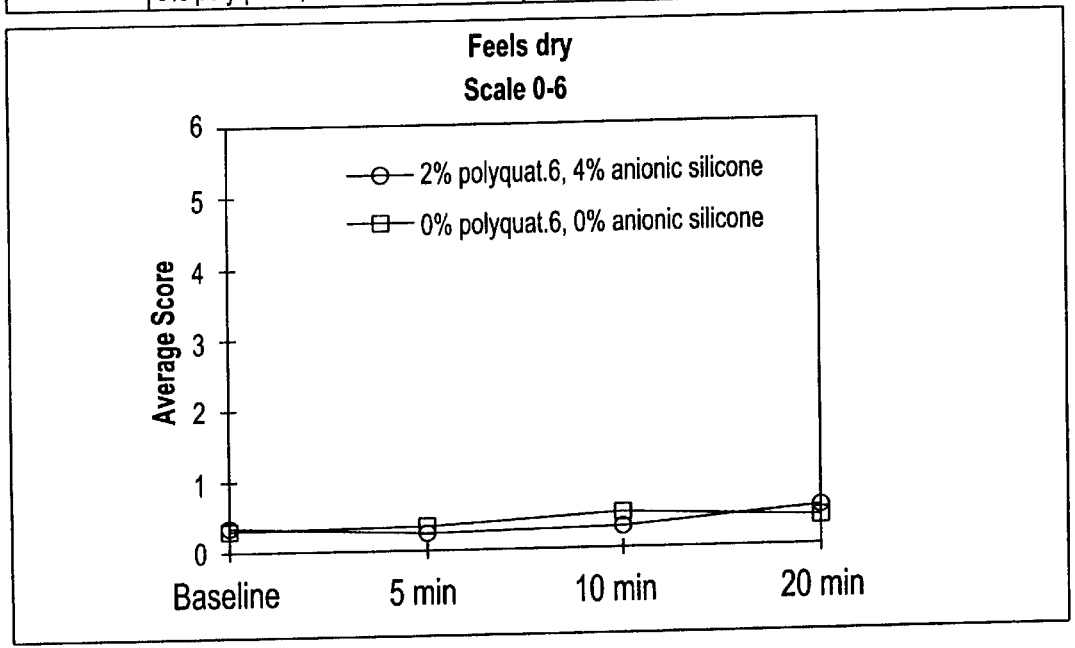

FIG.9H

SENSORY EVALUATION OF COMPLEX (ANIONIC SILICON IN AG BASE)
4-AUG-97

CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Moisturize | 2% polyquat.6, 4% anionic silicone | 0 | 1.05 | 0.95 | 0.65 |
|  | 0% polyquat.6, 0% anionic silicone | 0 | 0.35 | 0.5 | 0.35 |

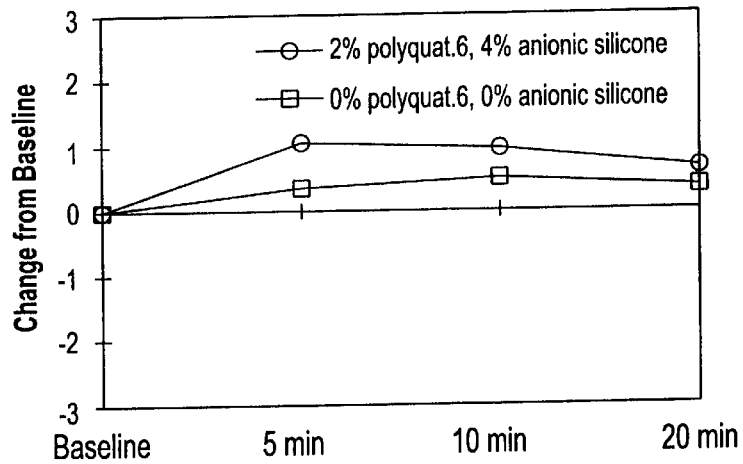

FIG. 91

SENSORY EVALUATION OF COMPLEX (ANIONIC SILICON IN AG BASE)
4-AUG-97
CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Plump / Hy | 2% polyquat.6, 4% anionic silicone | 0 | 1 | 0.6 | 0.5 |
|  | 0% polyquat.6, 0% anionic silicone | 0 | 0.45 | 0.45 | 0.25 |

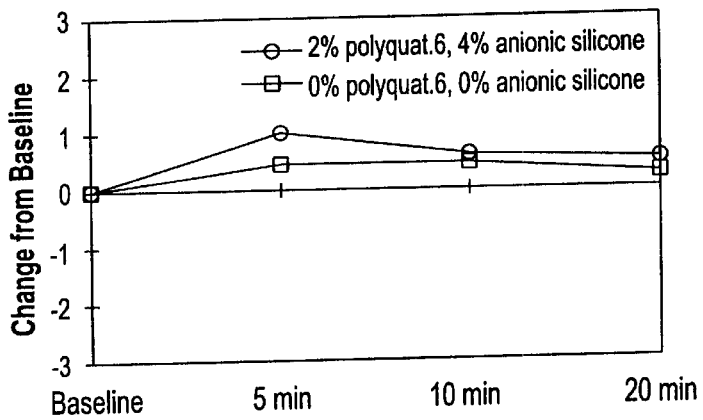

FIG. 9J

SENSORY EVALUATION OF COMPLEX (ANIONIC SILICON IN AG BASE)
4-AUG-97
CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Smooth | 2% polyquat.6, 4% anionic silicone | 0 | 0.5 | 1.4 | 1.05 |
|  | 0% polyquat.6, 0% anionic silicone | 0 | 0.35 | 1.05 | 0.85 |

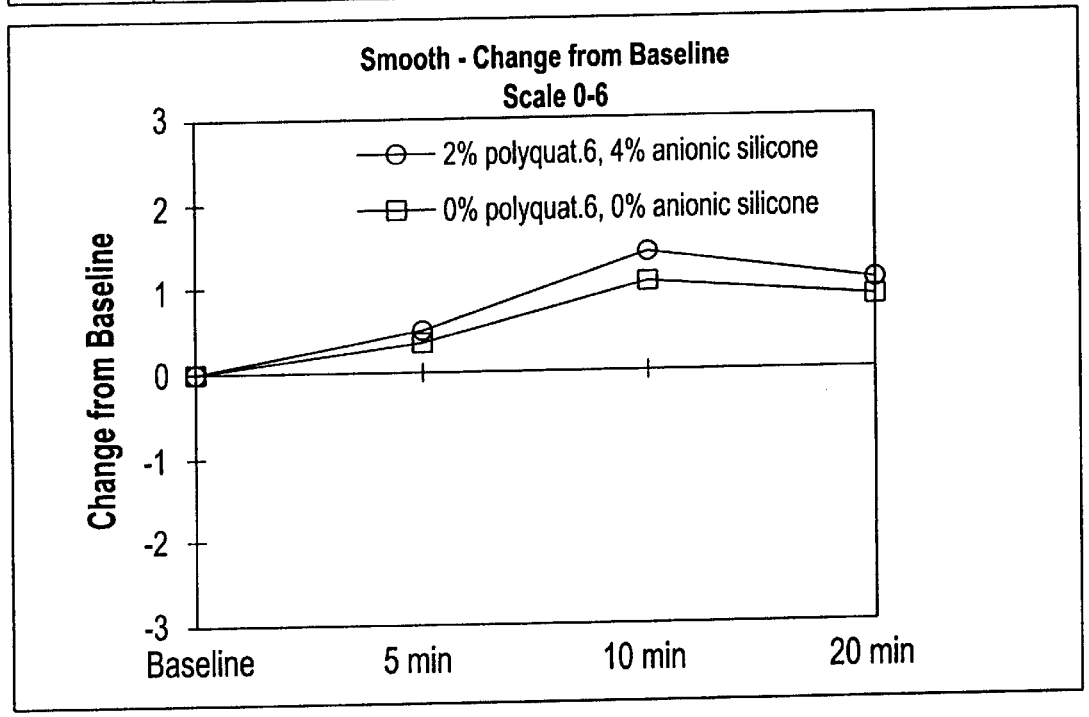

FIG.9K

SENSORY EVALUATION OF COMPLEX (ANIONIC SILICON IN AG BASE)
4-AUG-97
CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Soft | 2% polyquat.6, 4% anionic silicone | 0 | 0.95 | 0.95 | 0.75 |
|  | 0% polyquat.6, 0% anionic silicone | 0 | 0.65 | 0.5 | 0.25 |

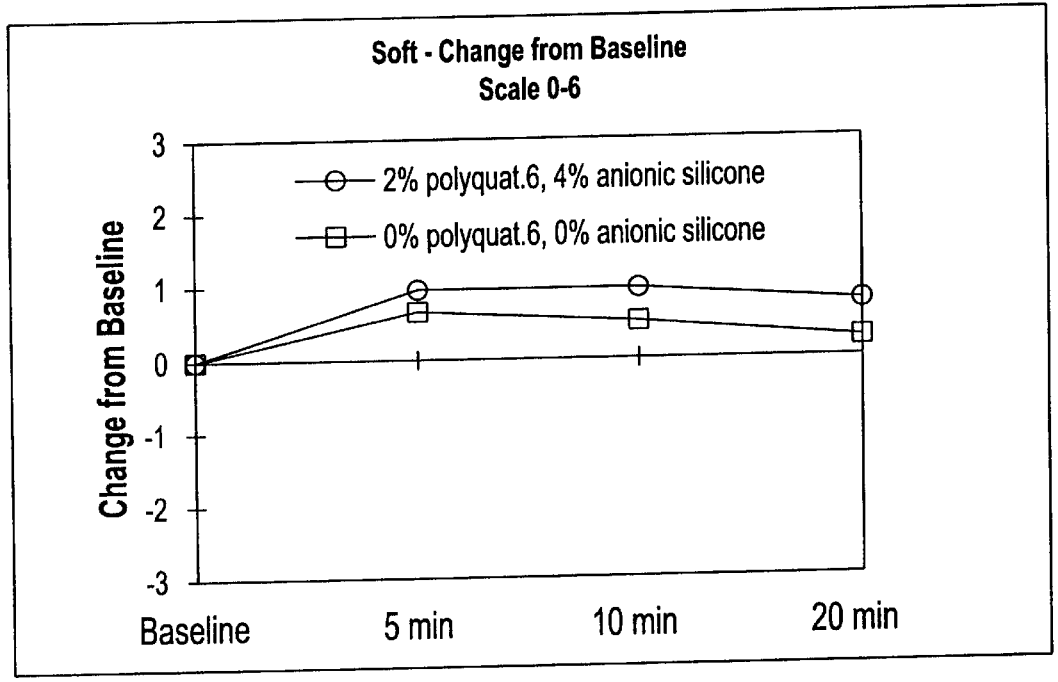

FIG.9L

SENSORY EVALUATION OF COMPLEX (ANIONIC SILICON IN AG BASE)
4-AUG-97
CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Tight | 2% polyquat.6, 4% anionic silicone | 0 | 0 | 0.15 | 0.25 |
| | 0% polyquat.6, 0% anionic silicone | 0 | 0.15 | 0.3 | 0.3 |

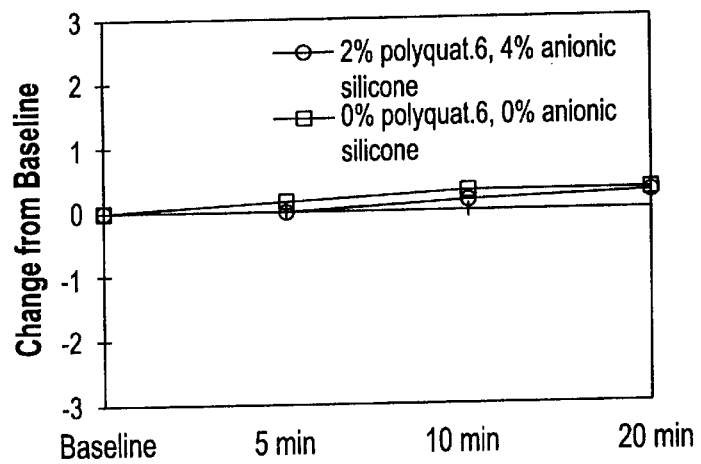

FIG.9M

SENSORY EVALUATION OF COMPLEX (ANIONIC SILICON IN AG BASE)
4-AUG-97
CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Residue/Coated | 2% polyquat.6, 4% anionic silicone | 0 | 1.1 | 0.85 | 0.5 |
| | 0% polyquat.6, 0% anionic silicone | 0 | 0.5 | 0.5 | 0.3 |

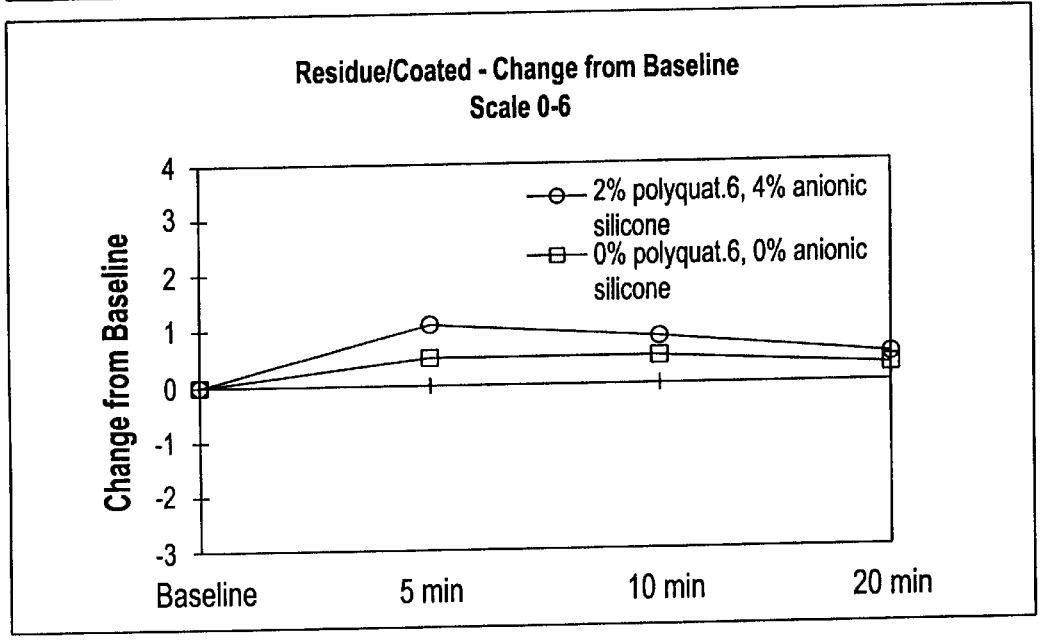

FIG.9N

SENSORY EVALUATION OF COMPLEX (ANIONIC SILICON IN AG BASE)
4-AUG-97

CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Looks Dry | 2% polyquat.6, 4% anionic silicone | 0 | -0.3 | -0.2 | -0.05 |
|  | 0% polyquat.6, 0% anionic silicone | 0 | -0.15 | 0 | 0.1 |

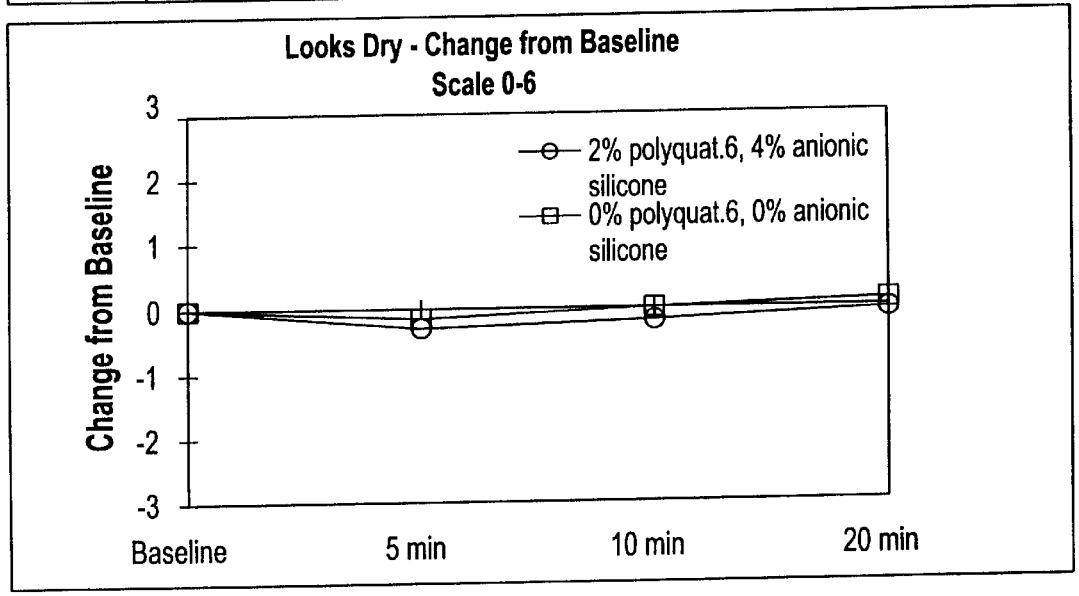

FIG.90

SENSORY EVALUATION OF COMPLEX (ANIONIC SILICON IN AG BASE)
4-AUG-97
CONTRASTING HANDWASH FORMULAS: ONE WITH 2% POLYQUAT. 6 AND 4% DIMETHICONE COPOLYOL PTHALATE AND ONE WITH 0% POLYQUAT. 6 AND 0% DIMETHICONE COPOLYOL PTHALATE

2% POLYQUAT 6 AND 4% ANIONIC SILICONE, N=10
0% POLYQUAT 6 AND 0% ANIONIC SILICONE, N=10

Change from Baseline

| Attribute | Product | Baseline | 5 min | 10 min | 20 min |
|---|---|---|---|---|---|
| Feels Dry | 2% polyquat.6, 4% anionic silicone | 0 | -0.1 | -0.05 | 0.2 |
| | 0% polyquat.6, 0% anionic silicone | 0 | 0.05 | 0.2 | 0.1 |

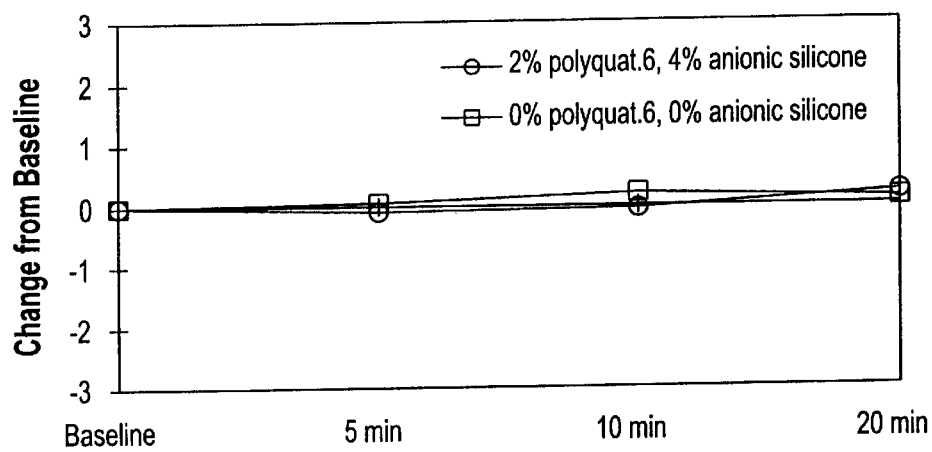

FIG.9P

ANIONIC/CATIONIC MOISTURIZING COMPLEX

FIELD OF THE INVENTION

This invention pertains to improved personal cleansing compositions which have superior skin conditioning properties. The compositions may be in the form of a liquid or gel, such as hand washes and the like, or in the form of a bar soap, or for shower and bath application or conditioning shampoo. The inventive compositions leave skin with improved softness, moisturizing, smoothness and hydration and hair in an improved condition.

BACKGROUND OF THE INVENTION

A wide variety of products are commonly available as skin conditioners. These compositions comprise one or more emollients, or skin conditioners, in a vehicle. The vehicle is typically optimized to provide for a method of depositing or contacting the skin with the emollient. More recently, these products have taken the form of hand and body washes and the like. A superior example of this type of product, where the vehicle is improved by careful control of the surfactant content is disclosed in U.S. patent application Ser. No. 08/861,108. It remains difficult, however, to provide a formulation which can be applied in an environment of high water dilution, such as a shower or bath, as well as directly on the skin followed by rinsing, and achieve significant improvements in skin conditioning.

SUMMARY OF THE INVENTION

The invention comprises a personal body or handwash formula that offers superior skin conditioning properties. It can be in the form of a liquid or a gel, bath beads or in the form of a soap bar. It may also be in the form of a conditioning shampoo. The conditioning agents are a combination of a highly charged cationic polymer, and an anionic emollient. The emollient can be either an anionic oil, or anionic silicone oil. Preferred species include polyquaternium 6 (Polyquat 6) as the cationic polymer, and sulfated castor oil (SCO) as the anionic emollient. The polymer can be present in a range of 0.5%–10% by weight, and the anionic emollient should be present in amounts of 1%–30% by weight, although lower levels up to 10% are effective and preferred. All percentages given herein are in terms of active weight %, unless indicated otherwise.

The composition may contain other agents that do not interfere with the ability of the cationic polymer and the anionic emollient to form a sparingly soluble complex. While applicants do not wish to be bound to this theory, it is believed that this sparingly soluble complex is forced out of solution when diluted, and is deposited on the skin during use. The complex is rather more difficult to remove and effective in skin conditioning, than the emollient alone.

BRIEF DESCRIPTION OF THE DRAWINGS

Each of FIGS. 1A–P through 9A–P is a graphical illustration of a comparative study of two compositions each. Each pair of compositions is tested for eight characteristics: moisturizing, hydrating, smooth, soft, tight, residue, looks dry and feels dry. Clearly, all eight are not independent variables. In graphs A–H of each pair, the values are measured for the two tested compositions. In graphs I–P, the values obtained are compared against the baseline values (values obtained prior to treatment). All percentages are by weight.

FIGS. 5A–P contrast an inventive composition, with polyquat 6 (2%) and dimethicone copolyol phthalate (DCP) (4%) as compared with a control, which has no polyquat 6 or DCP.

FIGS. 6A–P compare the performance of a composition outside the invention, a composition that contains 2% polyquat 6 and 4% isopropyl PPG-2-isodeceth-7 carboxylate (an anionic ester) compared with a control containing no polyquat 6 or anionic emollient.

FIG. 9 compare an inventive hand wash, polyquat 6 (2%) and DCP (4%) as compared to a control with no polyquat 6 or DCP.

DETAILED DESCRIPTION OF THE INVENTION

Figure 1A:
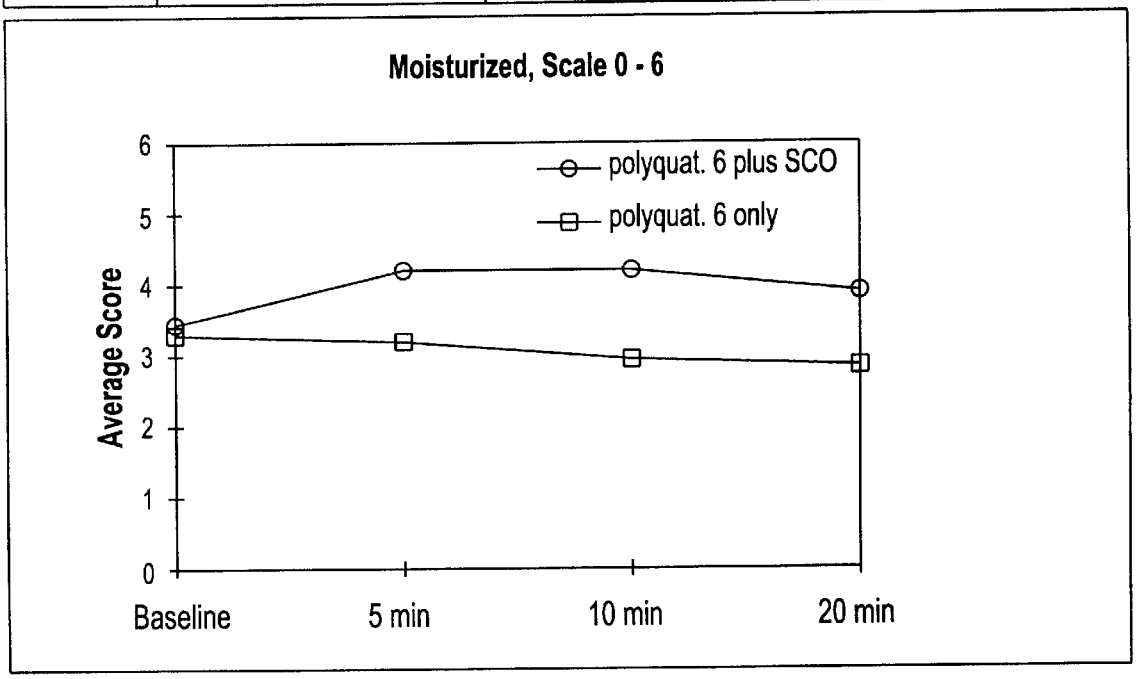
FIGS. 1A–P measure a formulation comprising polyquat 6 (2%) and SCO (4%) against polyquat 6 (2%) alone, as a control.
Figure 1B:
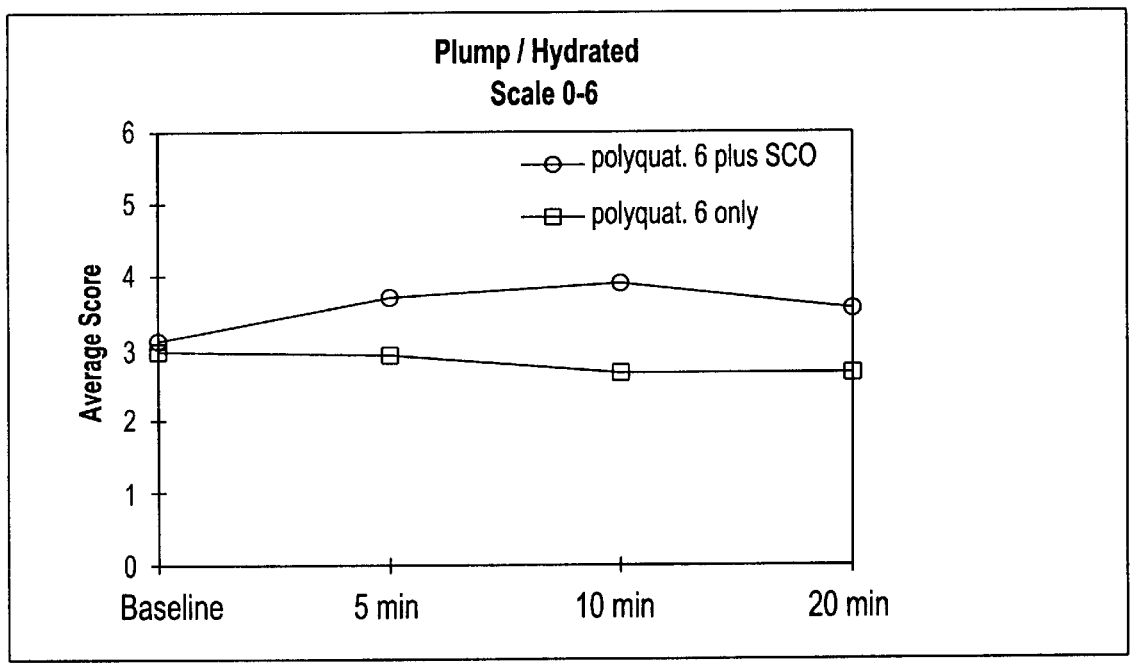
Figure 1C:
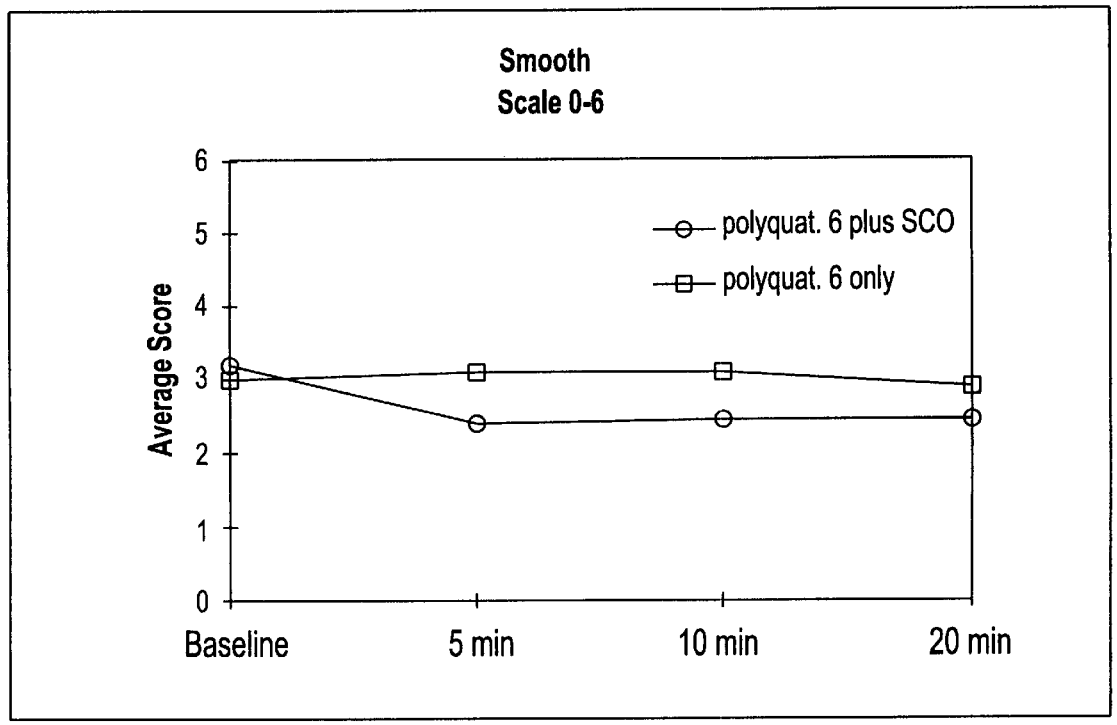
Figure 1D:
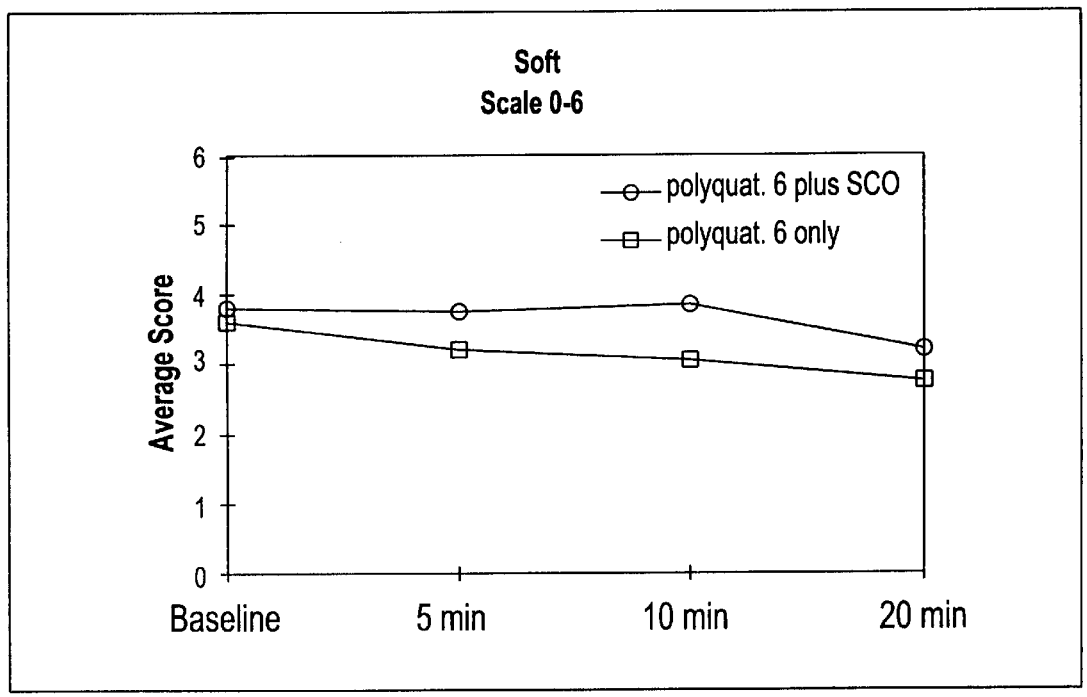
Figure 1E:
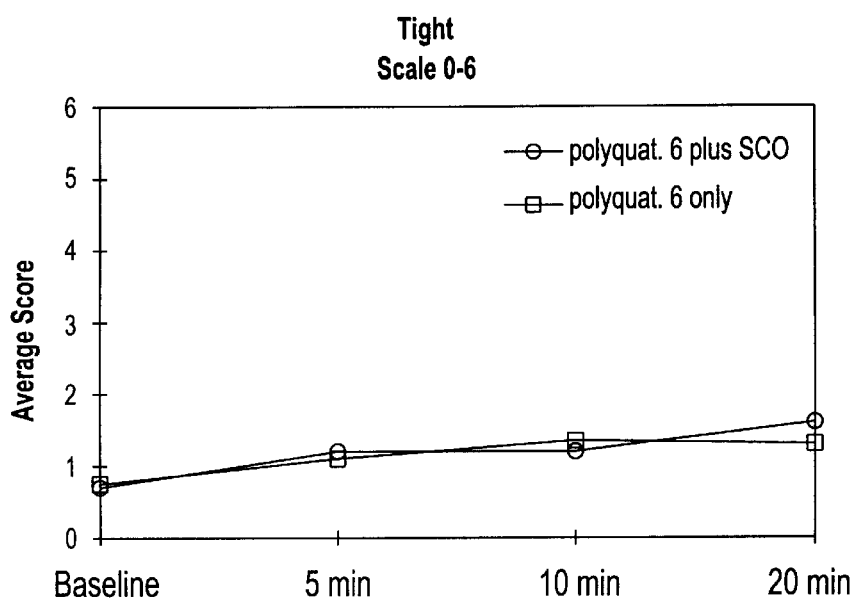
Figure 1F:
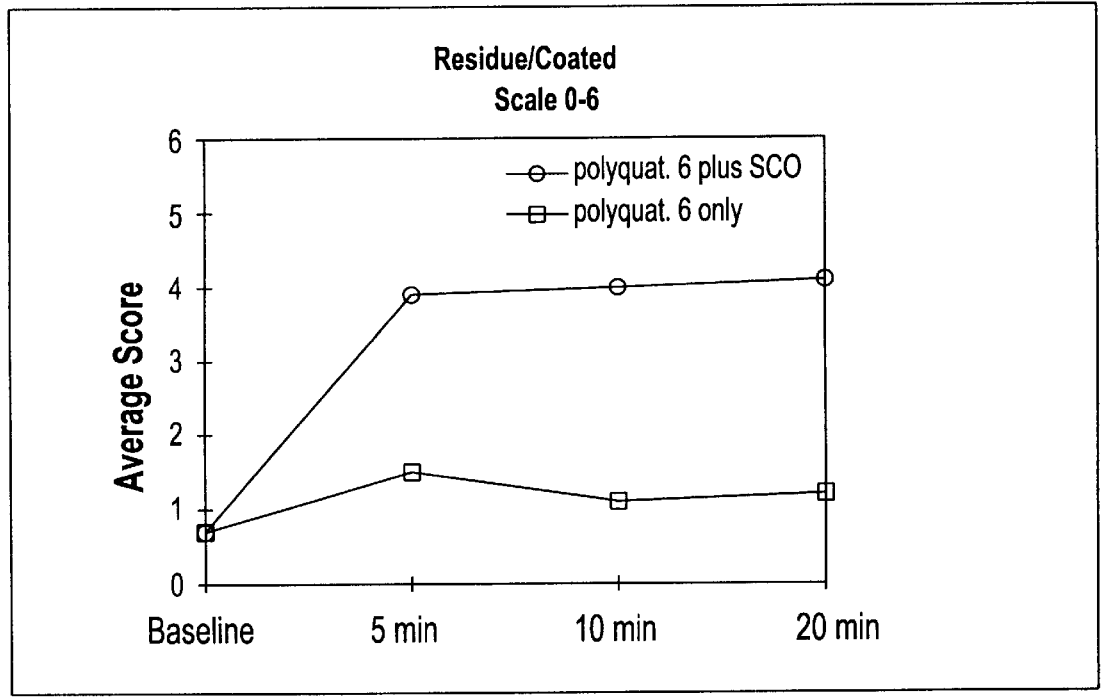
Figure 1G:
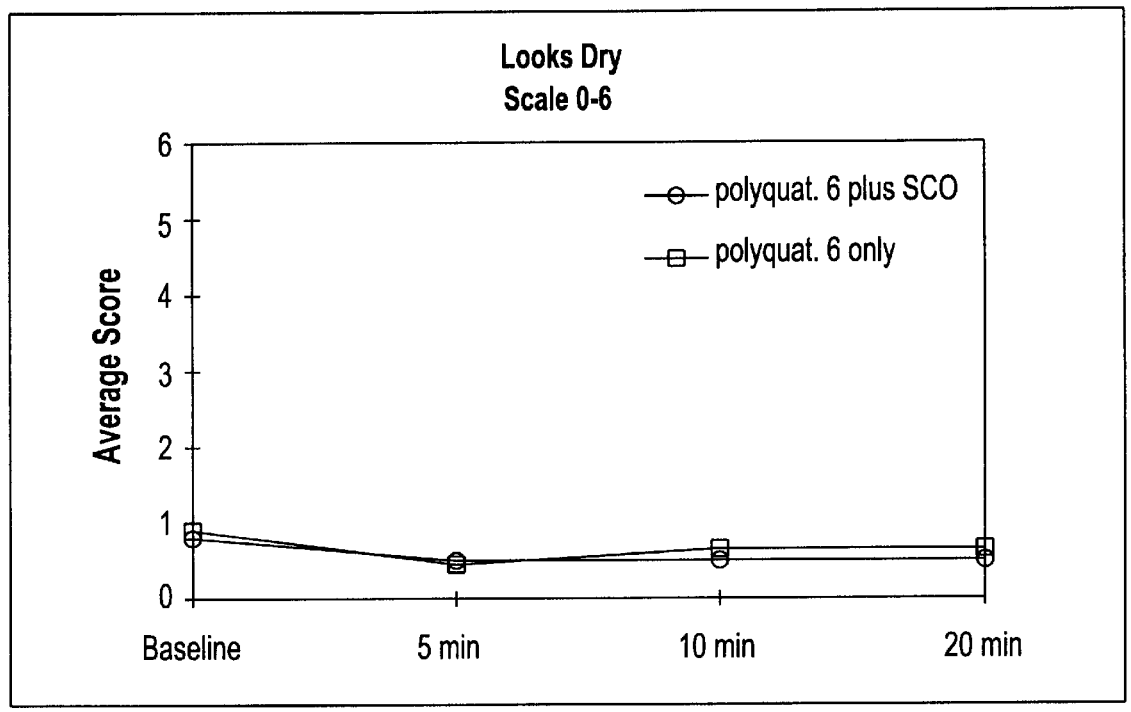
Figure 1H:
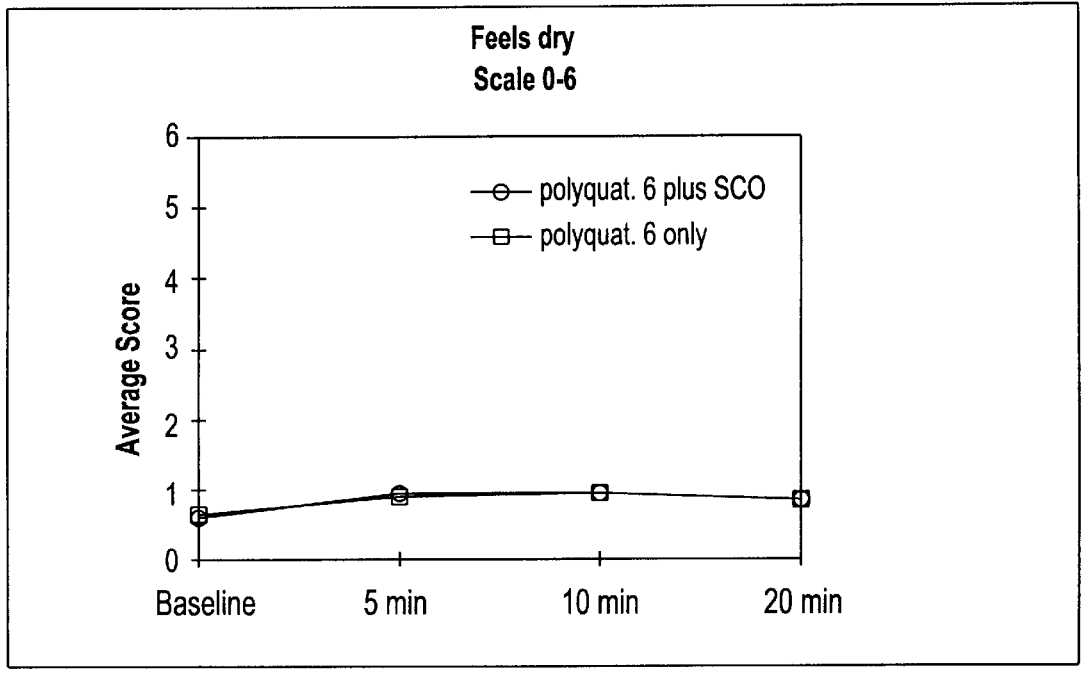
Figure 1I:
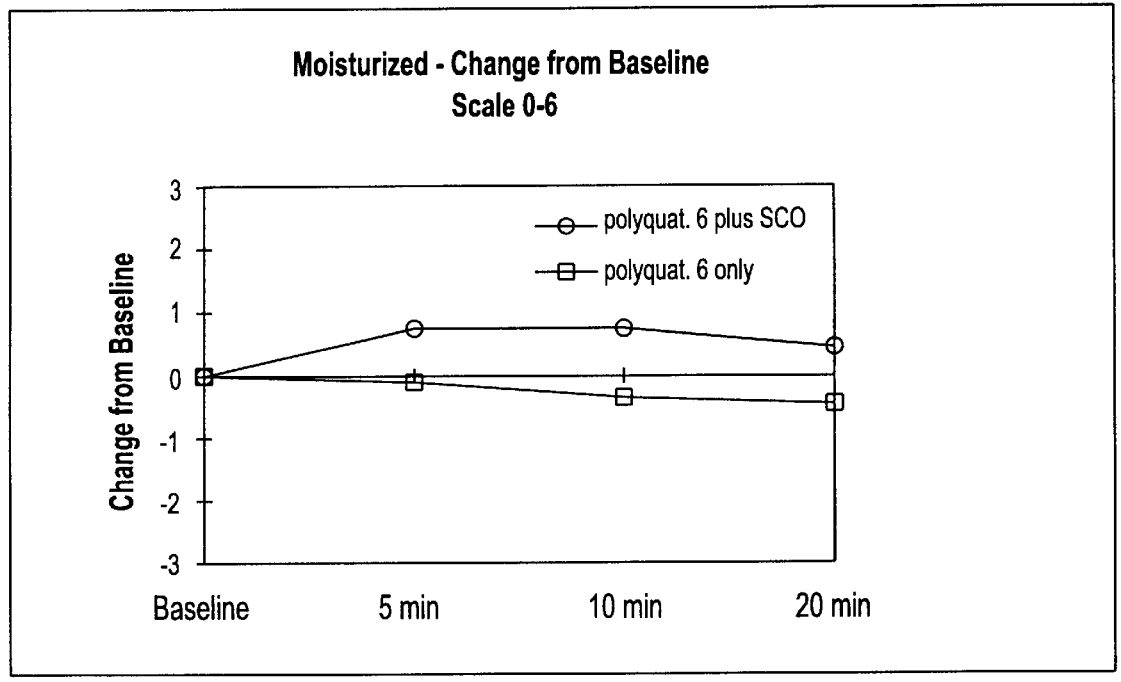
Figure 1J:
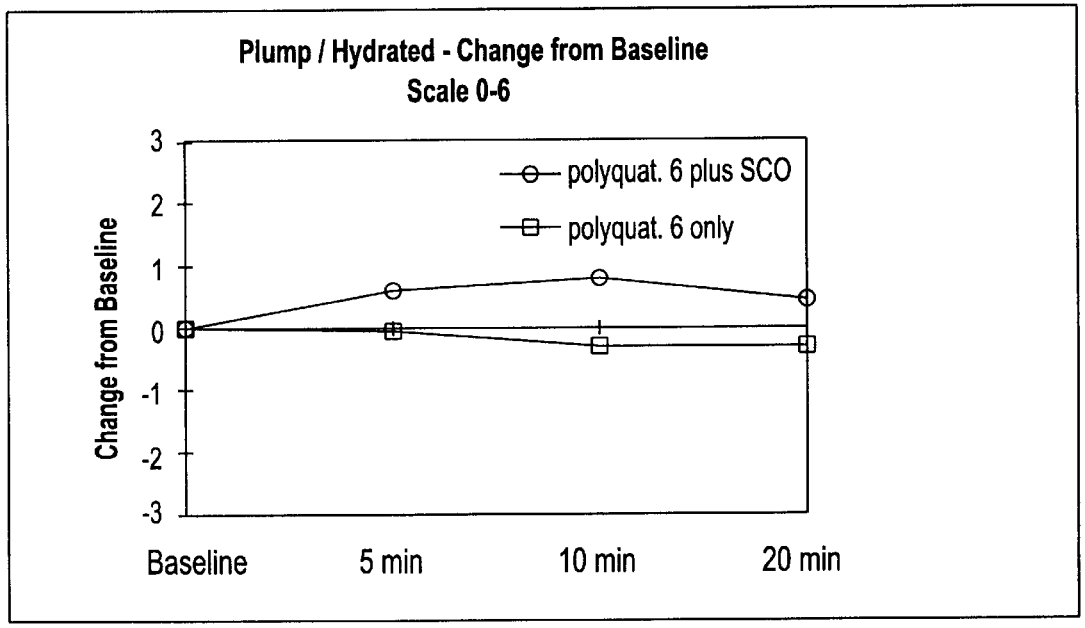
Figure 1K:
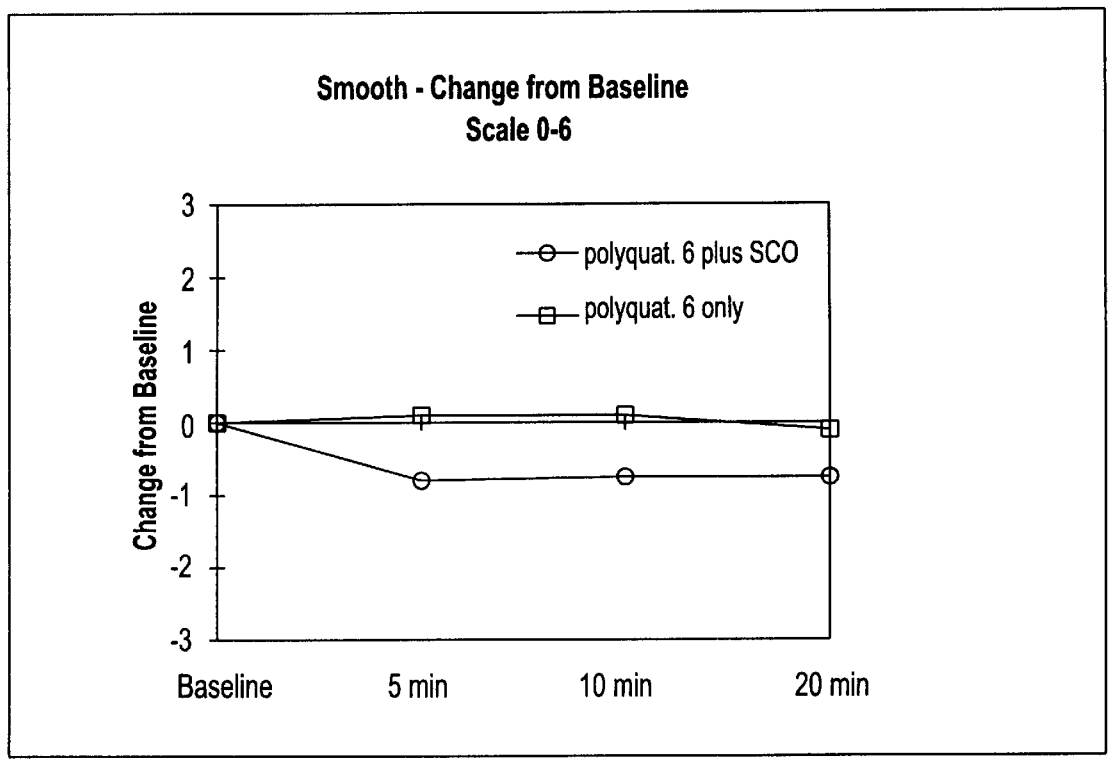
Figure 1L:
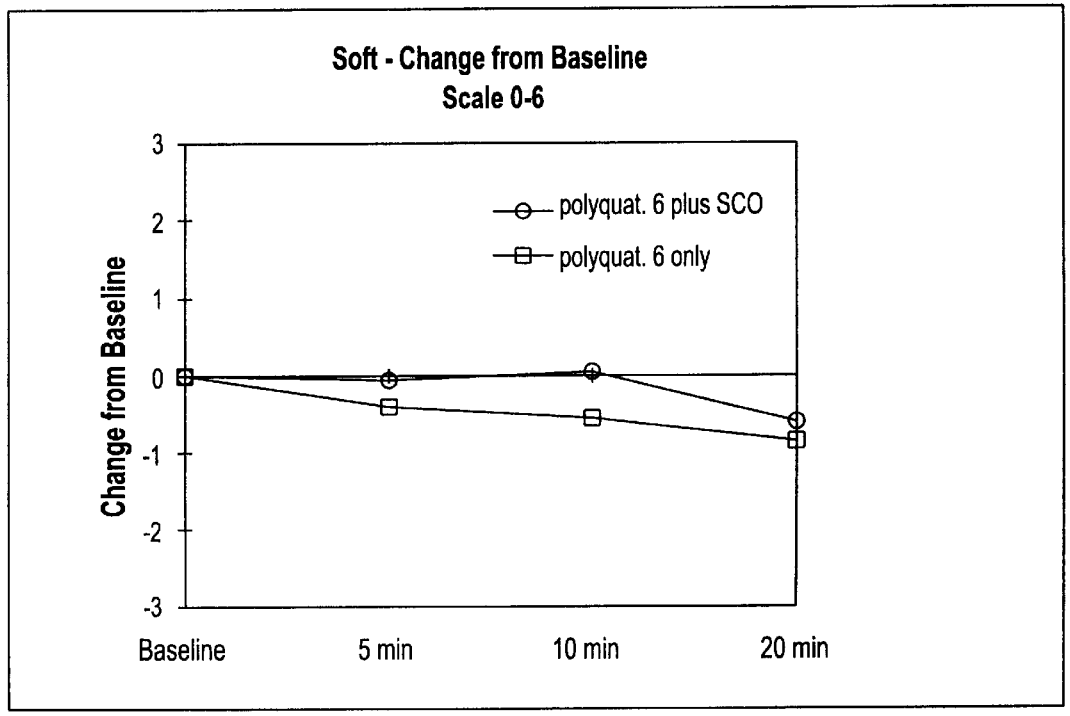
Figure 1M:
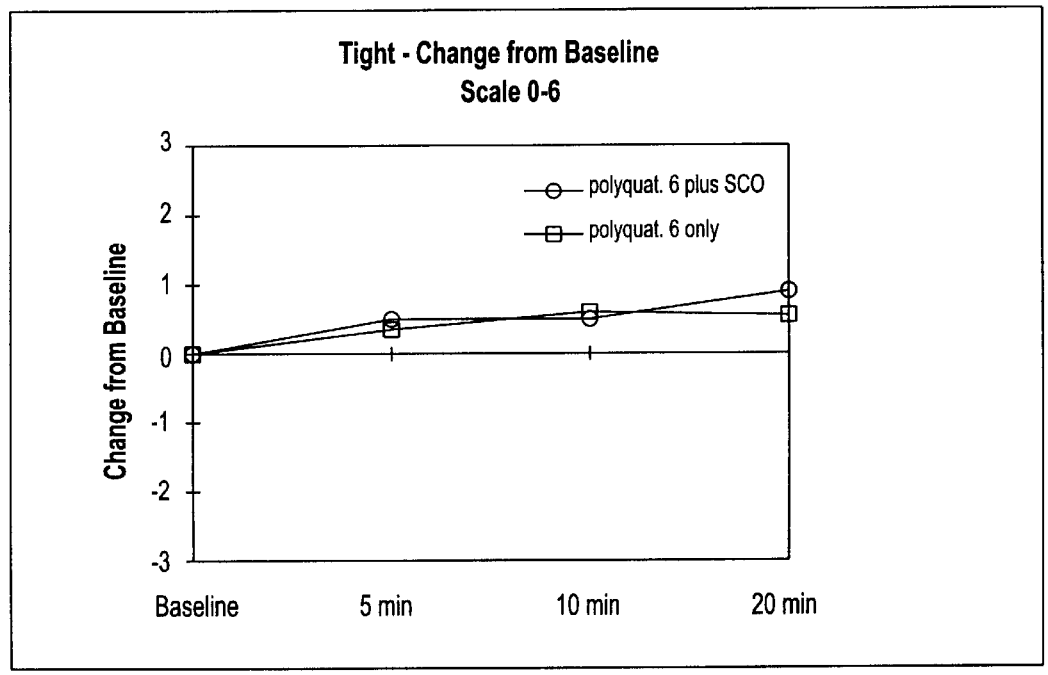
Figure 1N:
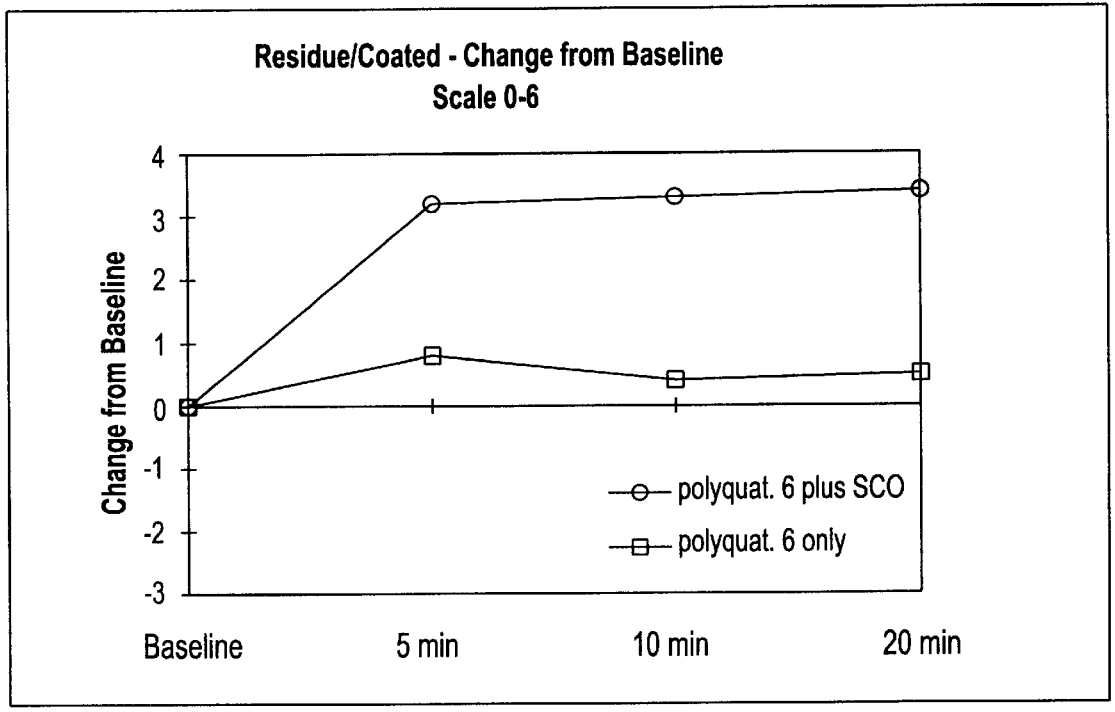
Figure 10:
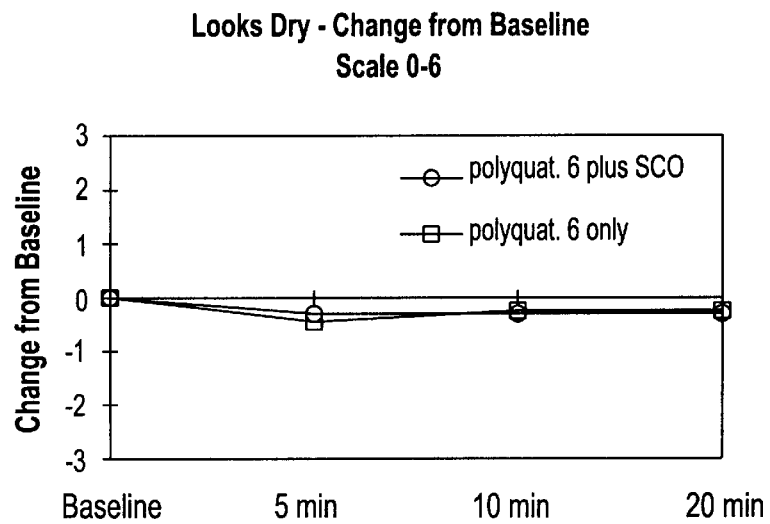
Figure 1P:
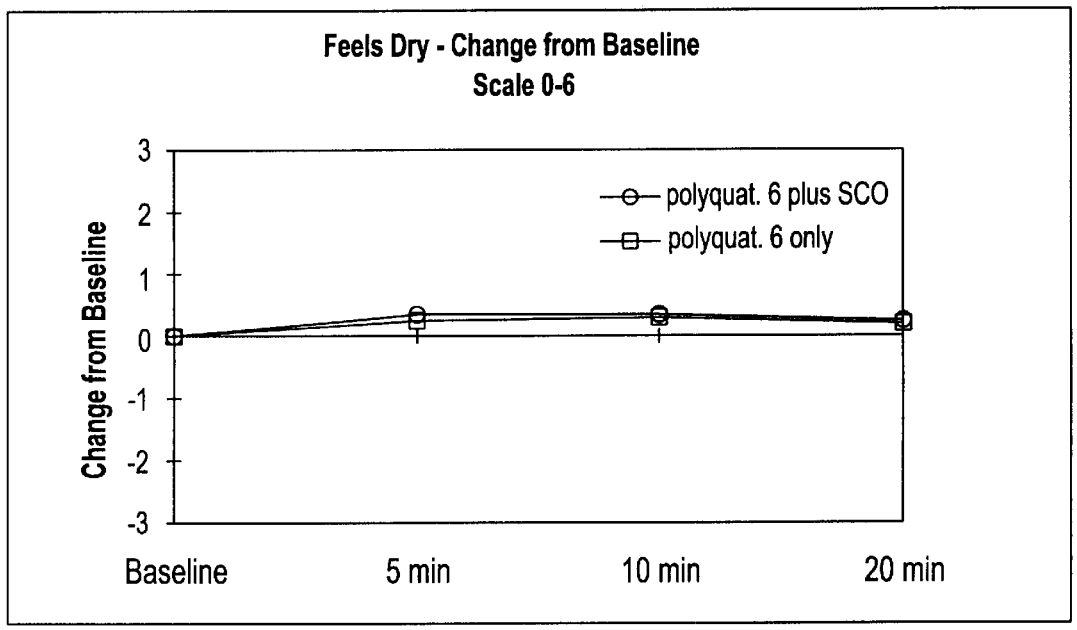
Figure 2A:
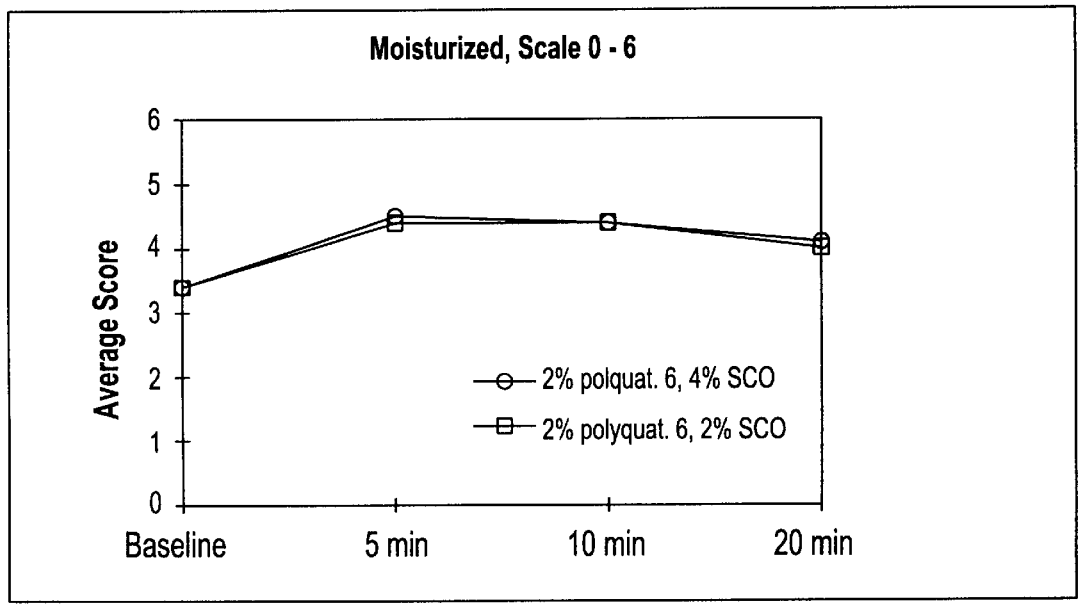
FIGS. 2A–P contrast two formulations within the claimed invention, one comprising polyquat 6 (2%) and SCO (4%) as opposed to polyquat 6 (2%) and SCO (2%).
Figure 2B:
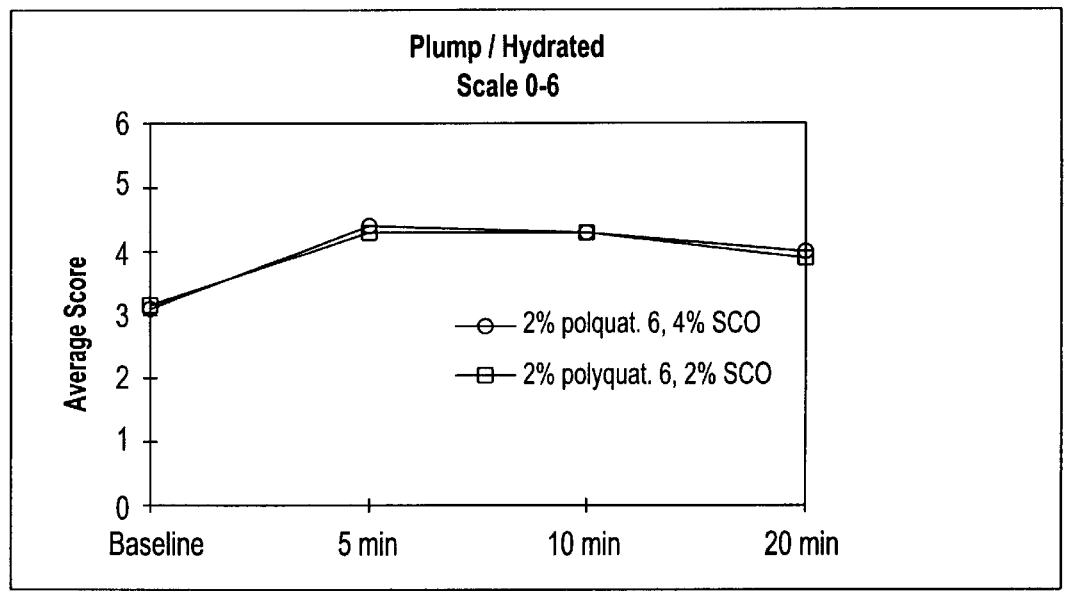
Figure 2C:
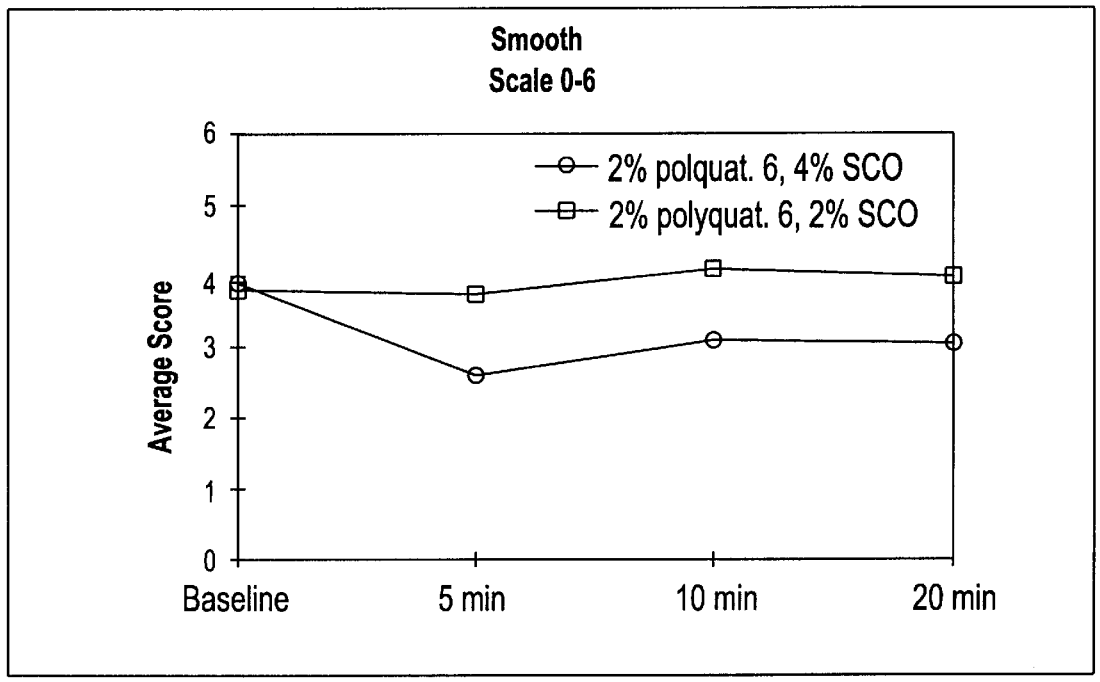
Figure 2D:
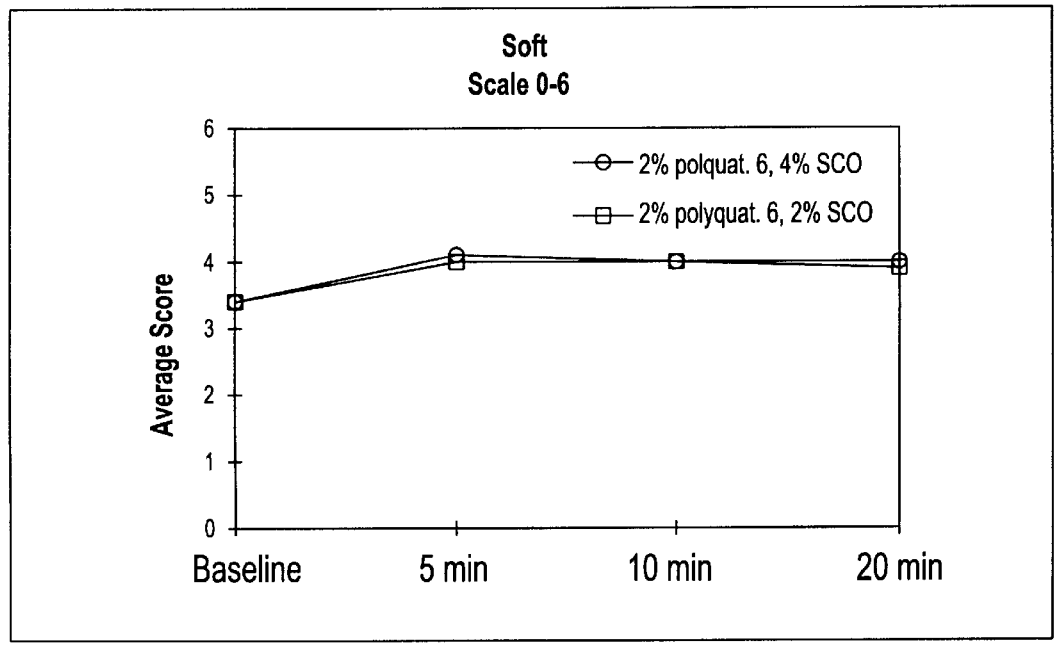
Figure 2E:
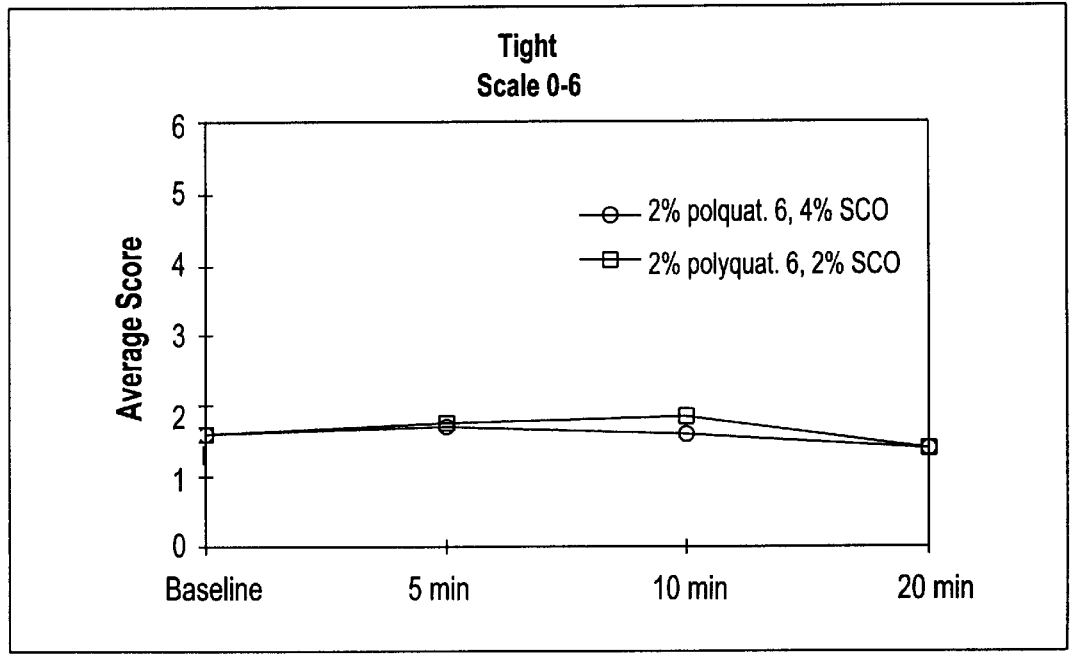
Figure 2F:
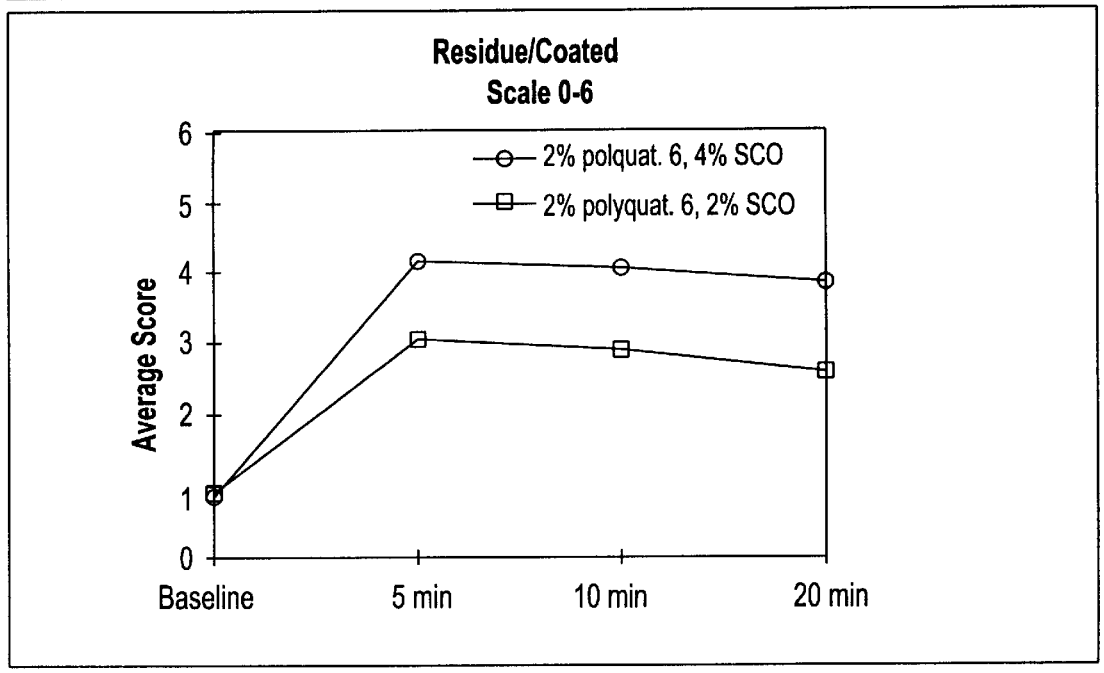
Figure 2G:
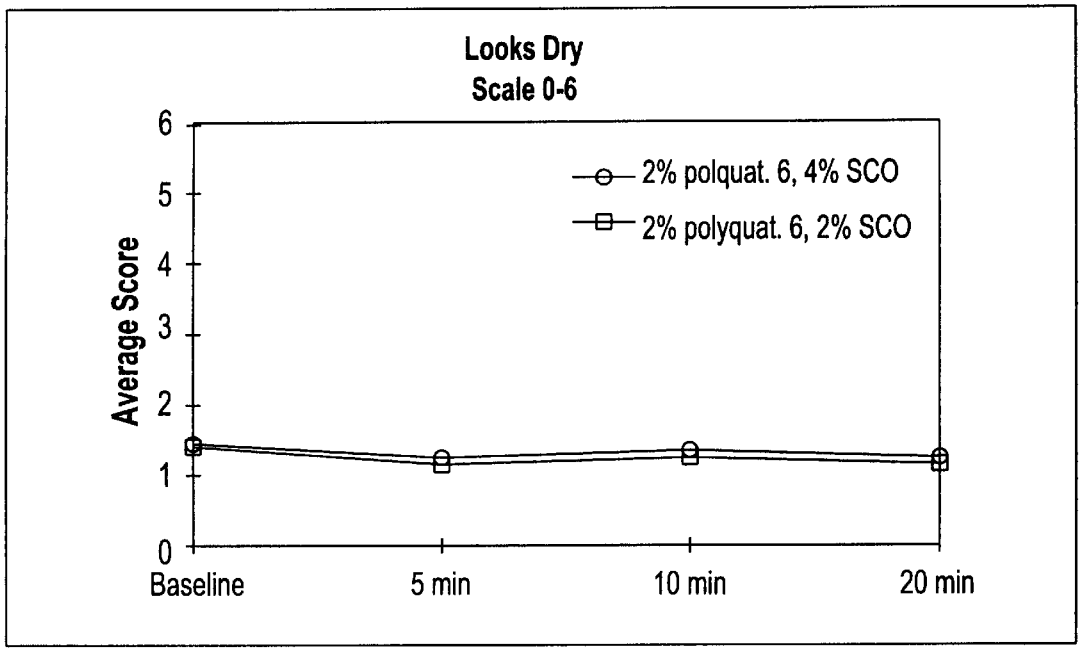
Figure 2H:
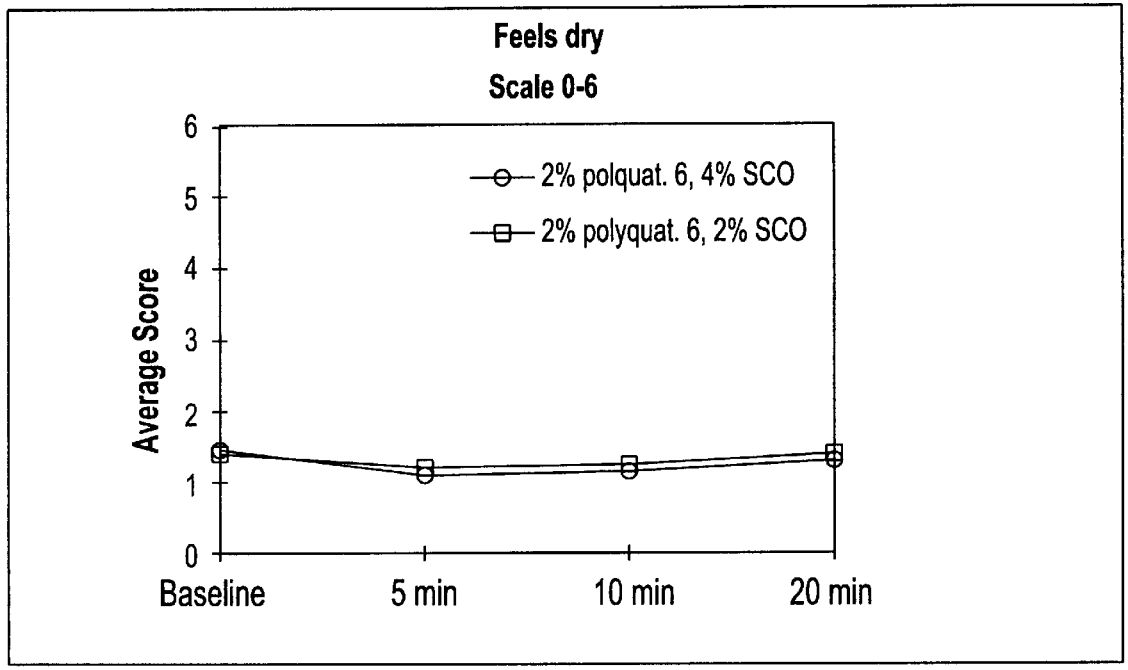
Figure 21:
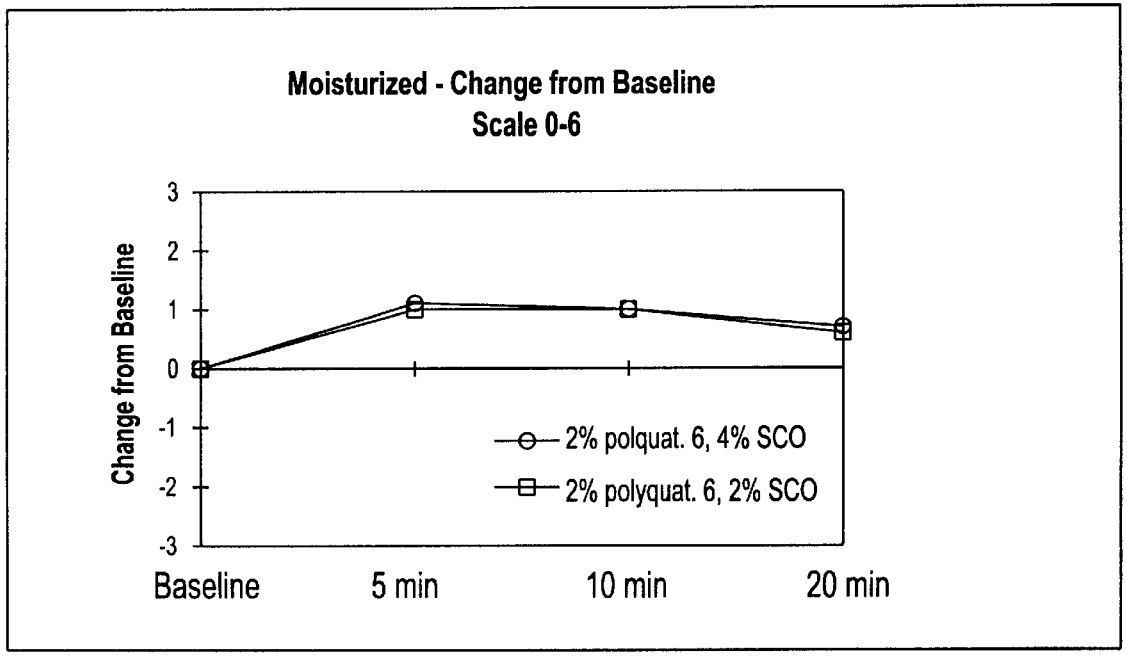
Figure 2J:
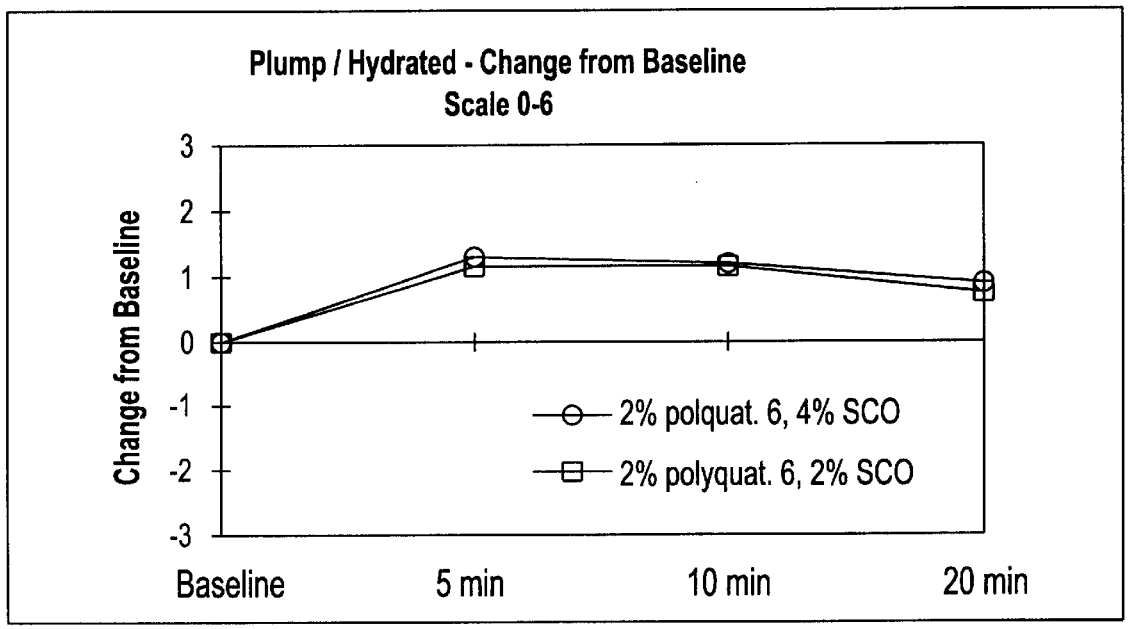
Figure 2K:
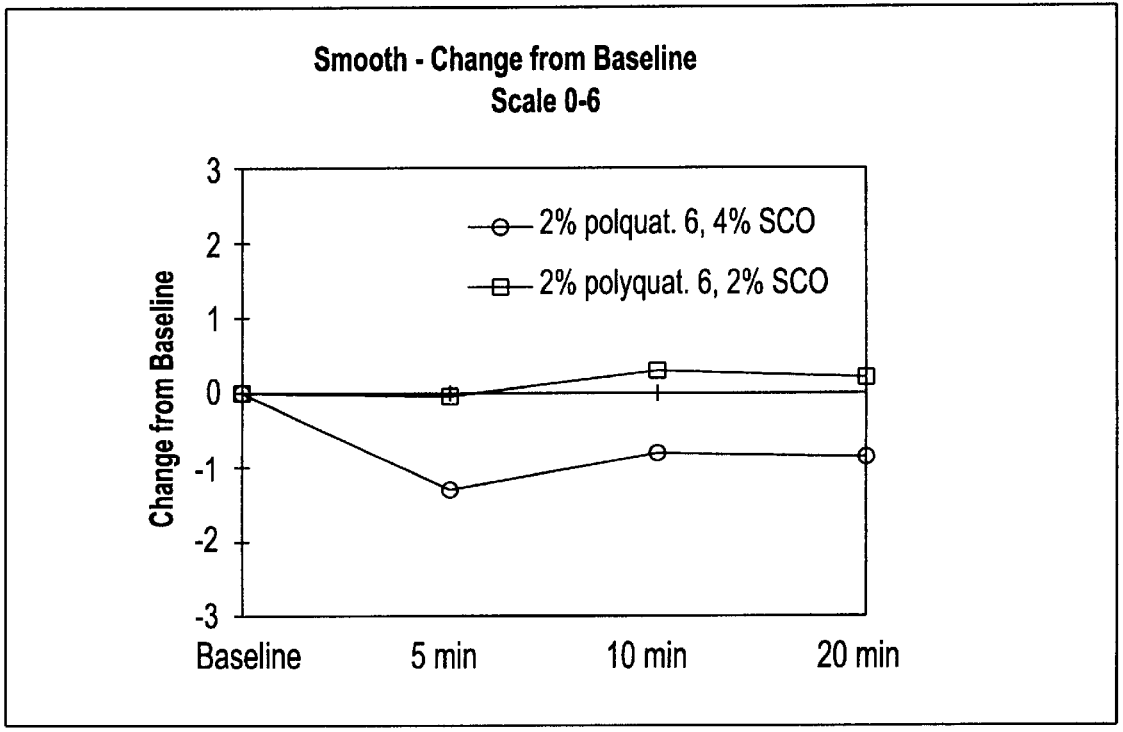
Figure 2L:
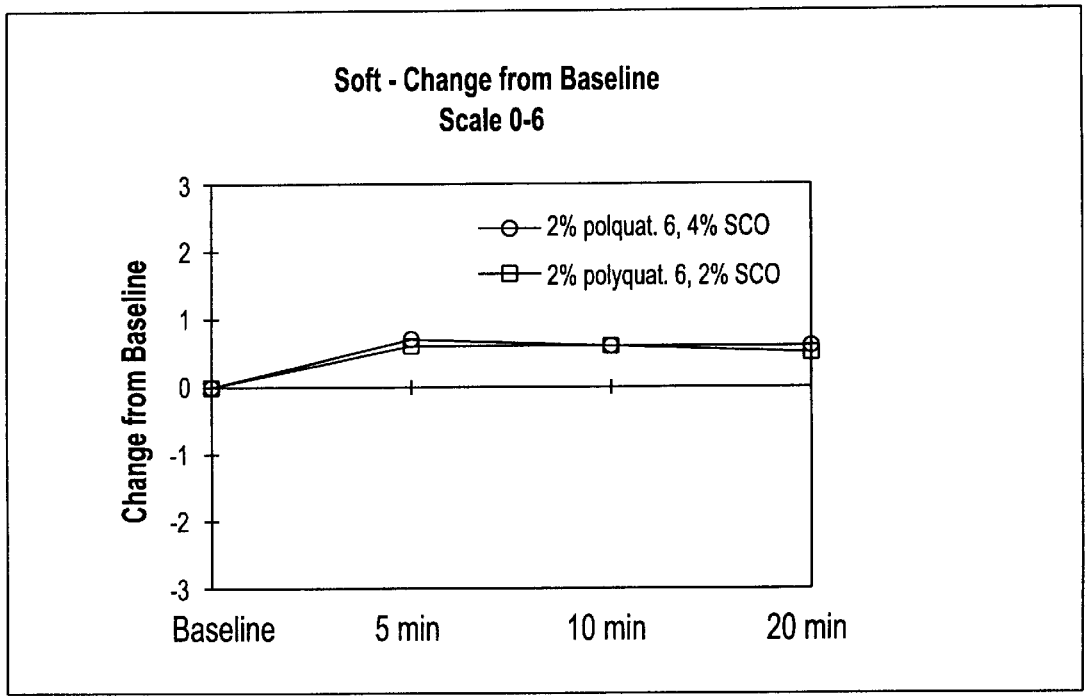
Figure 2M:
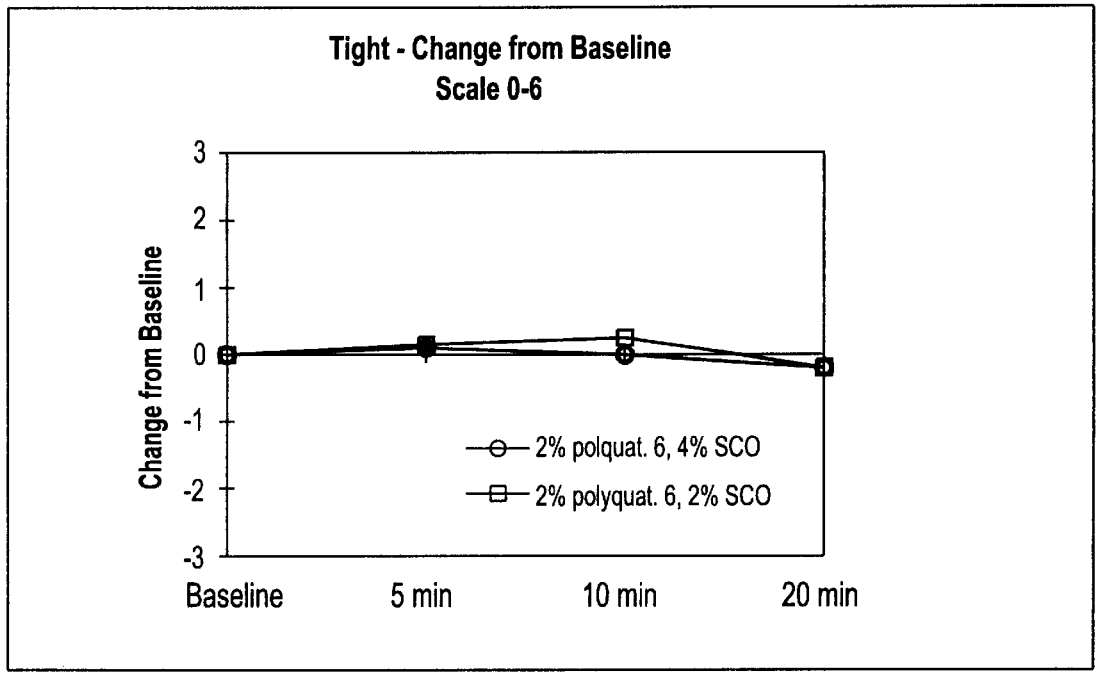
Figure 2N:
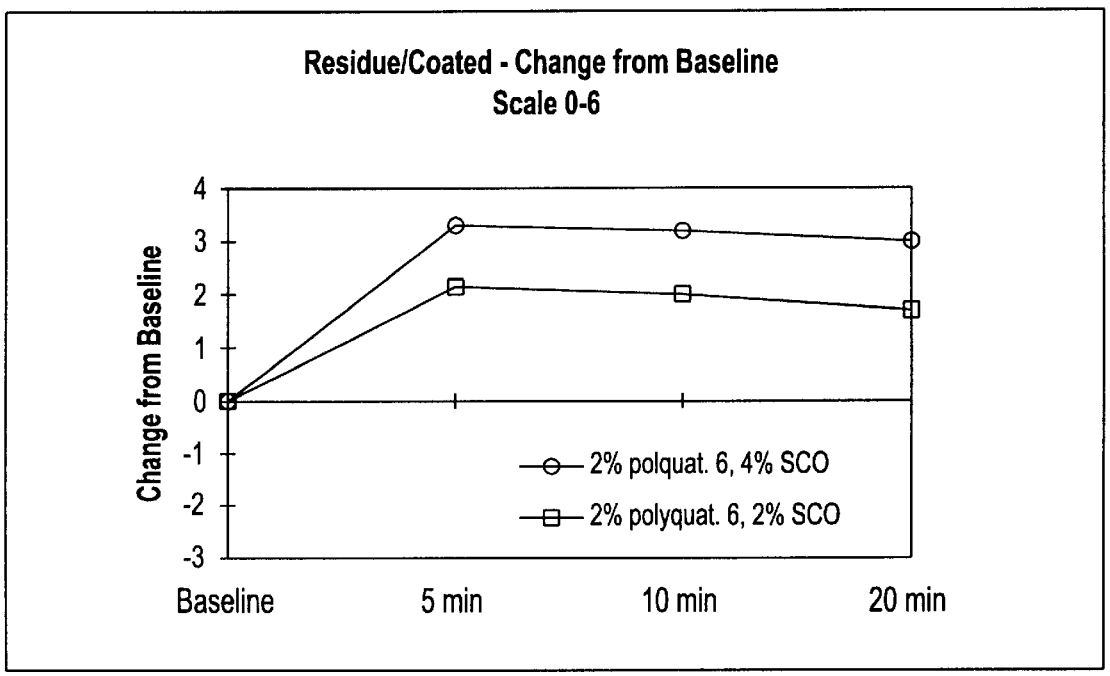
Figure 20:
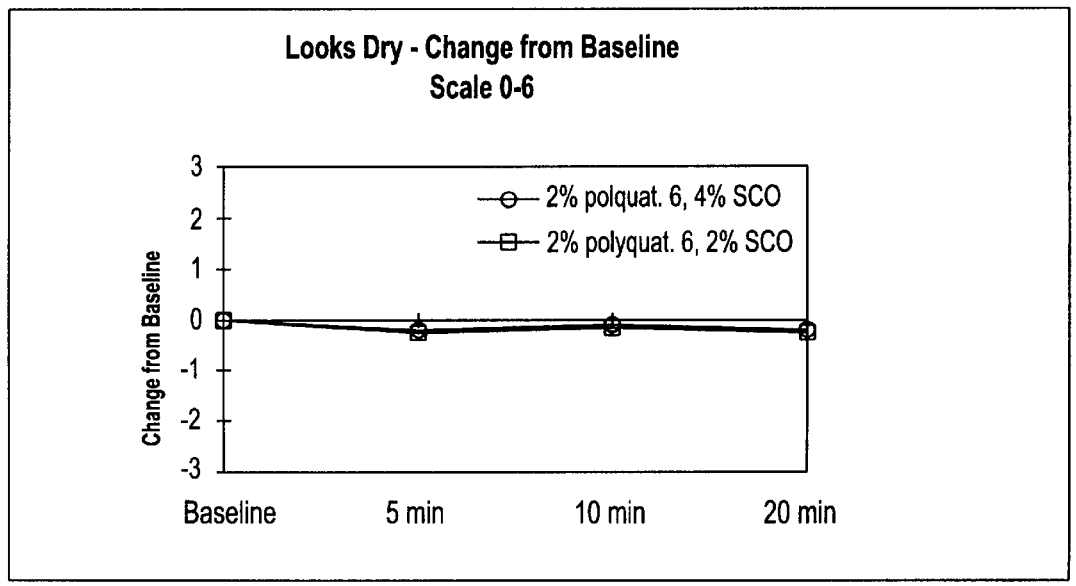
Figure 2P:
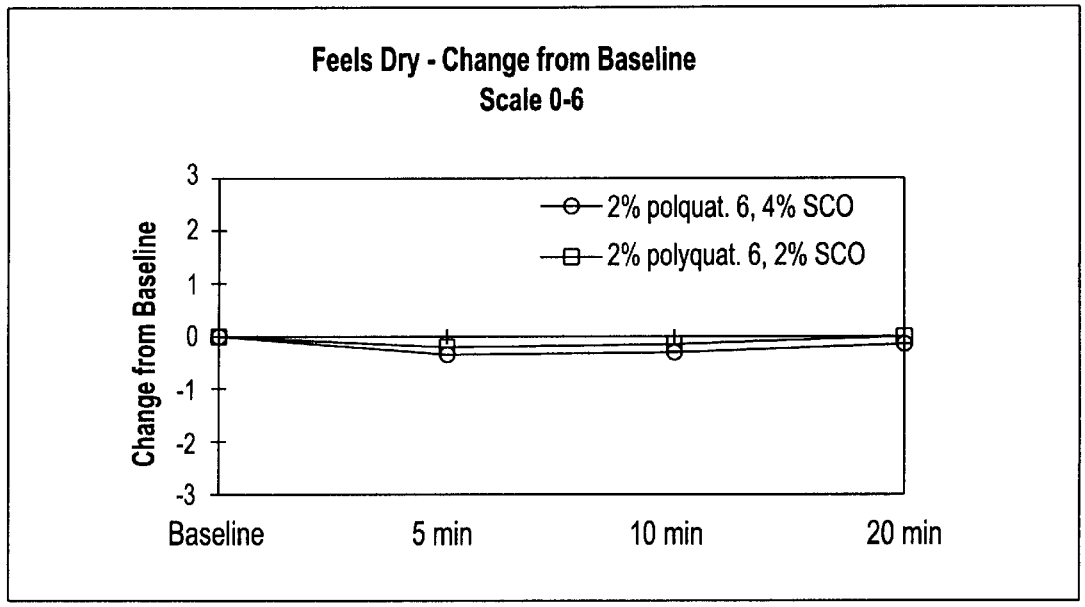
Figure 3A:
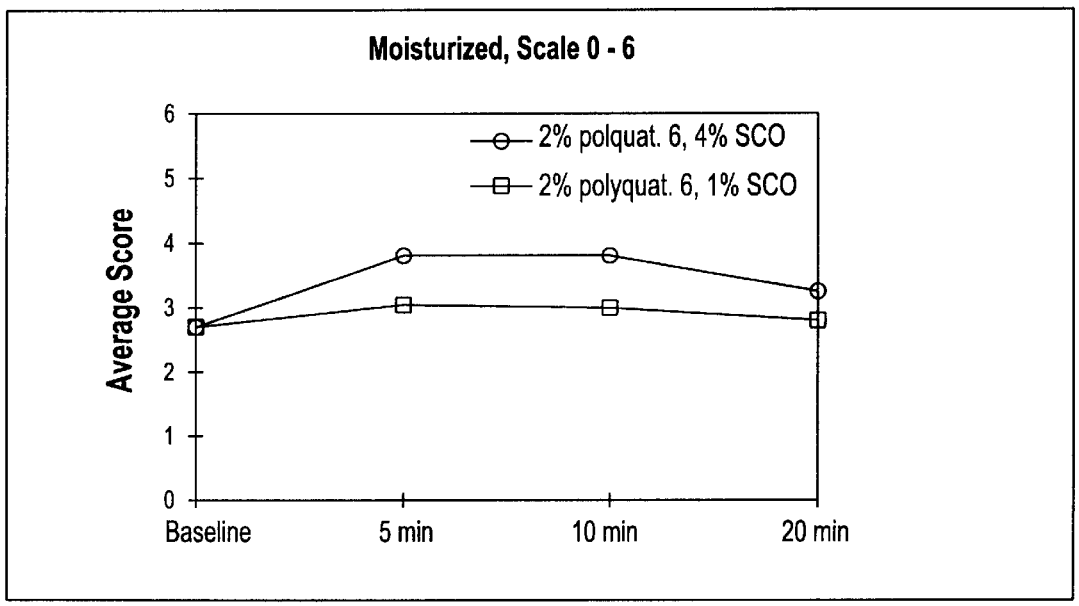
FIGS. 3A–P compares two inventive compositions, one with polyquat 6 (2%) and SCO (4%) as opposed to one with polyquat 6 (2%) and SCO (1%).
Figure 3B:
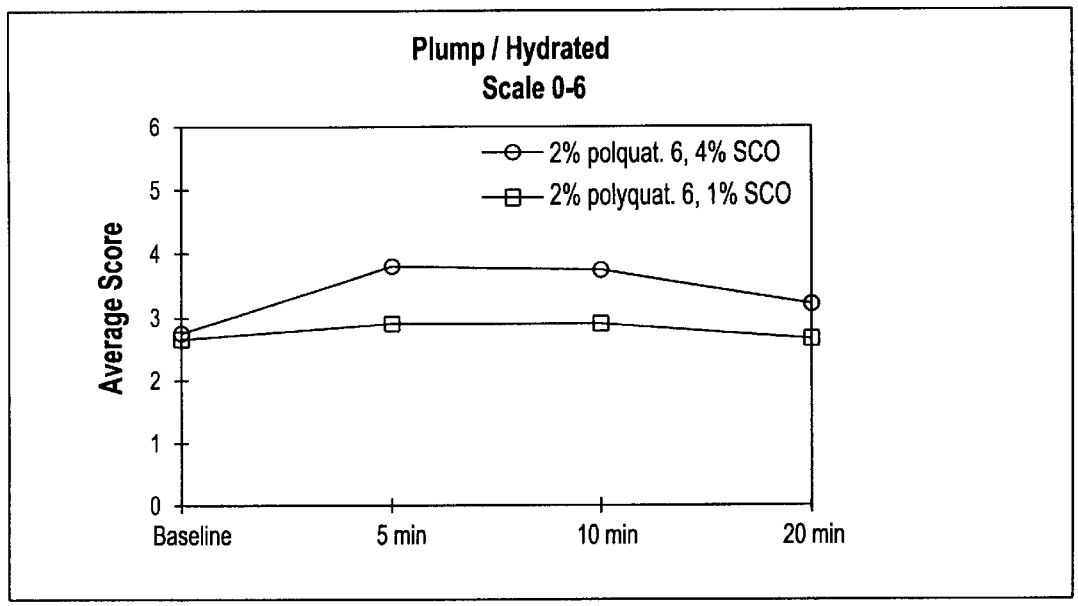
Figure 3C:
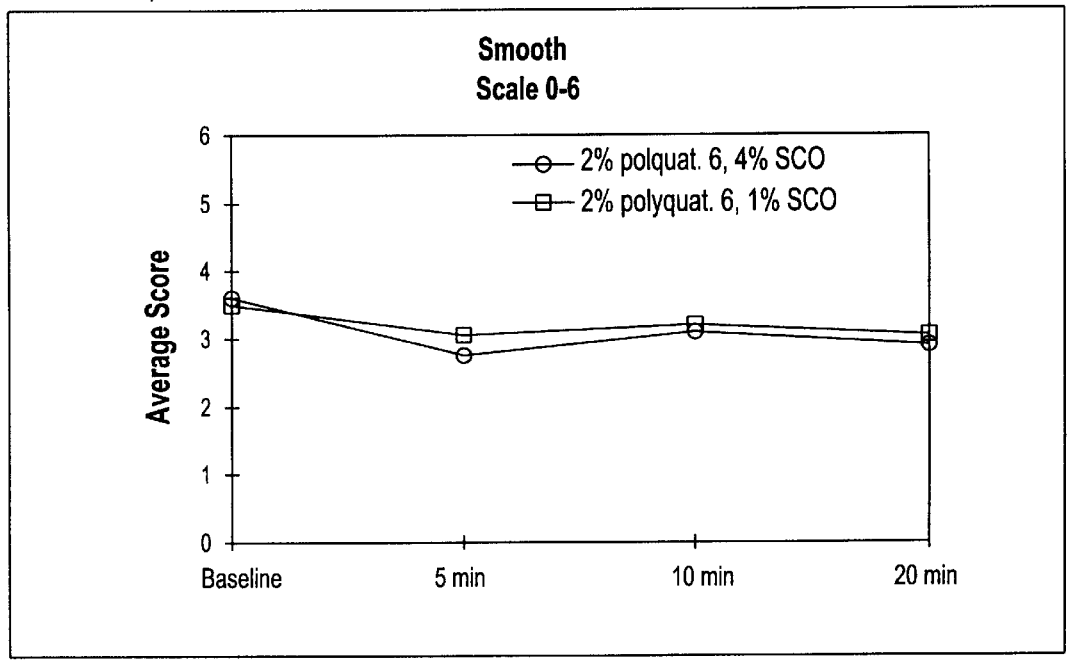
Figure 3D:
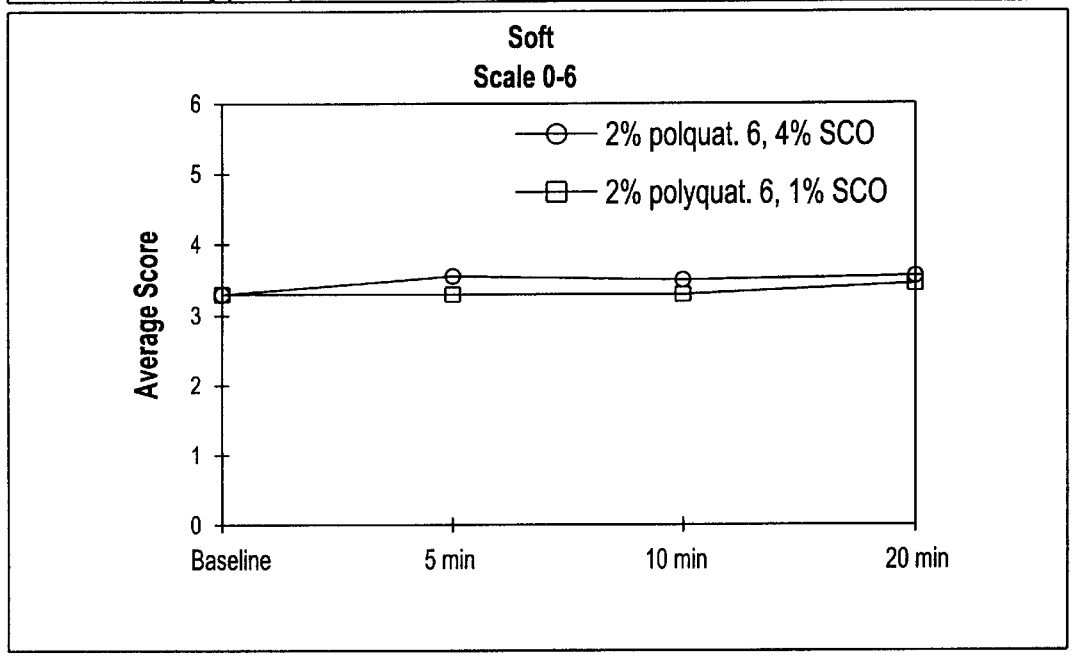
Figure 3E:
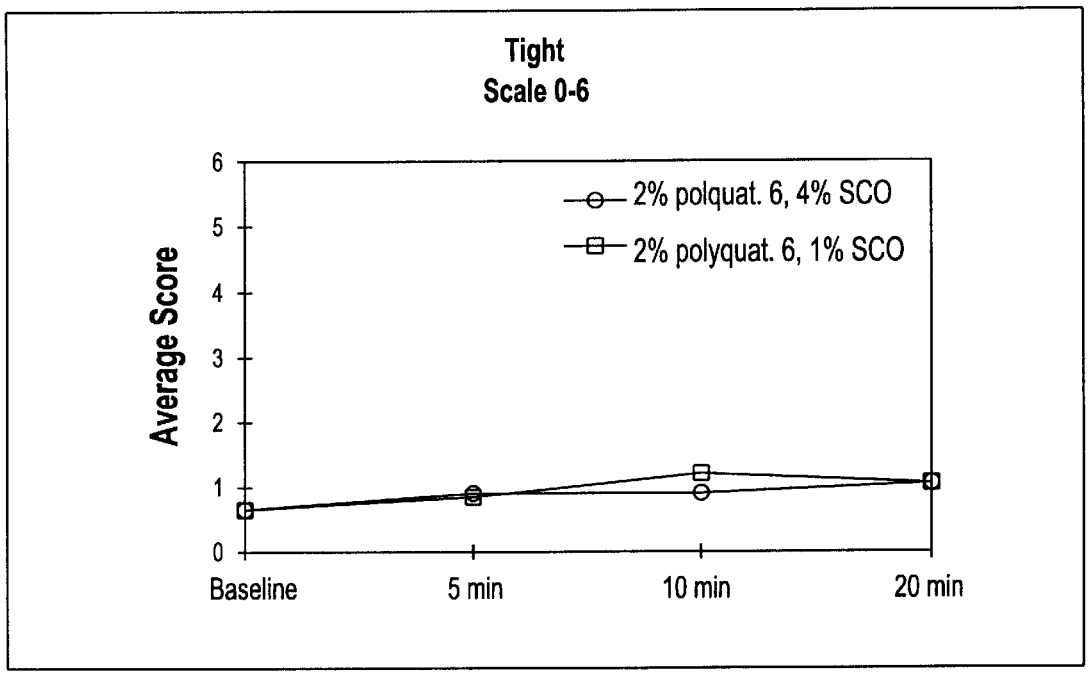
Figure 3F:
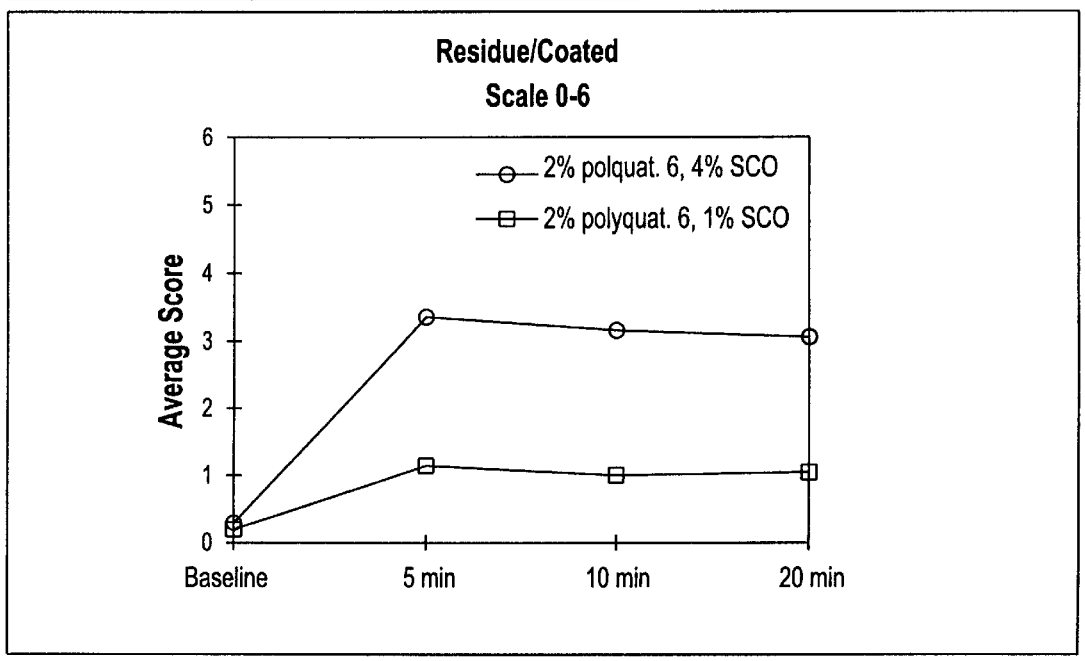
Figure 3G:
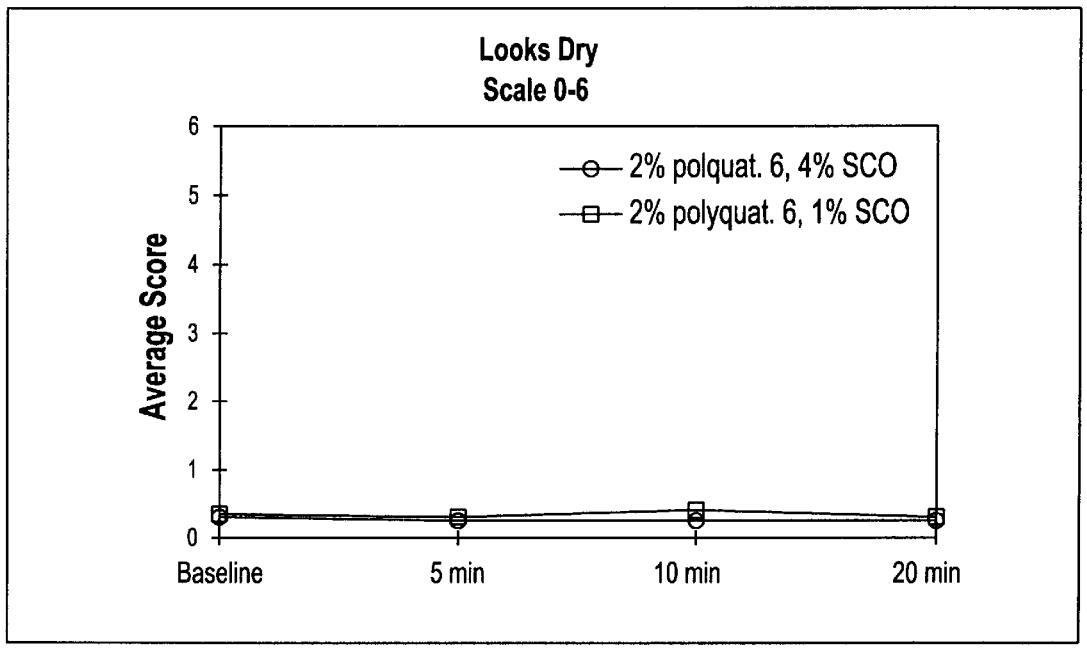
Figure 3H:
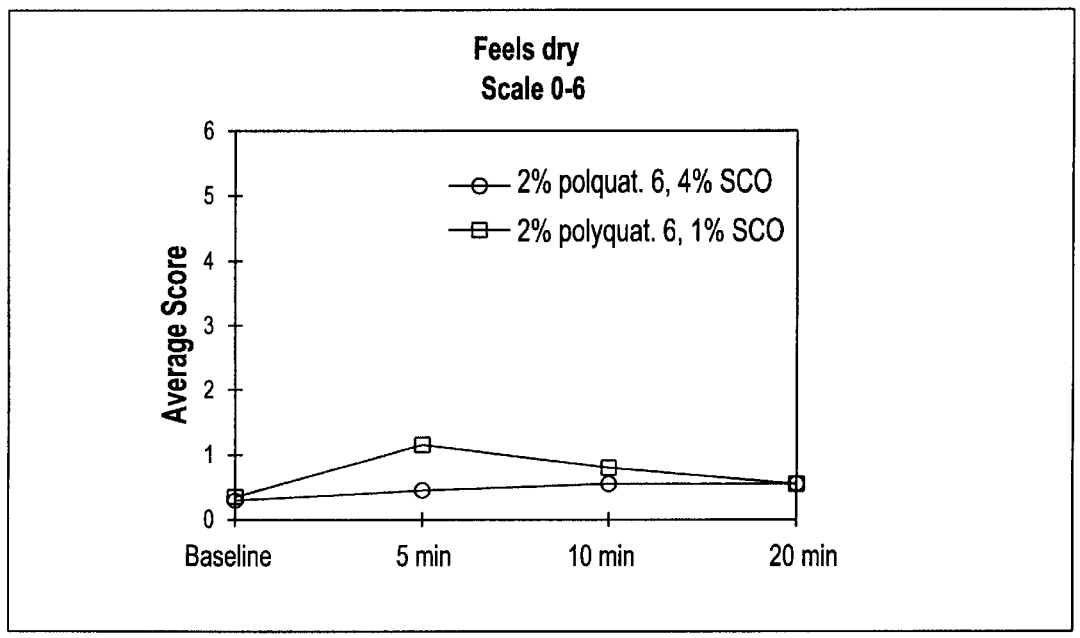
Figure 3J:
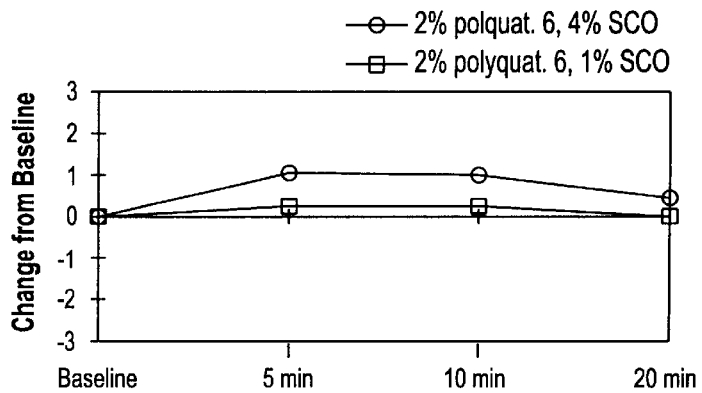
Figure 3K:
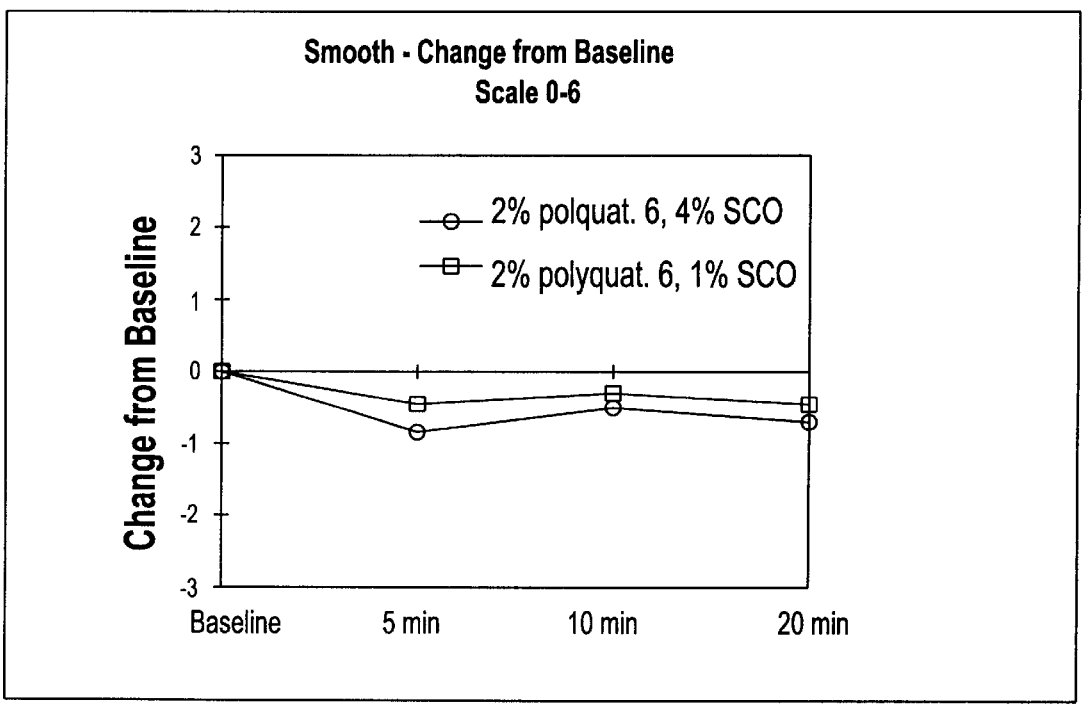
Figure 3L:
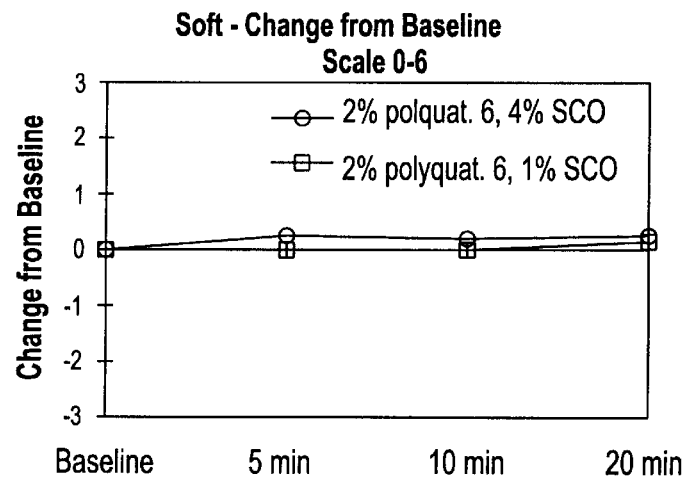
Figure 3M:
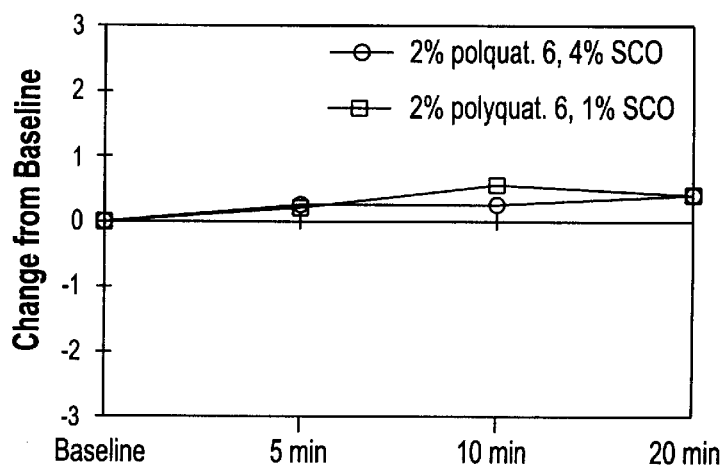
Figure 30:
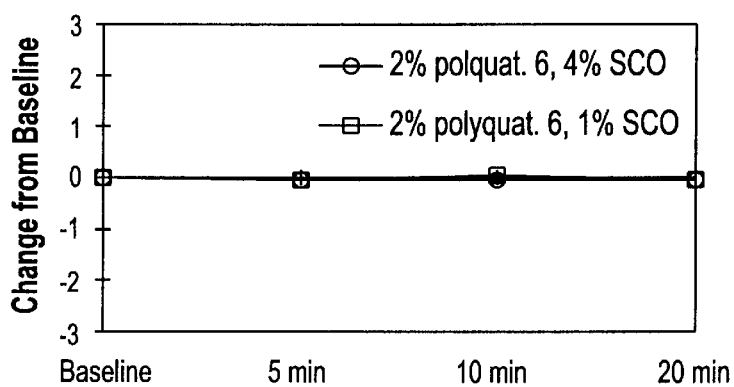
Figure 3P:
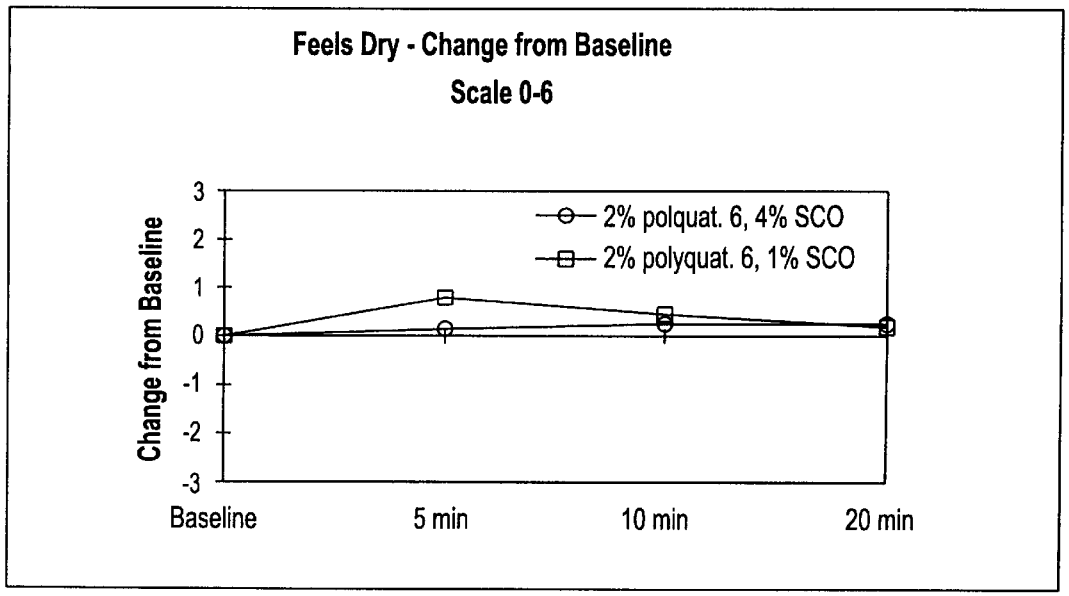
Figure 4A:
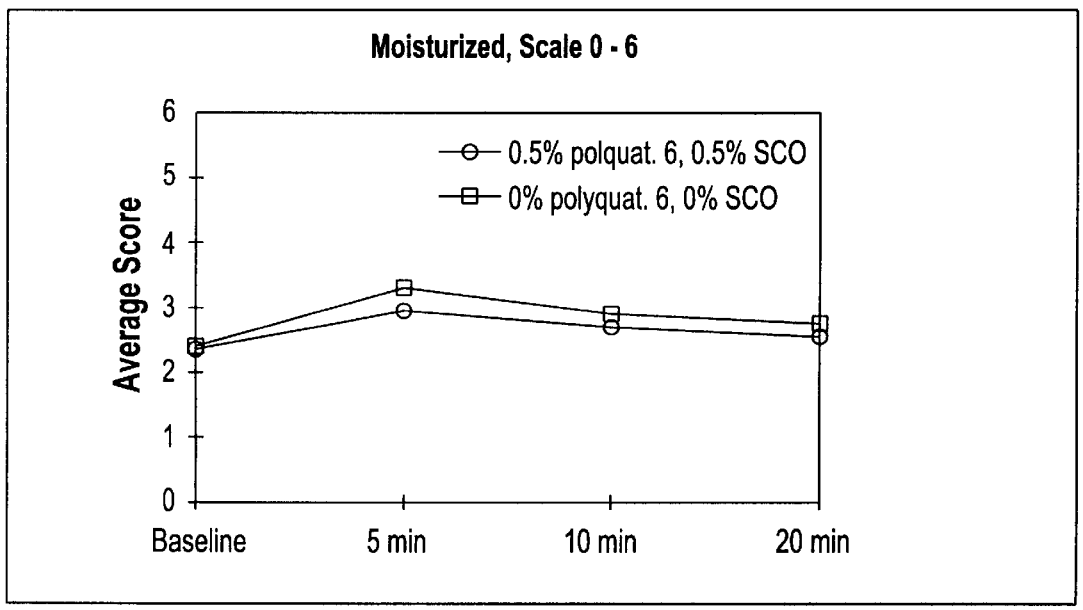
FIGS. 4A–P contrasts a composition outside the scope of the invention, with polyquat 6 and SCO each at 0.5%, as compared with a composition containing no polyquat 6 and no SCO.
Figure 4B:
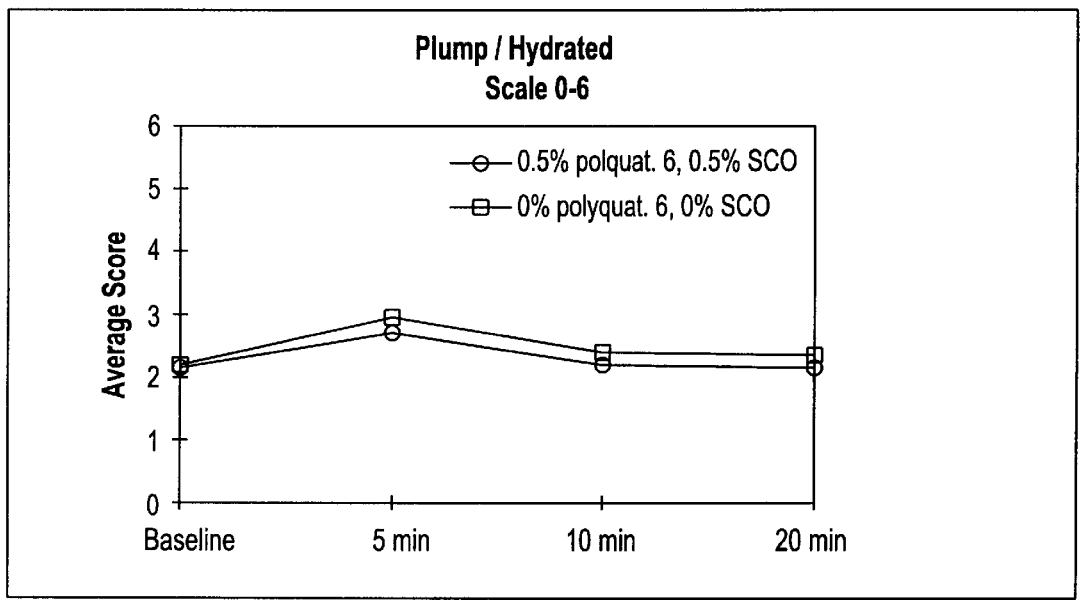
Figure 4C:
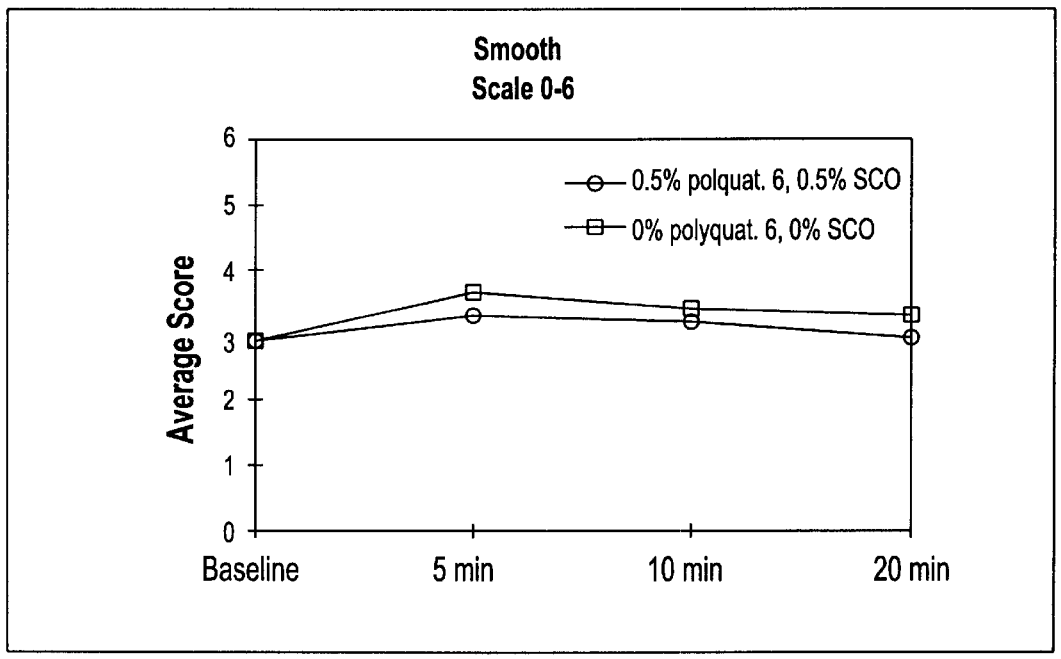
Figure 4D:
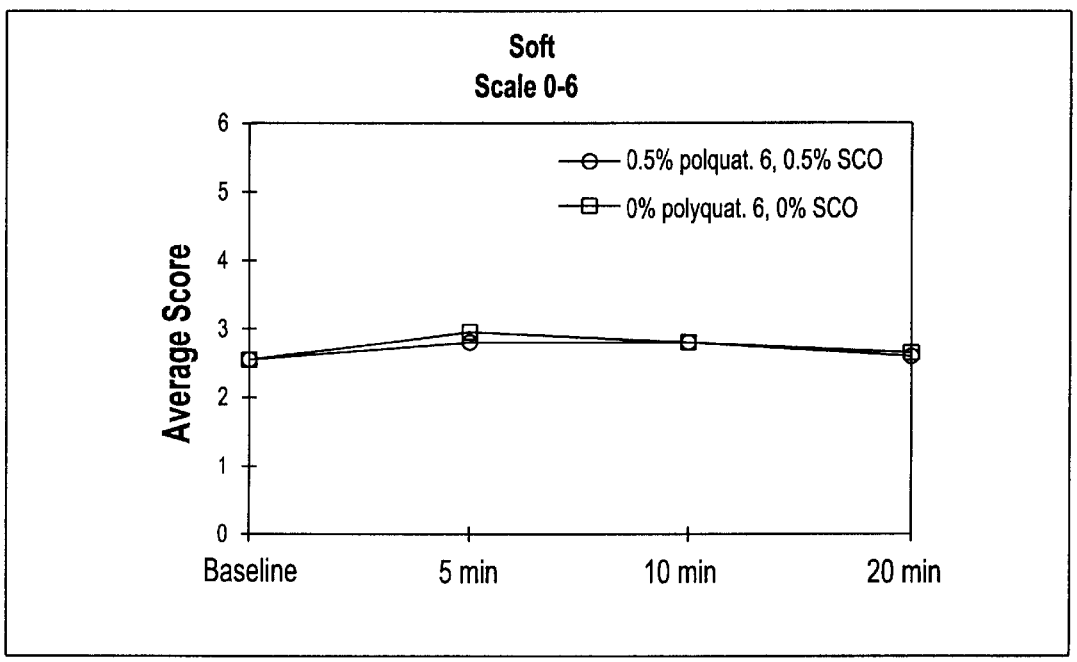
Figure 4E:
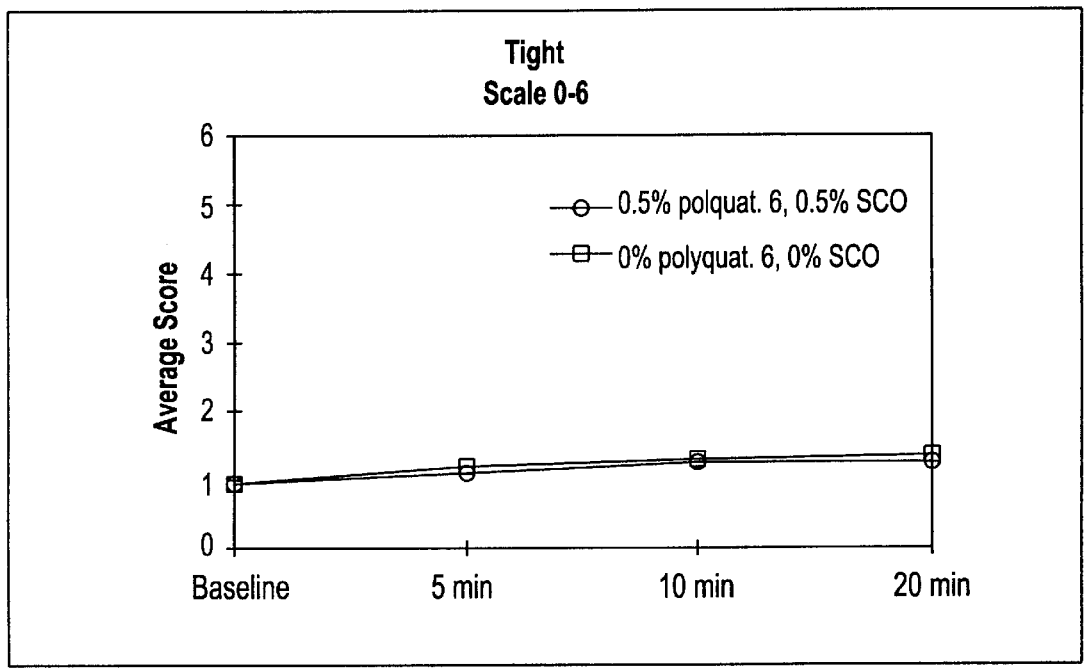
Figure 4F:
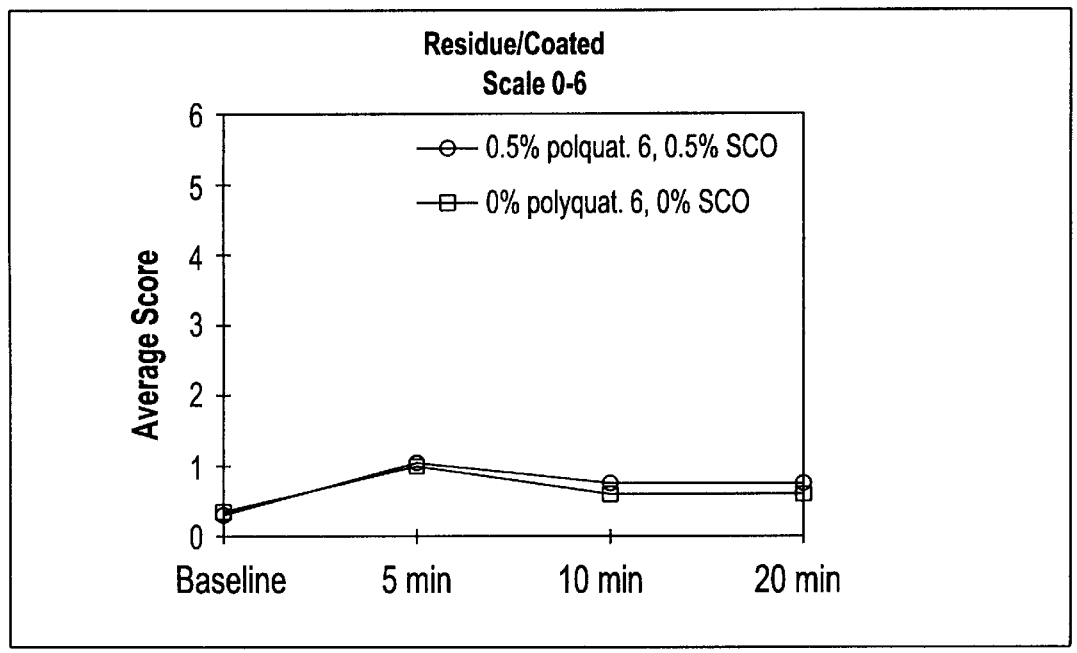
Figure 4G:
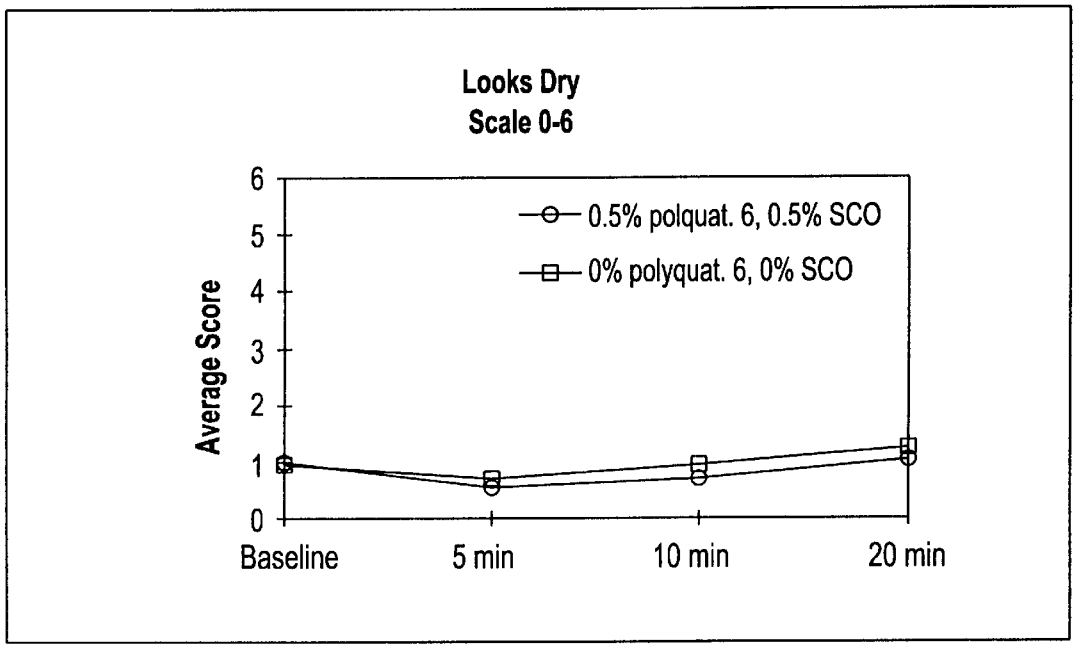
Figure 4H:
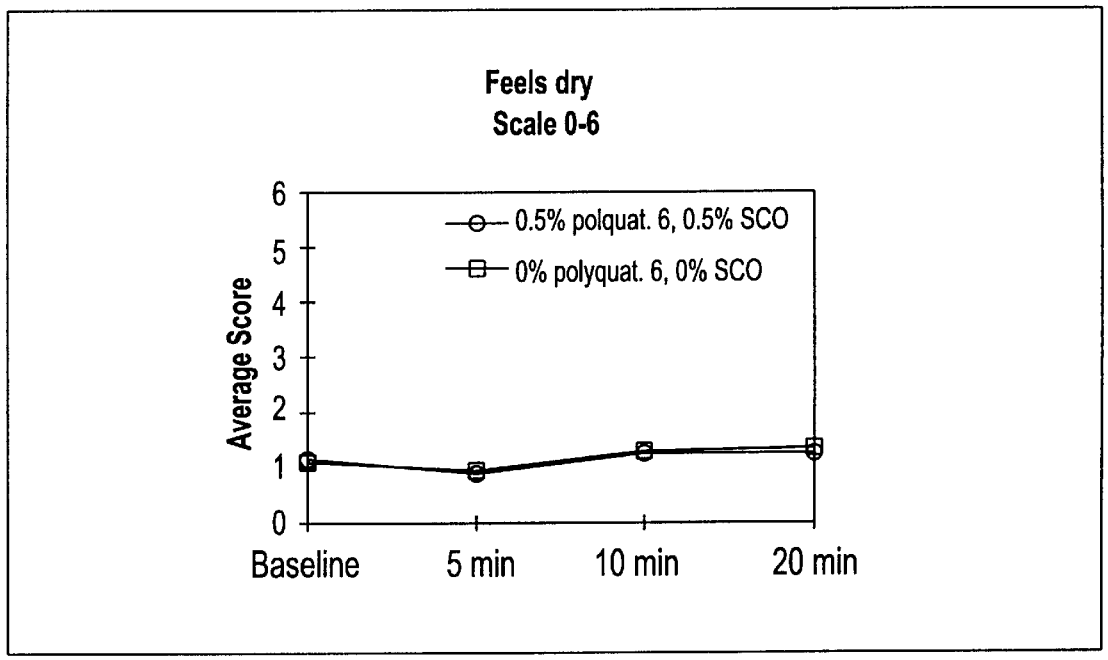
Figure 4J:
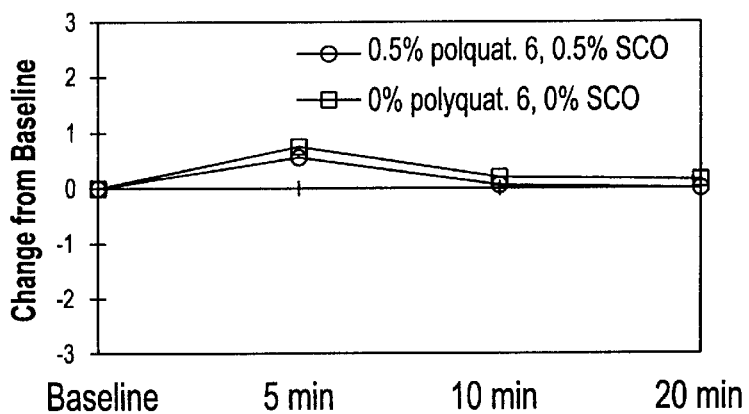
Figure 4K:
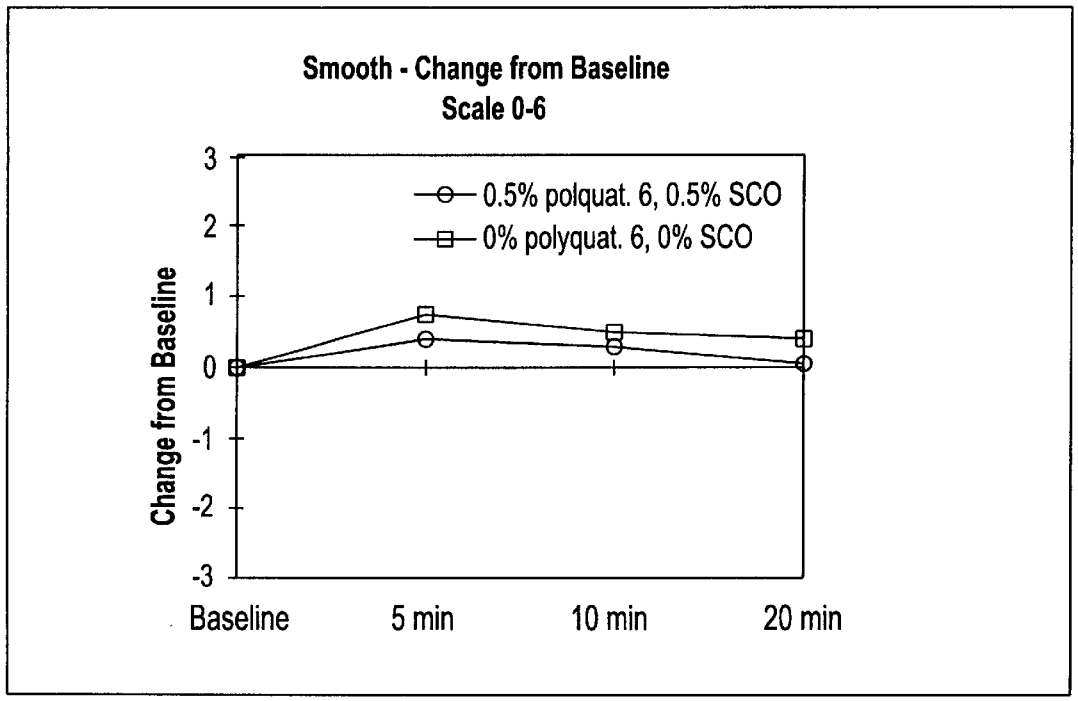
Figure 4L:
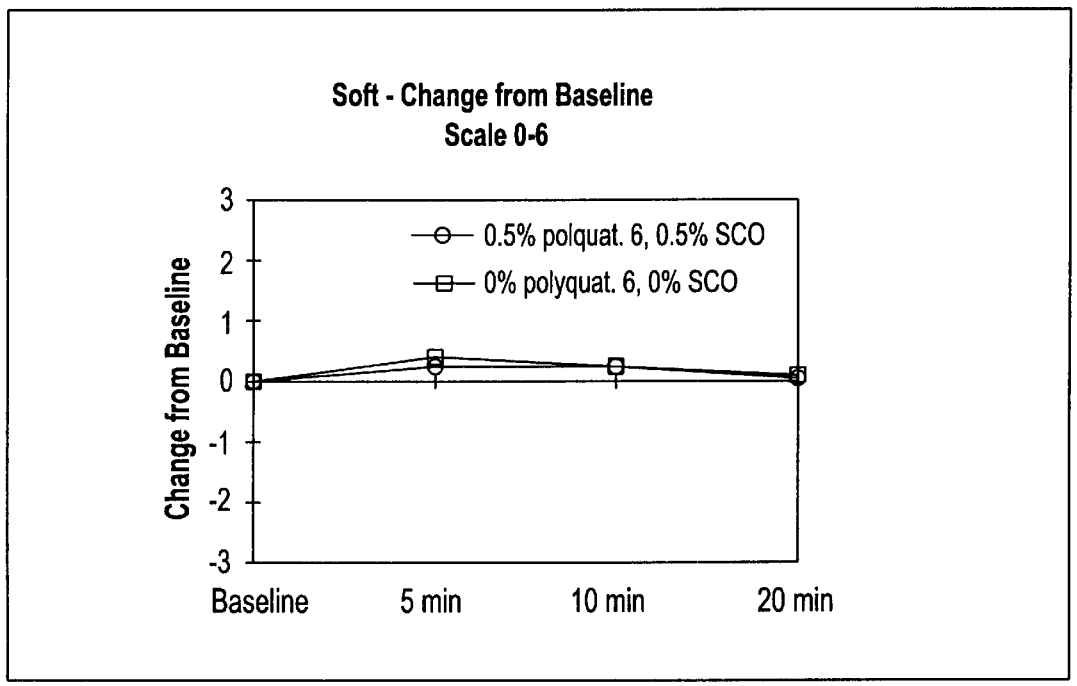
Figure 4M:
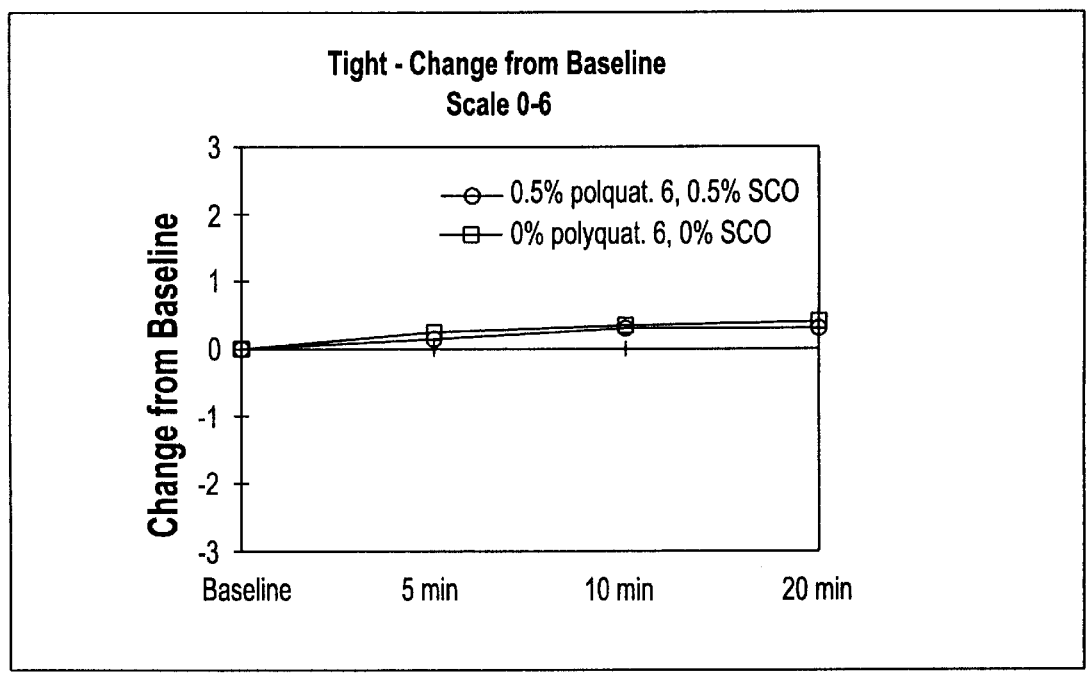
Figure 4N:
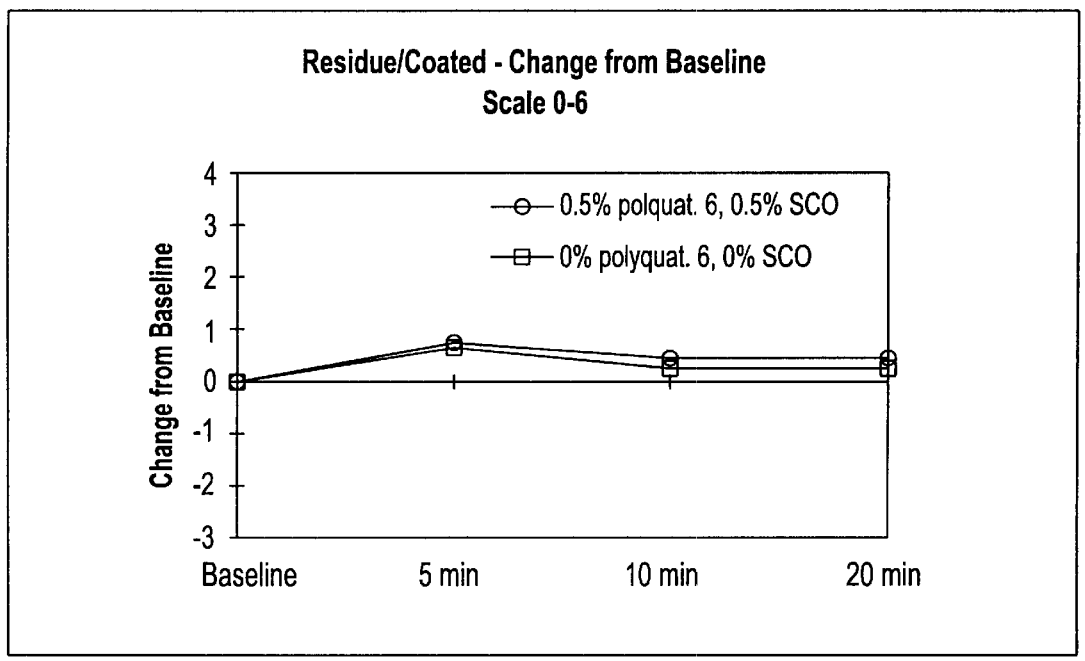
Figure 40:
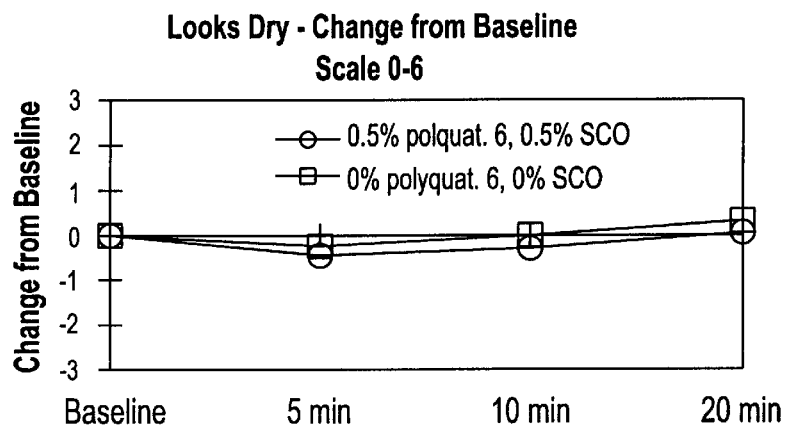
Figure 4P:
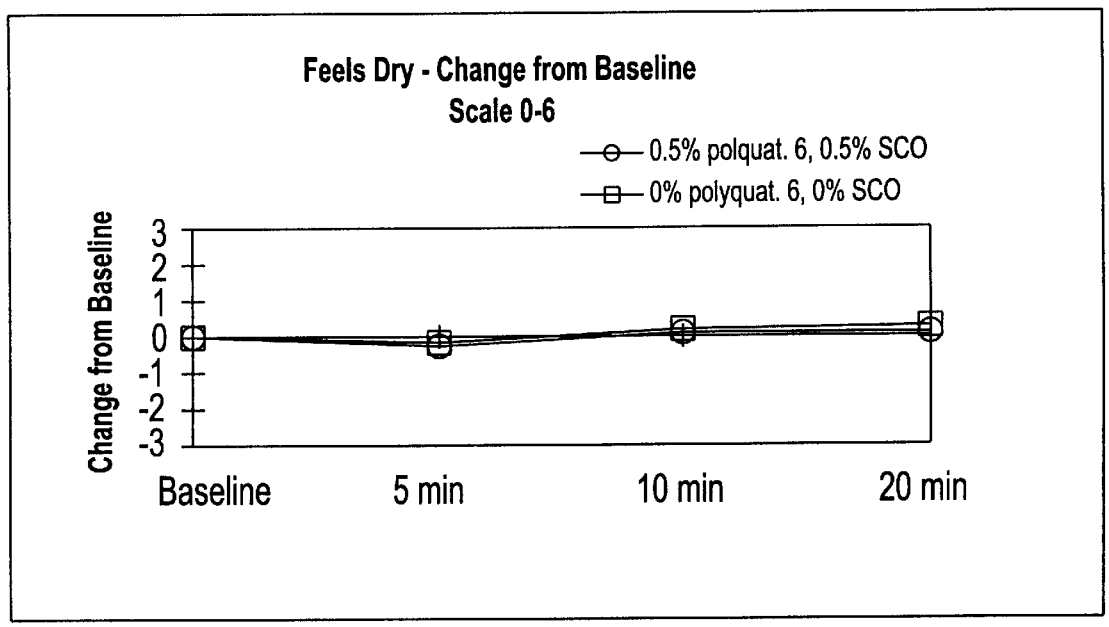
Figure 7A:
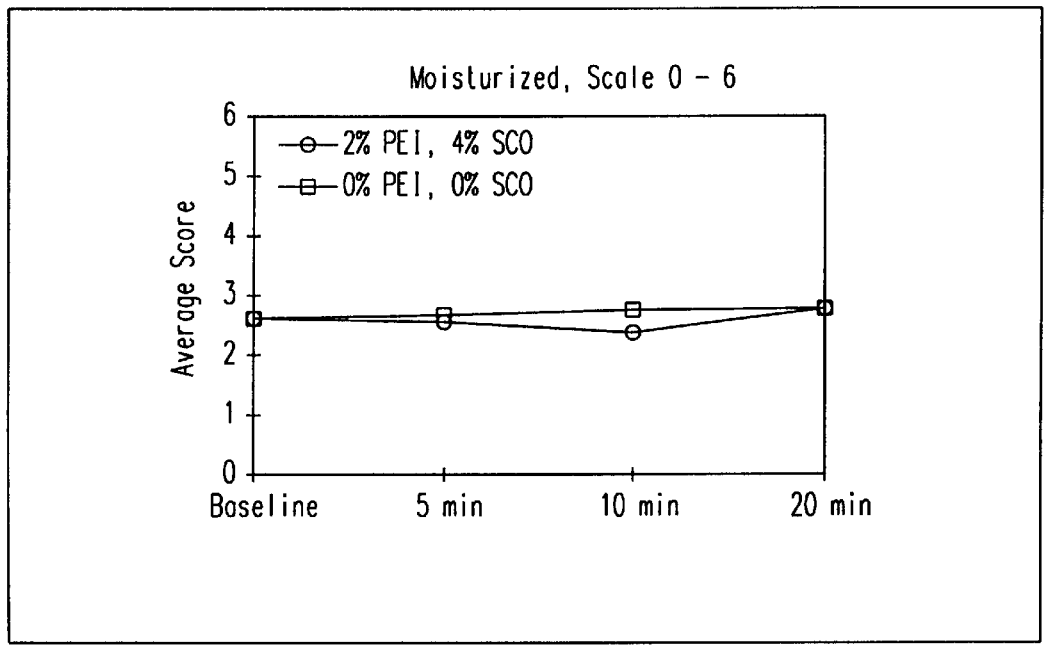
FIGS. 7A–P compare an inventive composition comprising polyethylenimine (2%) and SCO (4%) contrasted with the control lacking both the cationic polymer and anionic emollient.
Figure 7B:
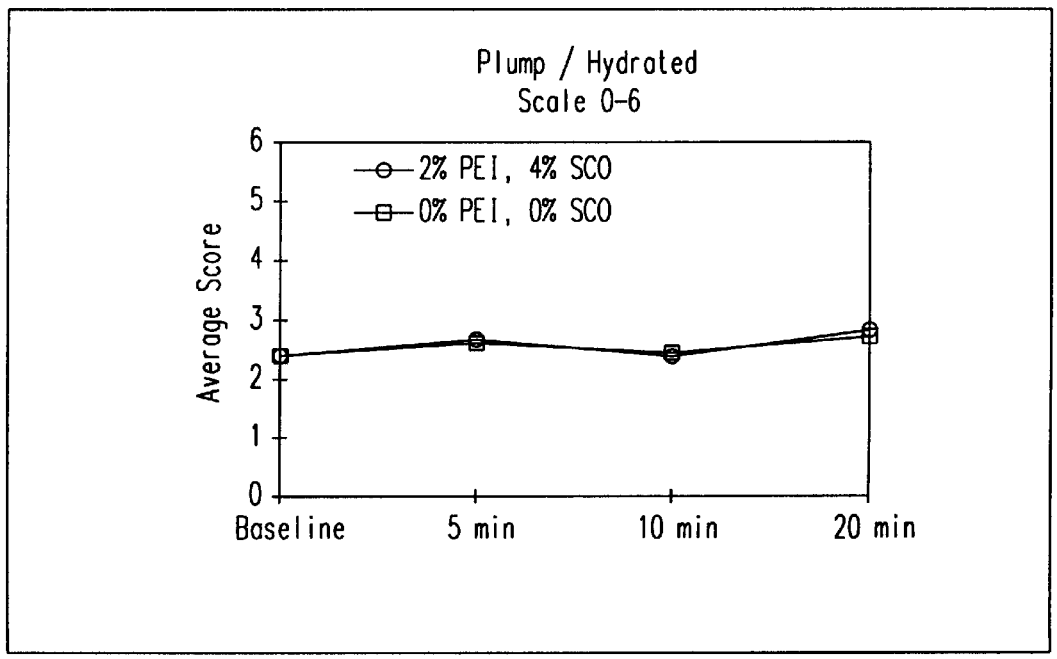
Figure 7C:
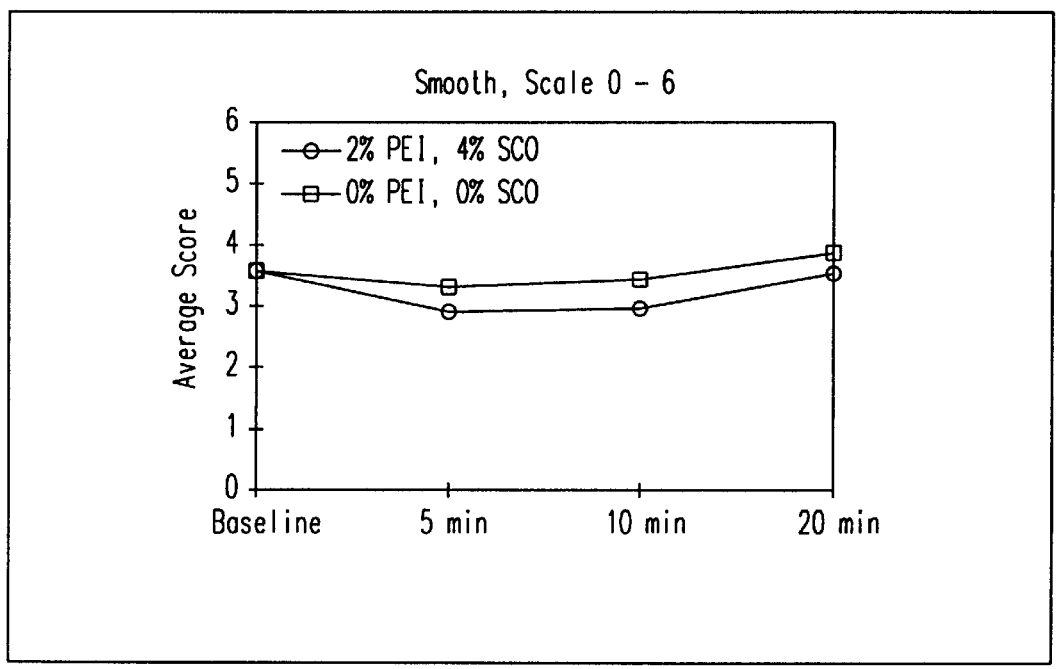
Figure 7D:
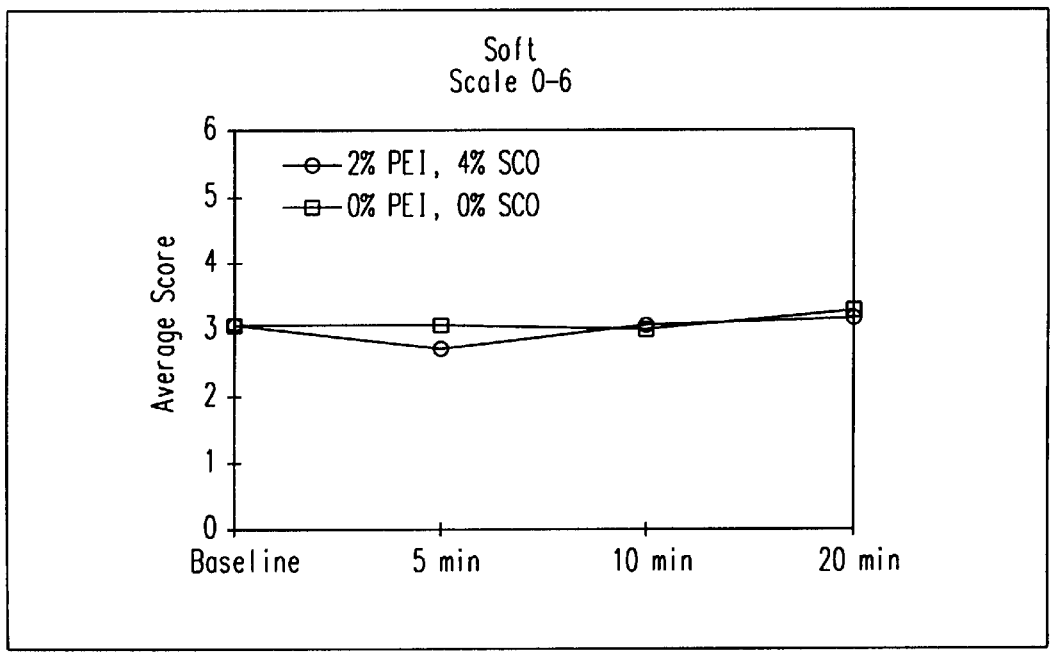
Figure 7E:
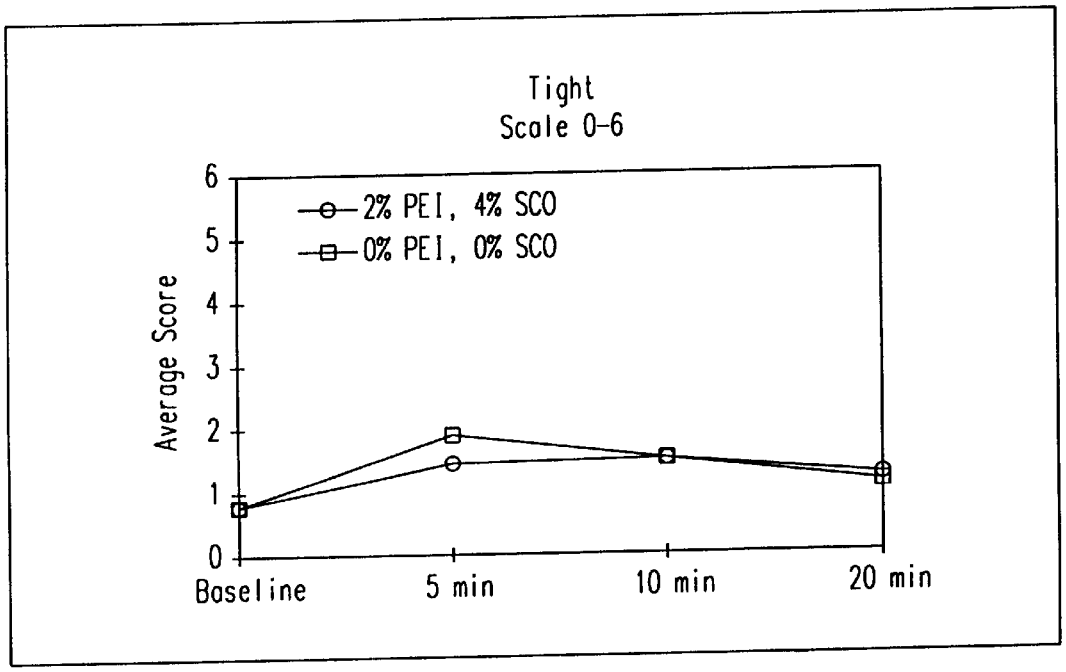
Figure 7F:
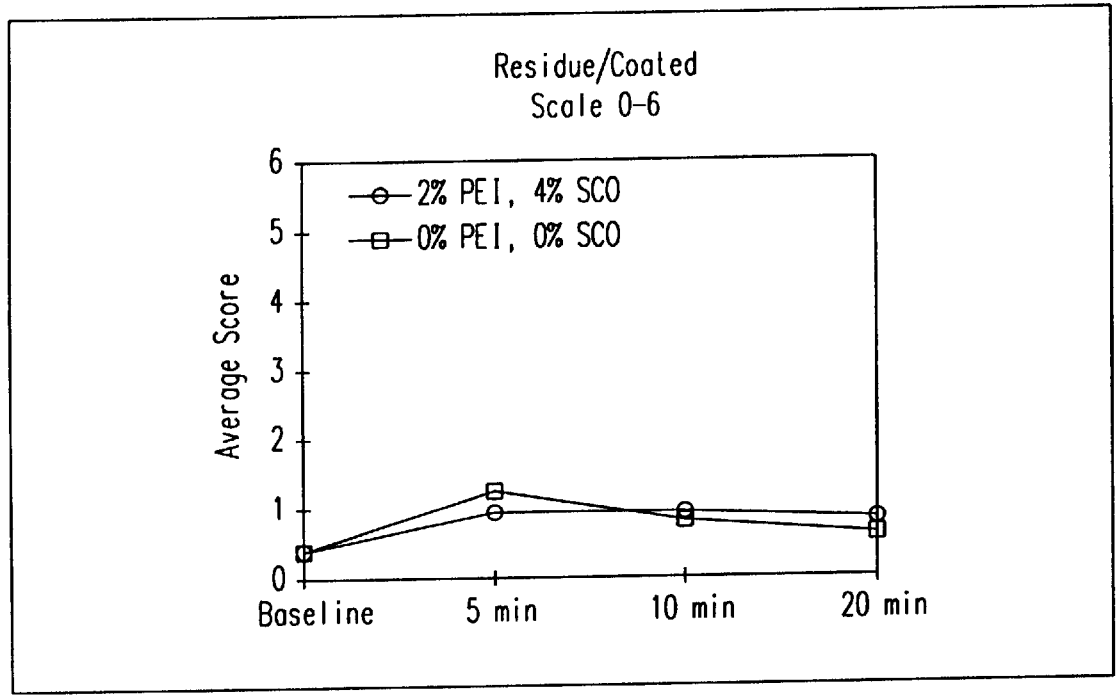
Figure 7G:
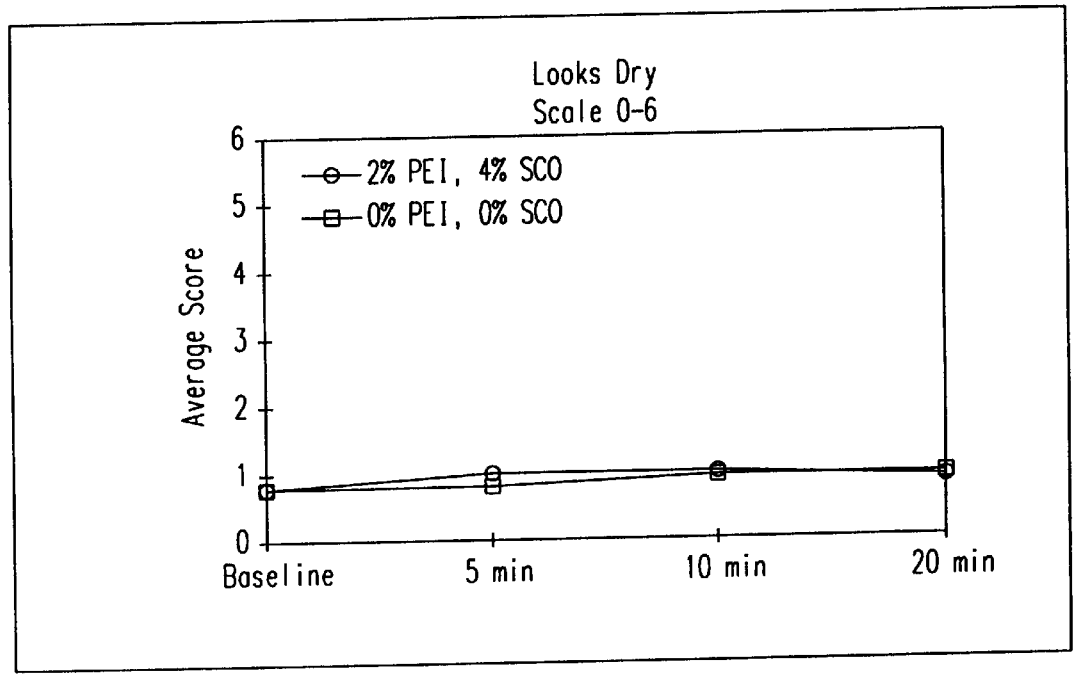
Figure 7H:
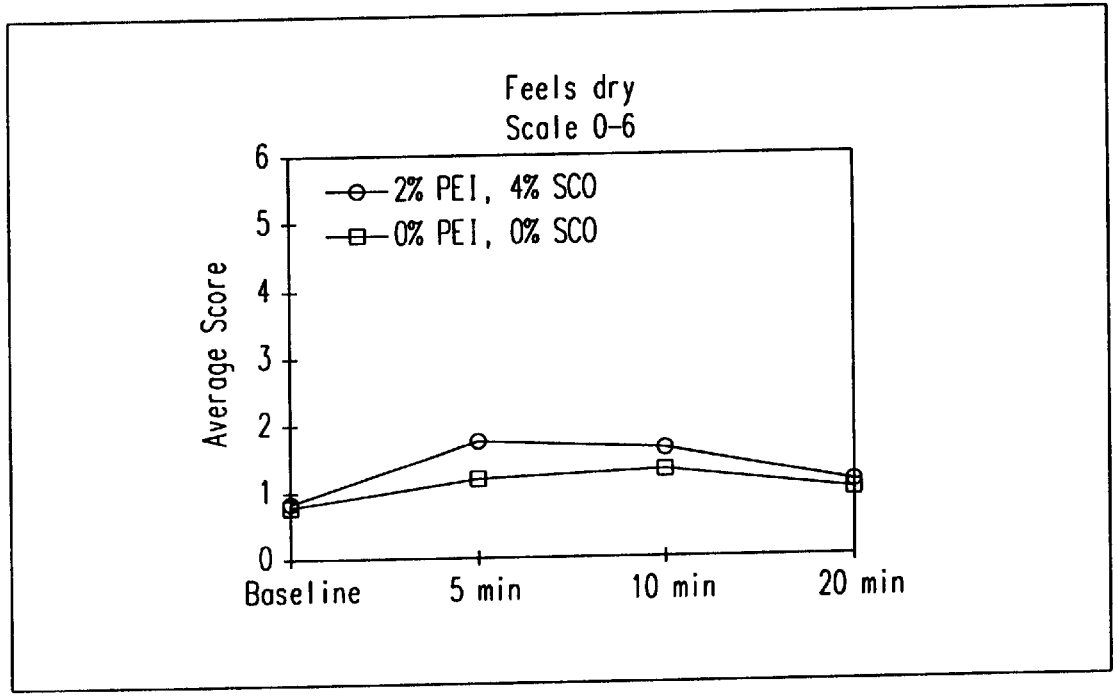
Figure 71:
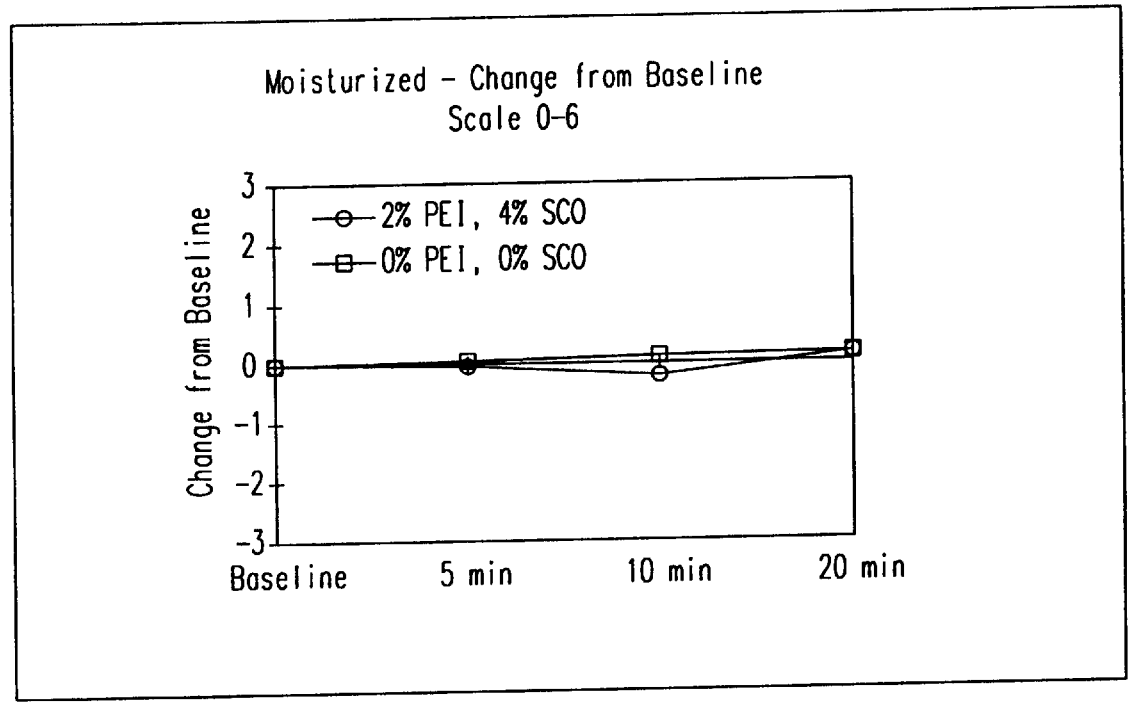
Figure 7J:
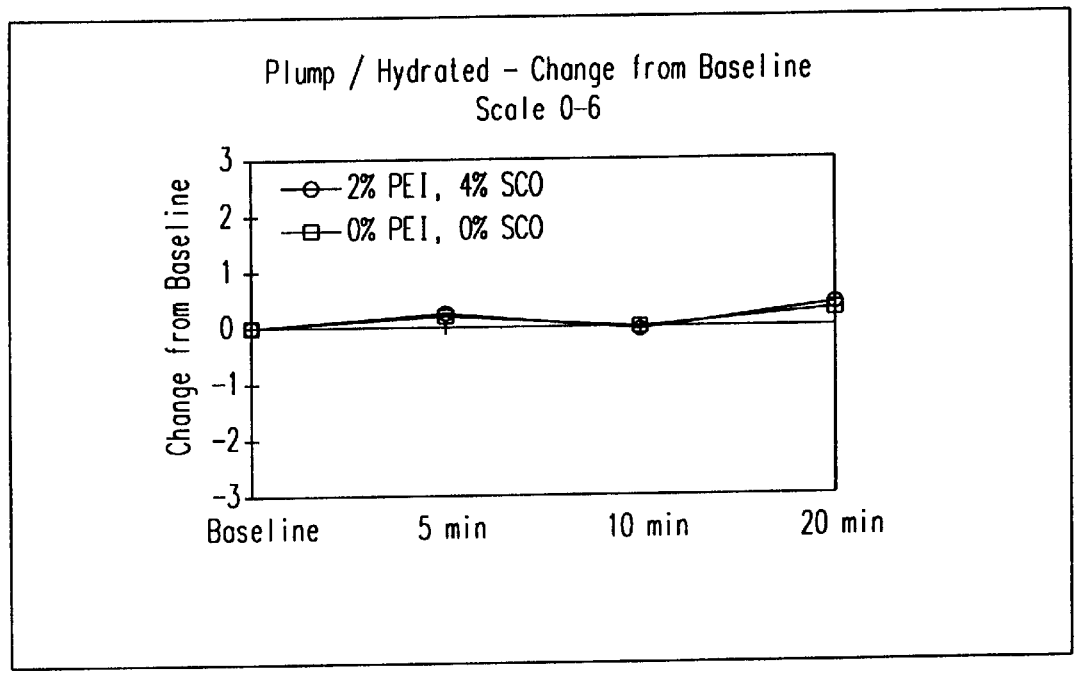
Figure 7K:
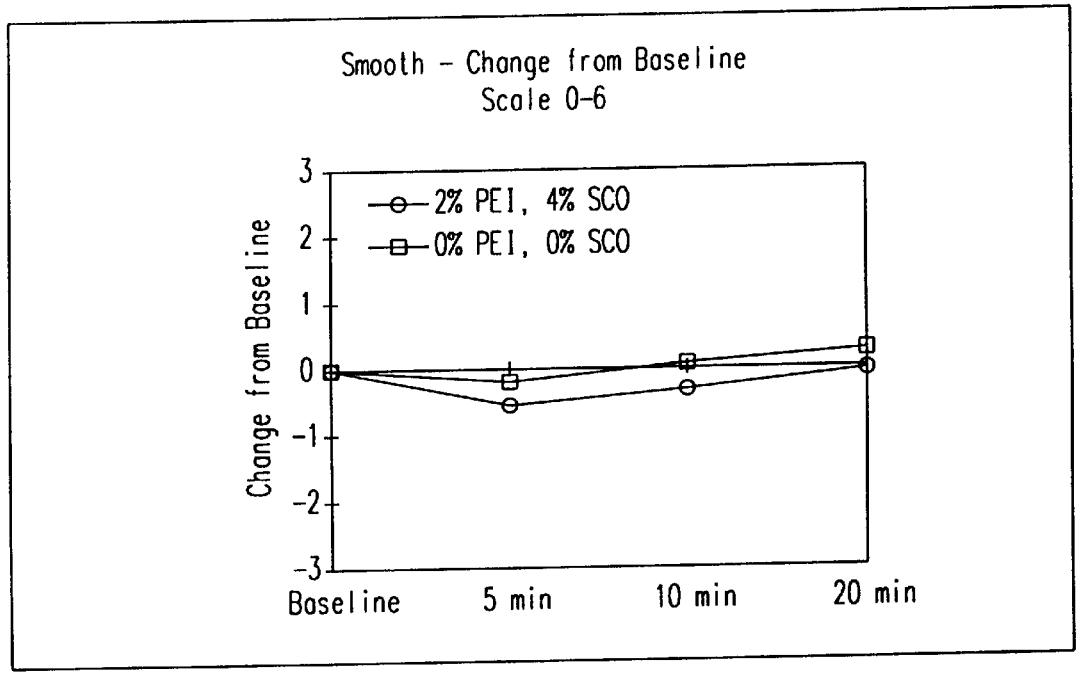
Figure 7L:
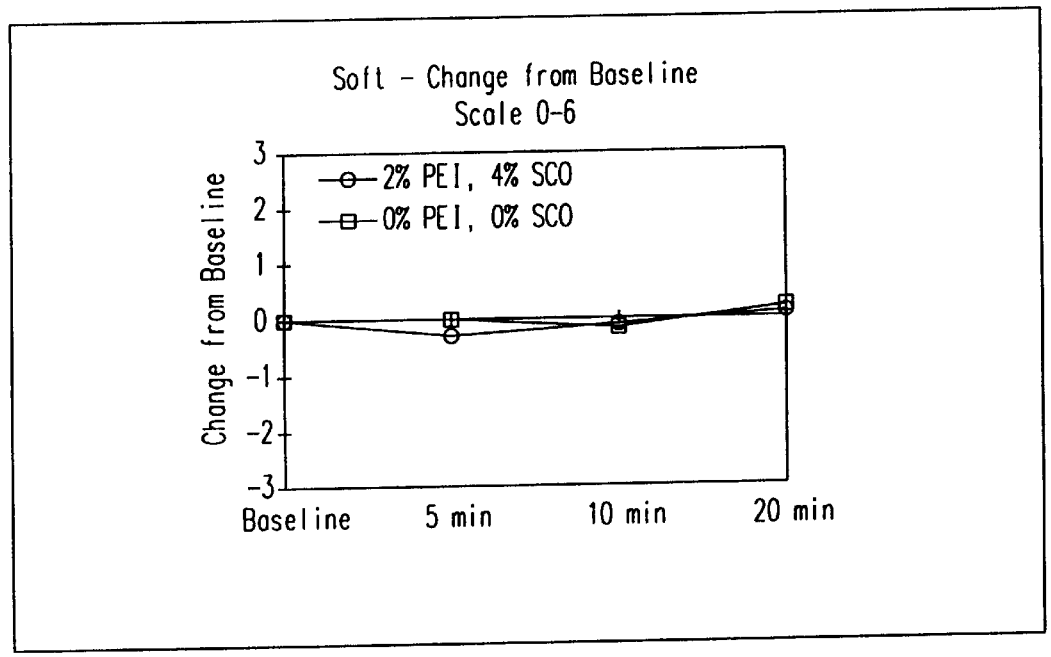
Figure 7M:
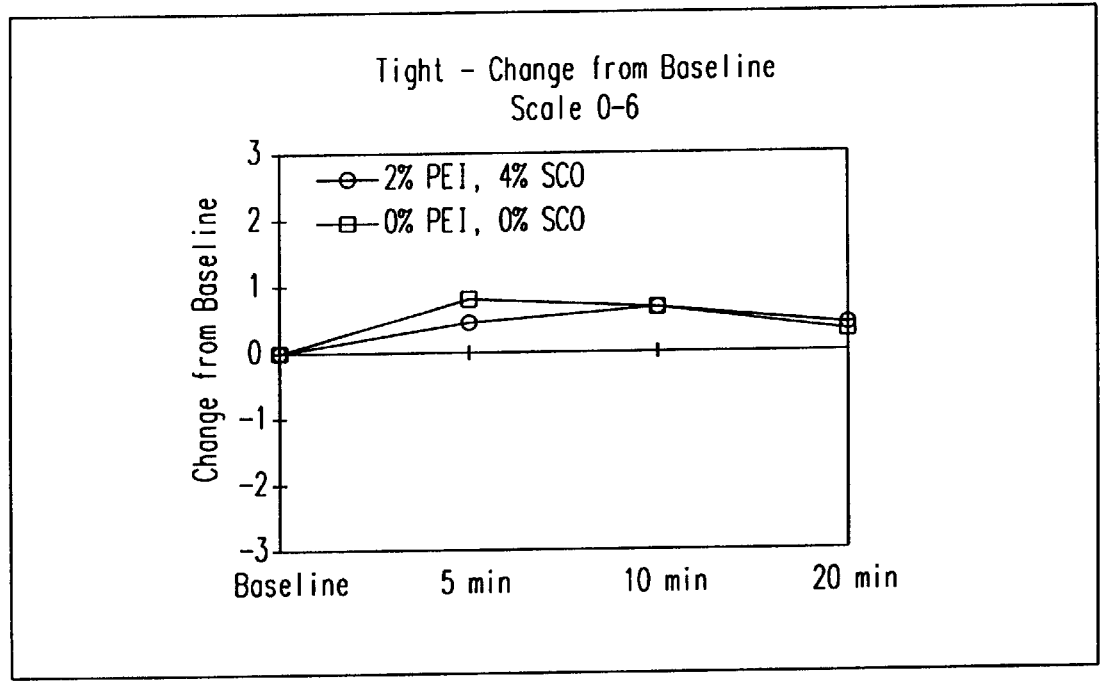
Figure 7N:
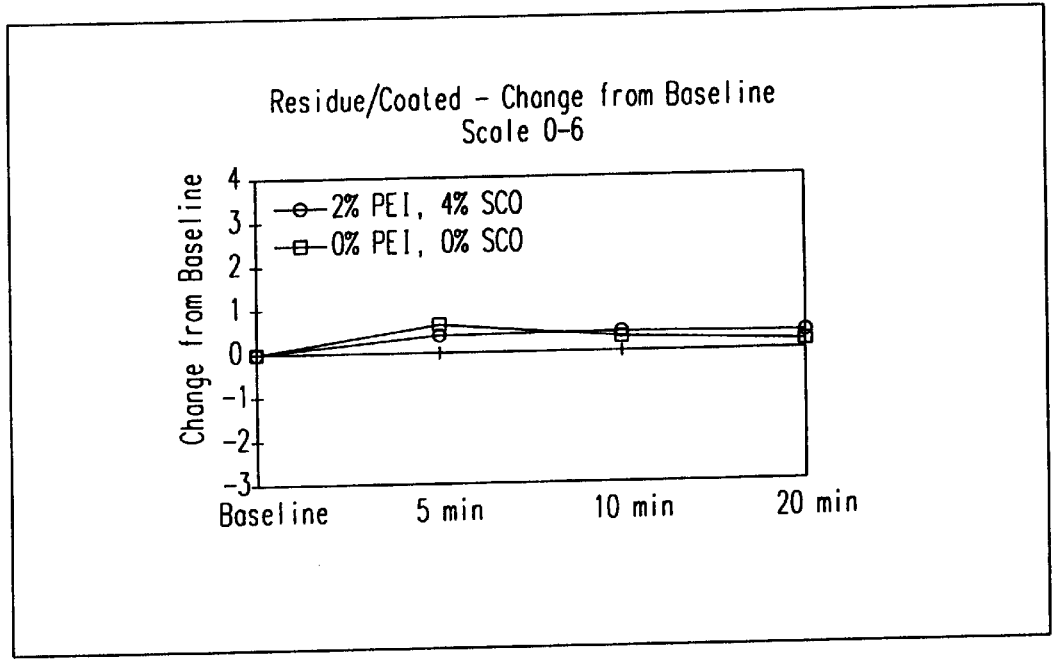
Figure 70:
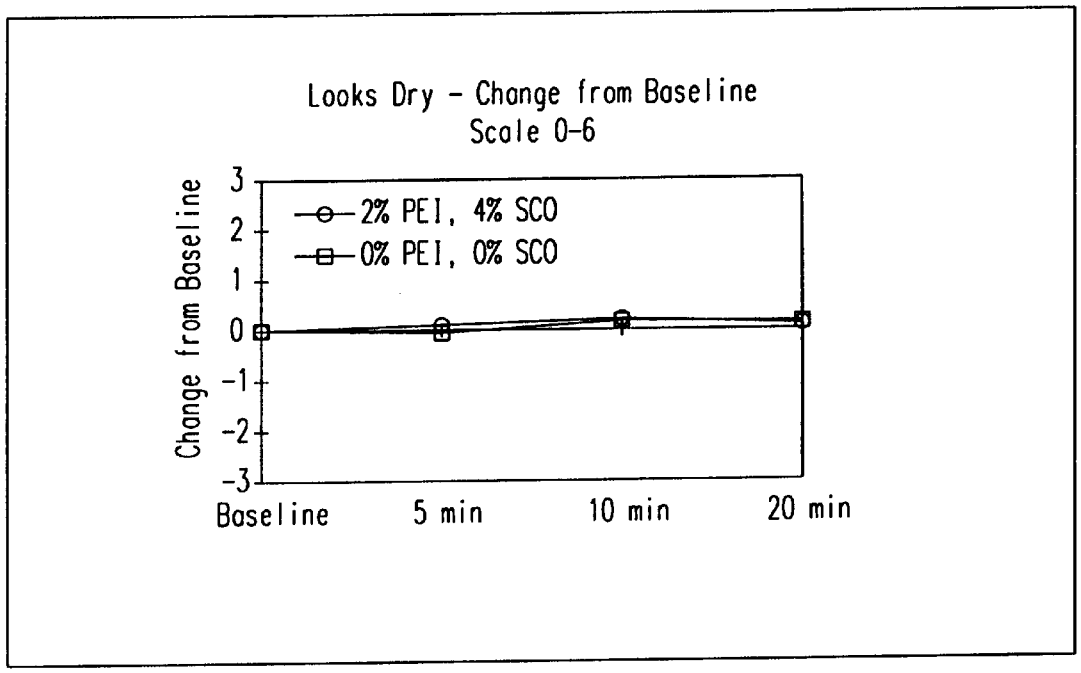
Figure 7P:
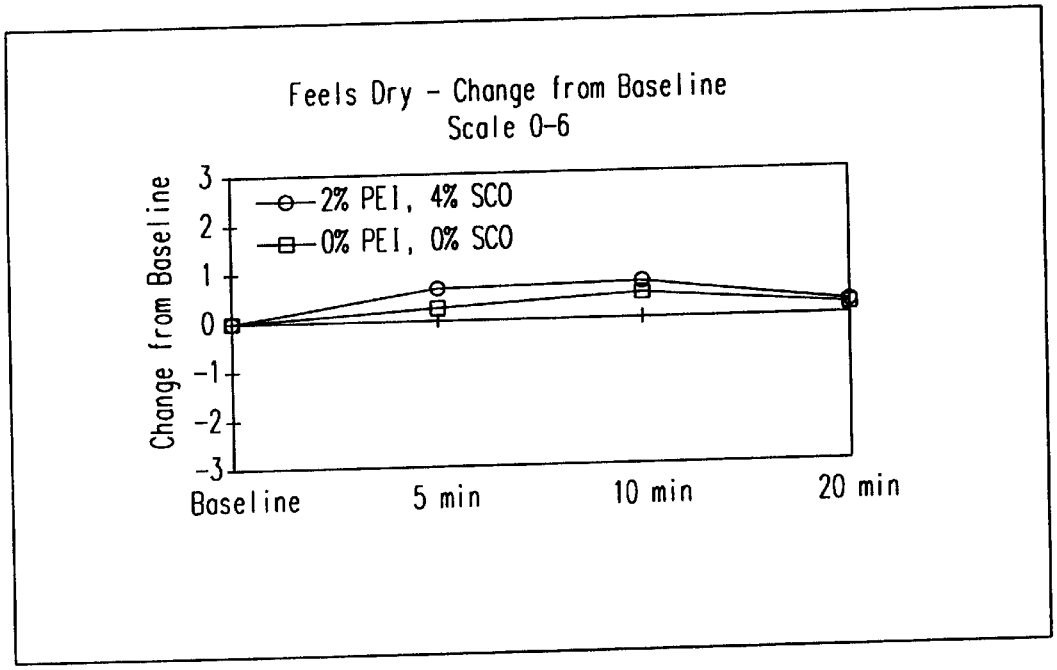
Figure 8A:
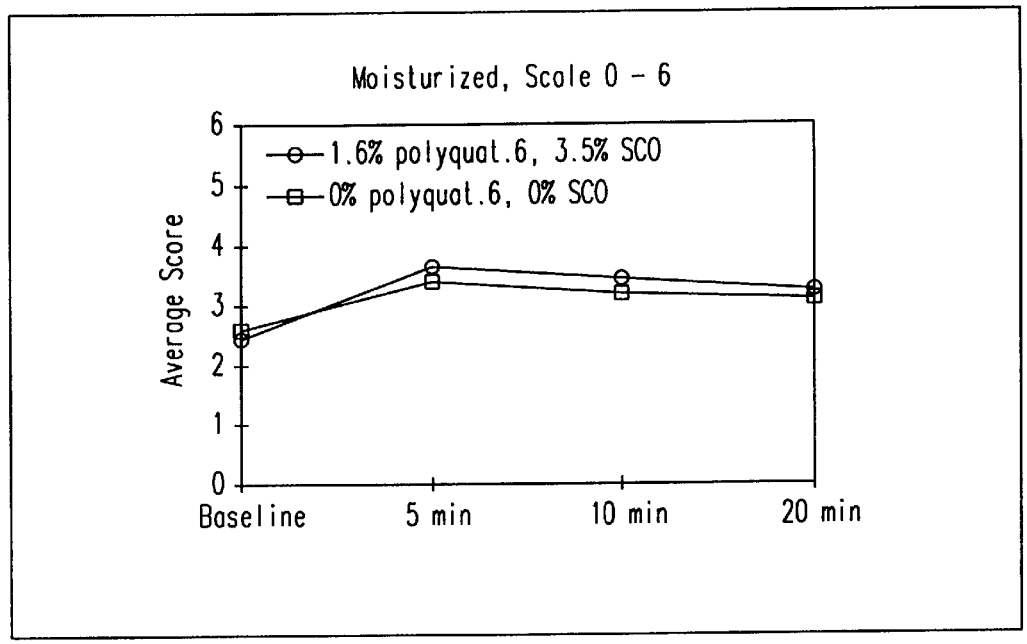
FIGS. 8A–P contrast a bath formula comprising polyquat 6 (1.6%) and SCO (3.5%) with a bath formula lacking both polyquat 6 and SCO.
Figure 8B:
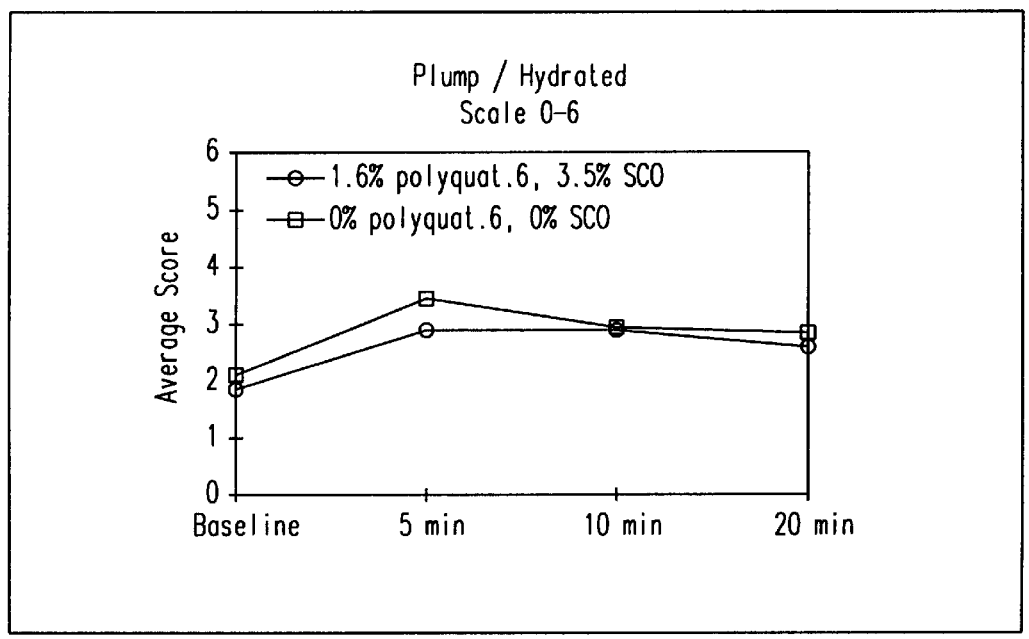
Figure 8C:
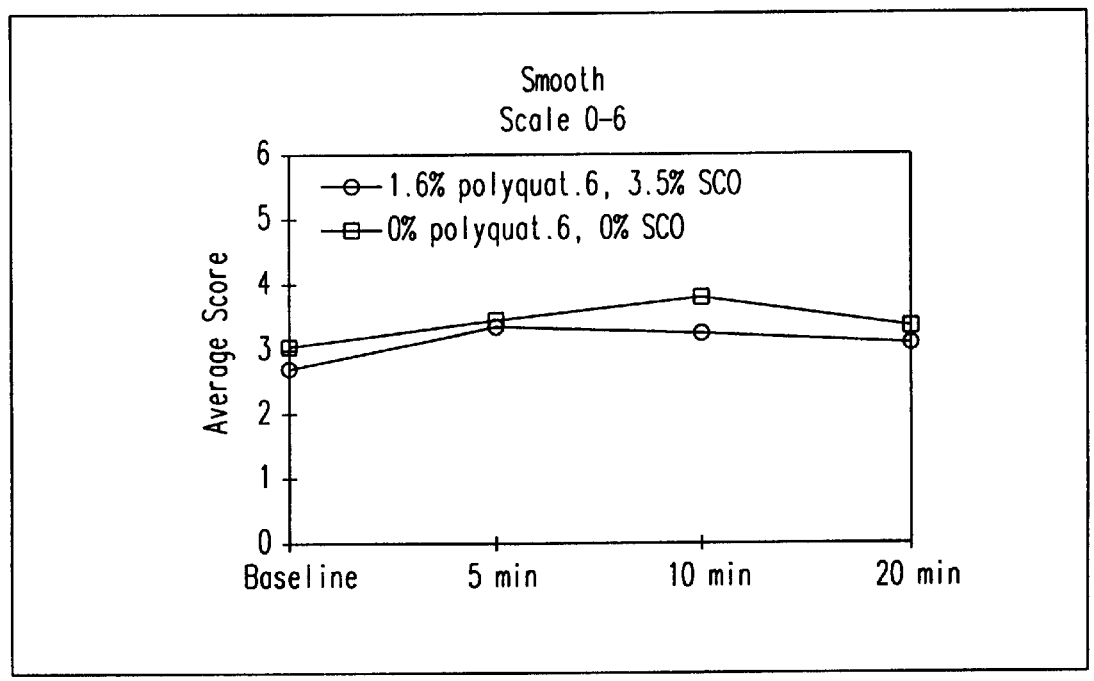
Figure 8D:
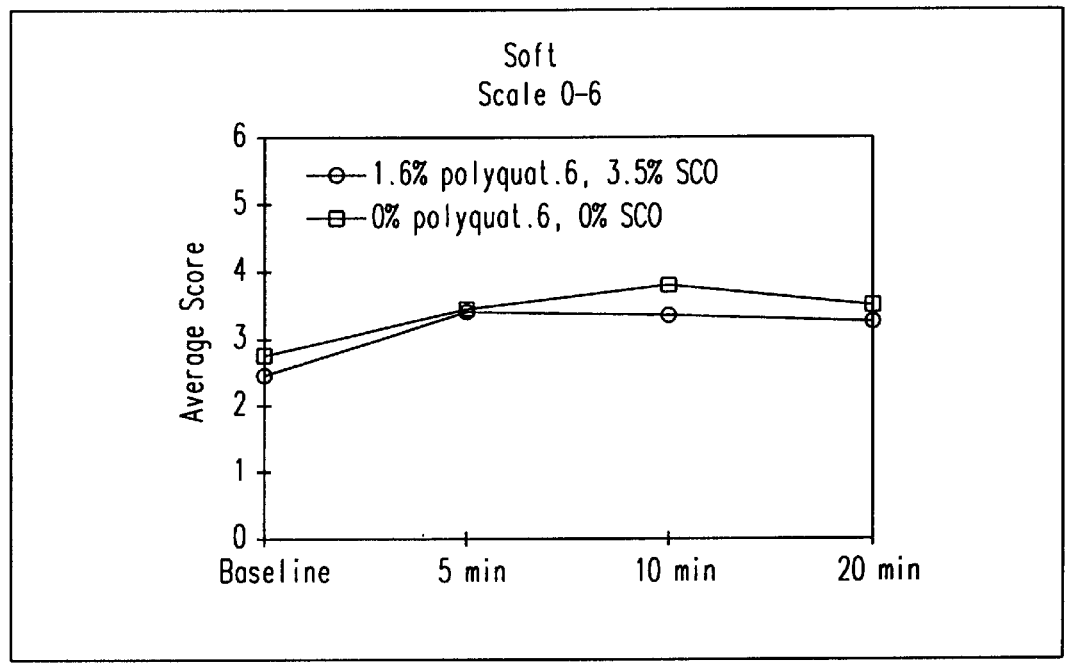
Figure 8E:
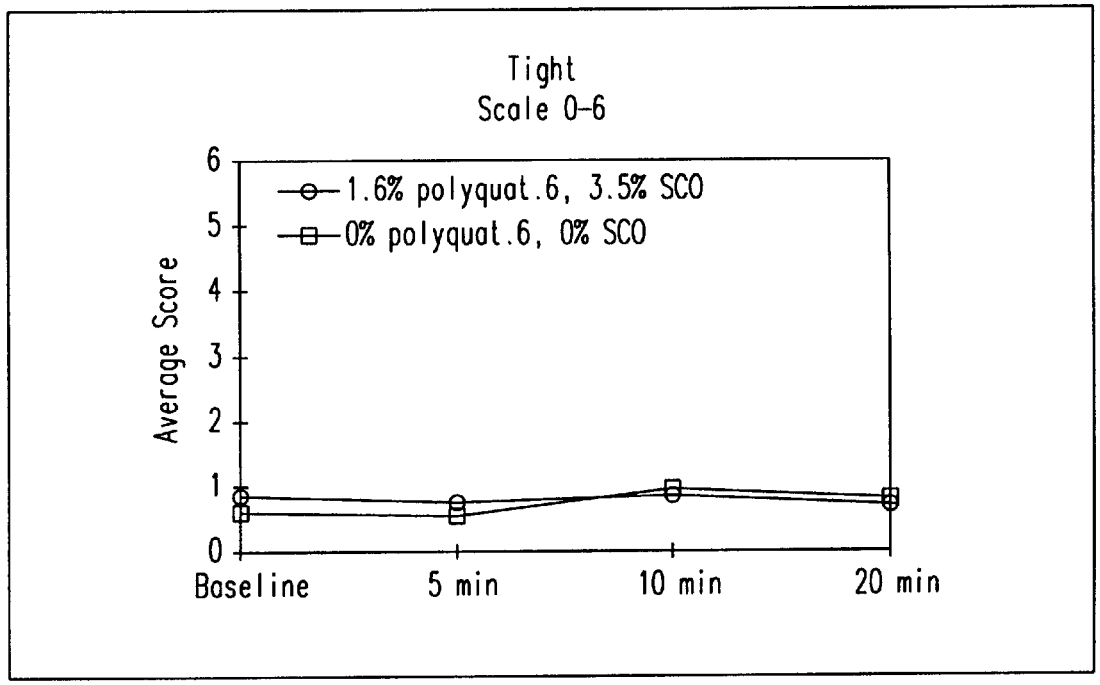
Figure 8F:
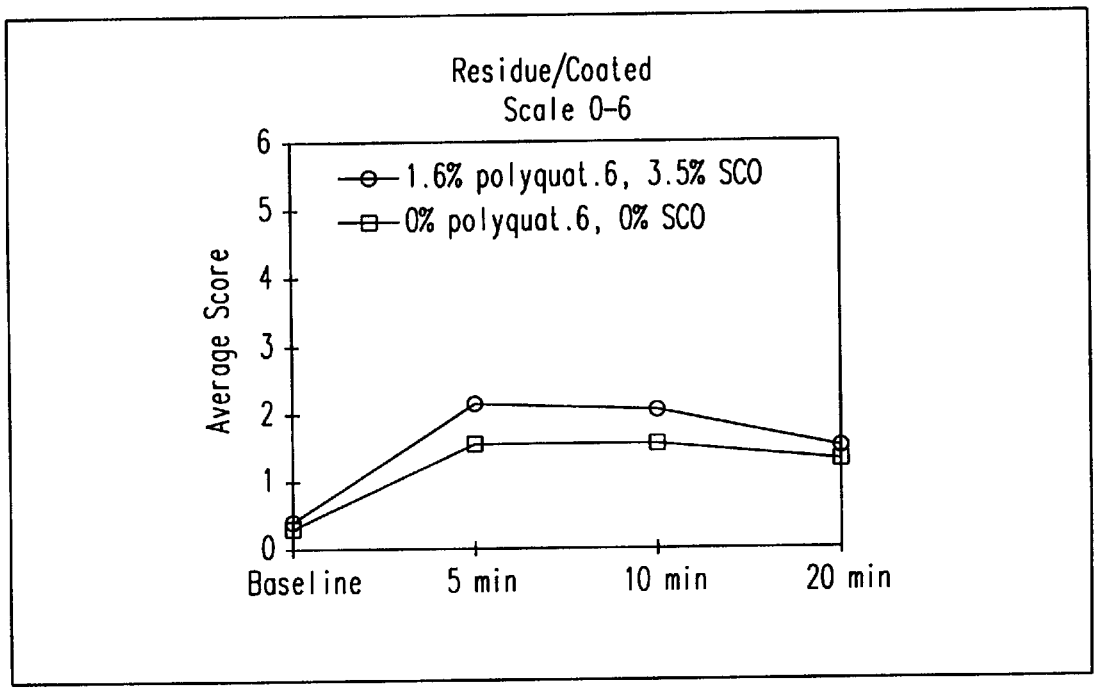
Figure 8G:
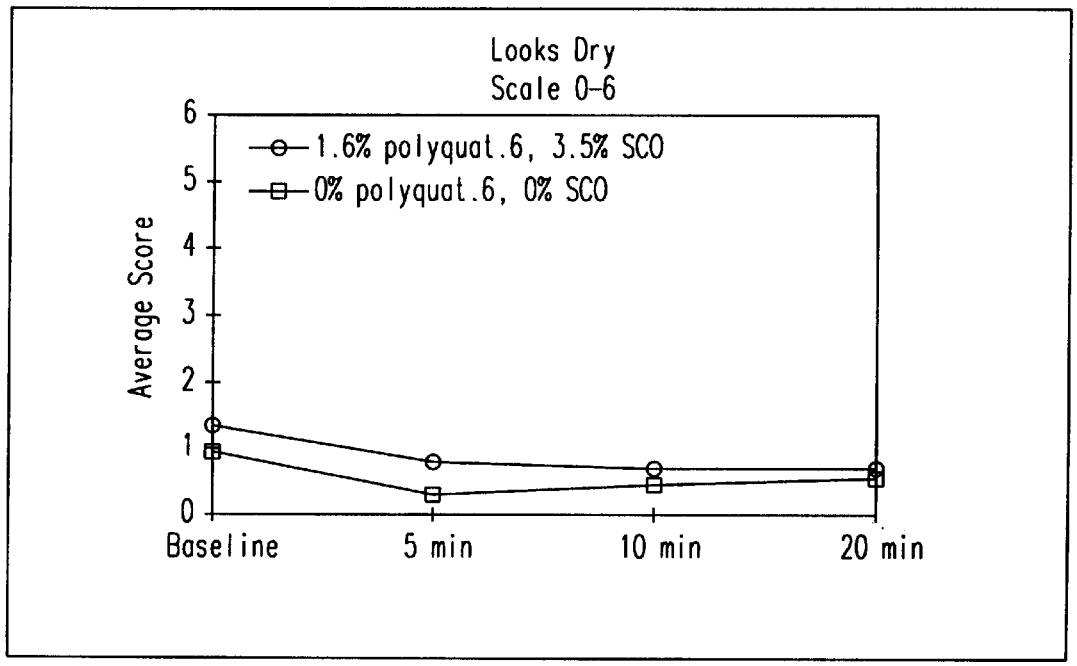
Figure 8H:
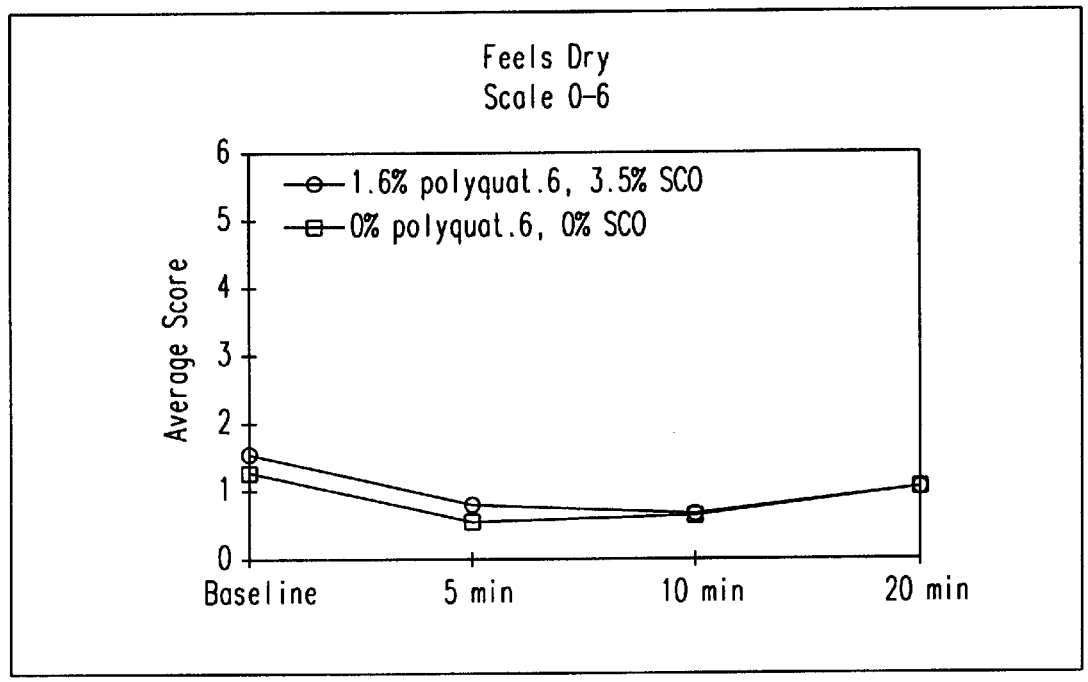
Figure 81:
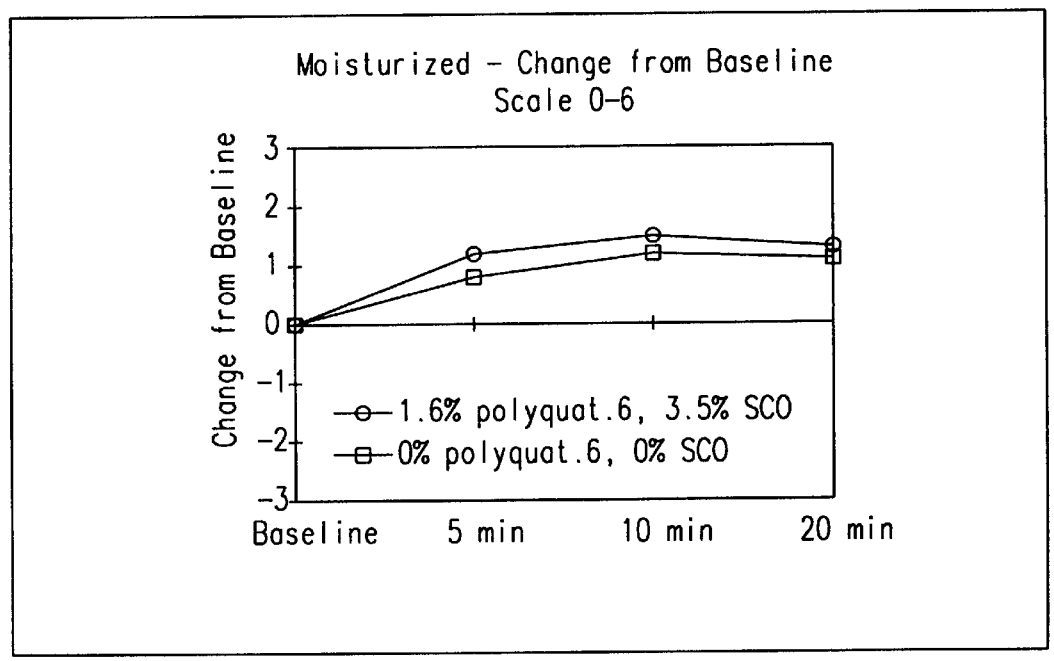
Figure 8J:
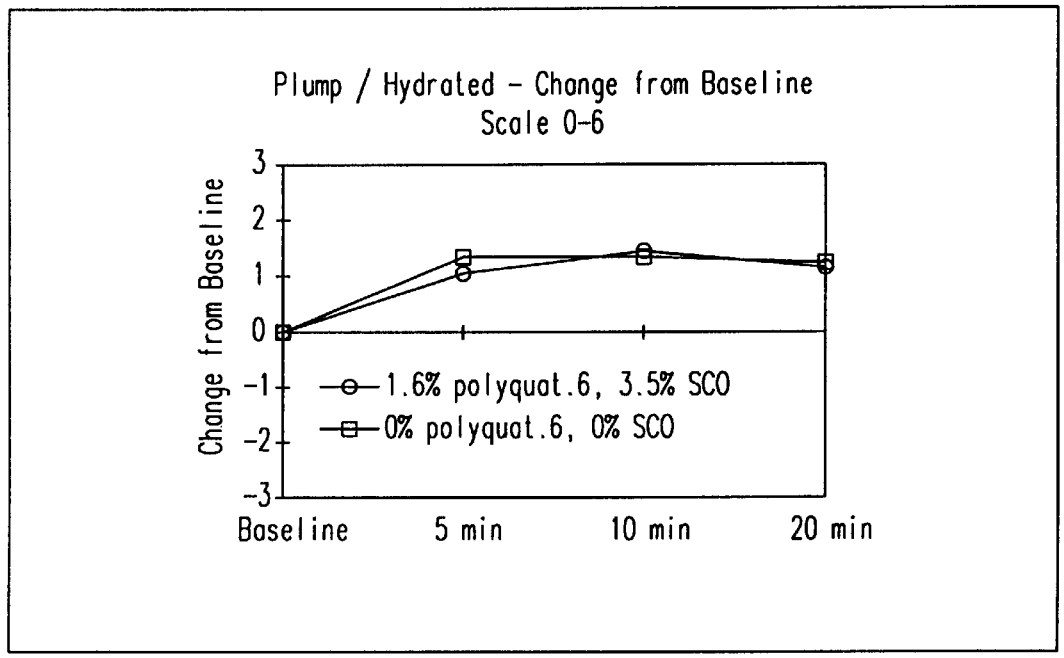
Figure 8K:
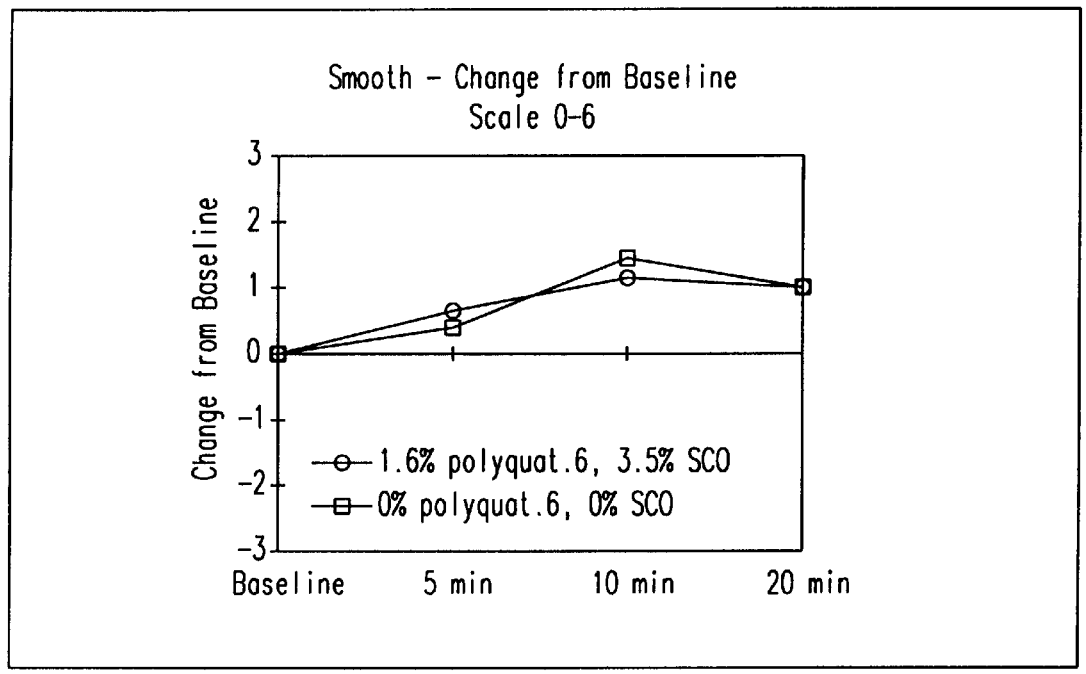
Figure 8L:
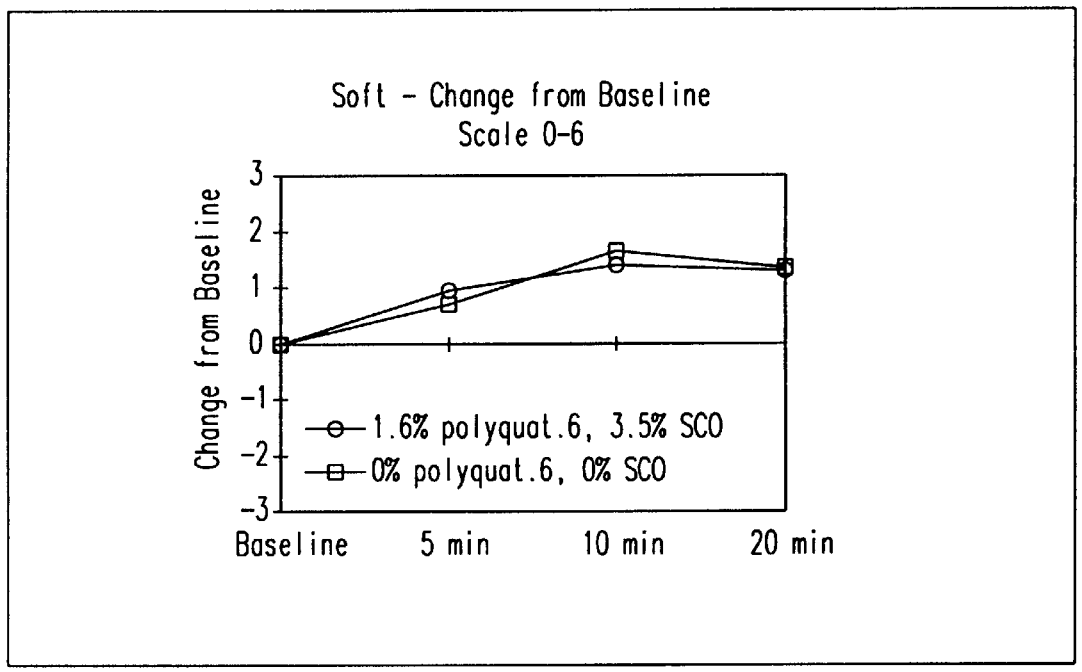
Figure 8M:
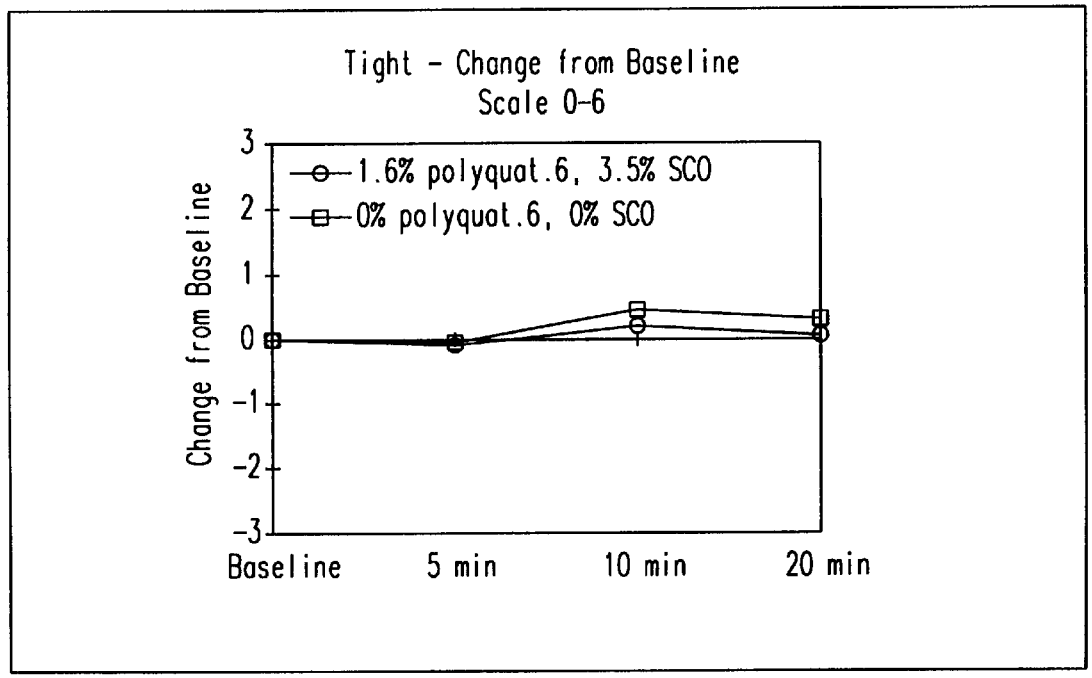
Figure 8N:
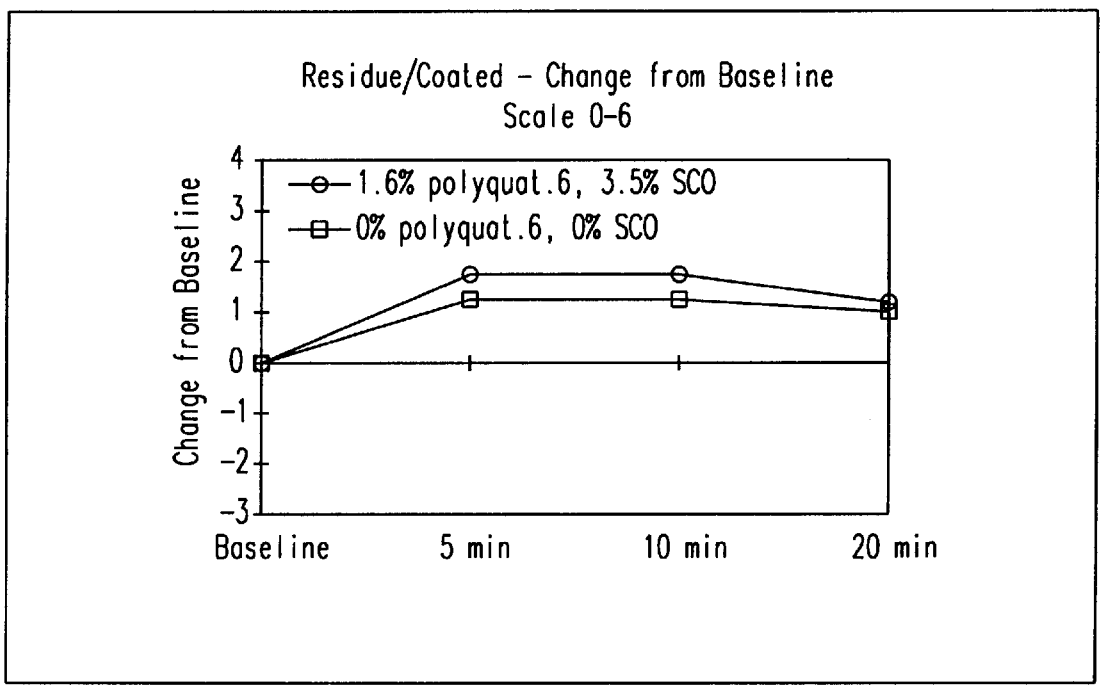
Figure 80:
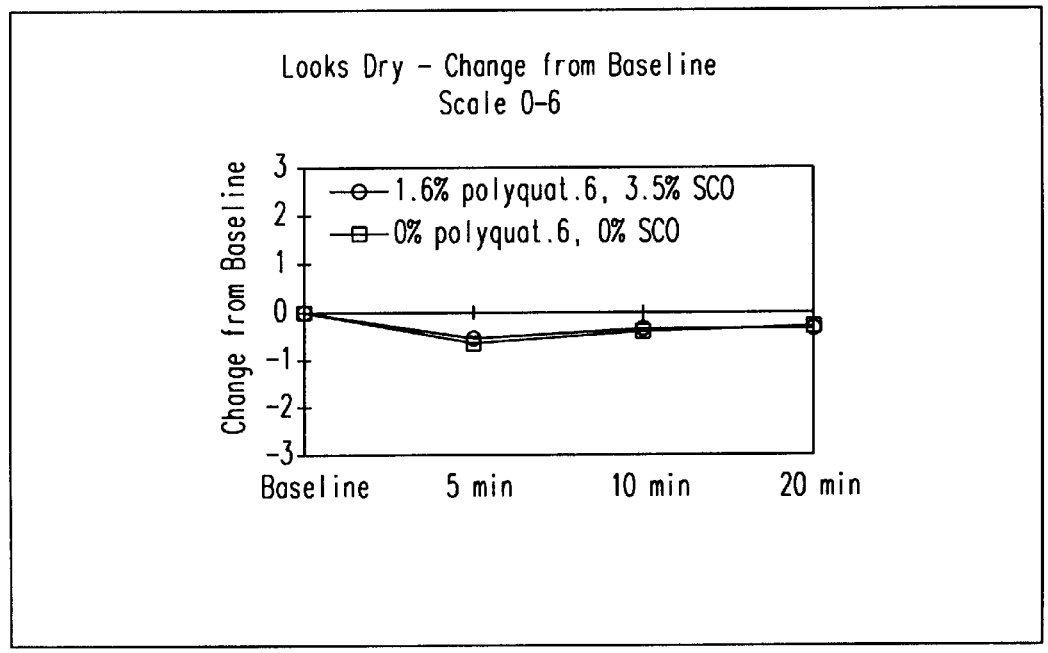
Figure 8P:
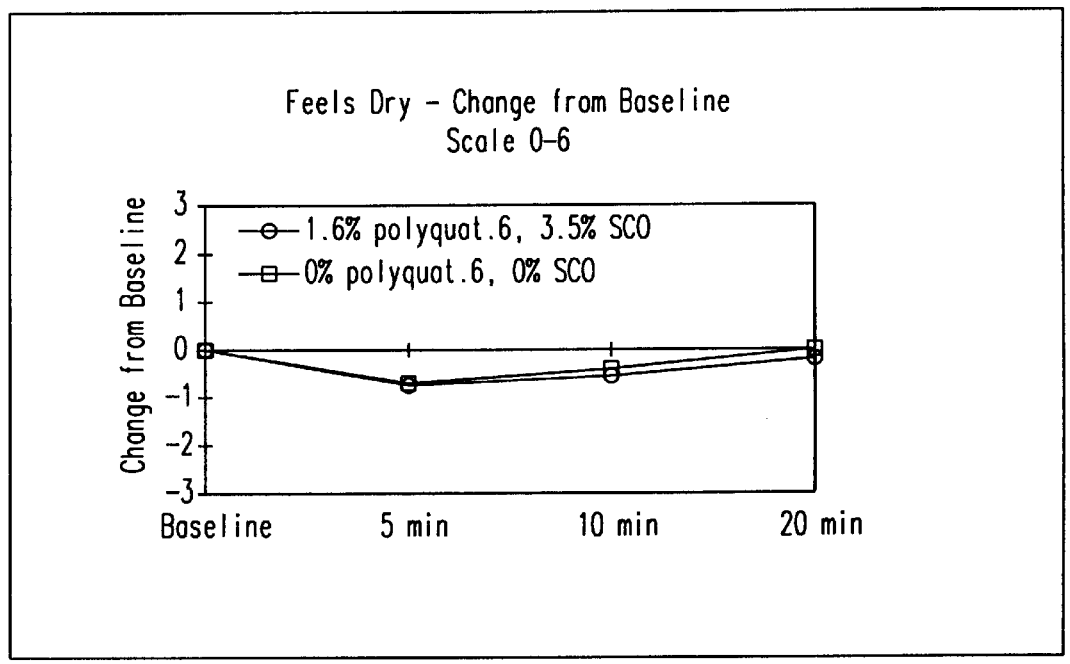

When Polyquaternium 6 (a polymer with a cationic charge that by itself does not deliver a moisturizing feel in a personal care product) or polyethylenimine, a cationic synthetic polymer, is combined with an emollient with an anionic charge such as sulfated castor oil (SCO), an oil with an anionic charge, or dimethicone copolyol phthalate, an anionic silicone, in either a liquid cleanser, cleansing bar, or bath product, a feel is produced that is dramatically more moisturizing than the anionic emollient produces by itself. Different ratios of polyquaternium 6 to anionic emollient have been tested and also show a moisturizing effect. Different levels of the combination of anionic emollient and cationic polymer have also shown a moisturizing effect.

The invention is a composition of a cationic homopolymer, such as dimethyl diallyl ammonium chloride (reference: CAS #26062-79-3/2-propen-1-aminium, N, N-dimethyl-N-2-propenyl-, chloride, homopolymer) and anionic emollients, specifically anionic silicone, anionic triglycerides, anionic oils, such as sulfated castor oil (SCO), dimethylene copolyol phalate (DCP) and mixtures thereof. The mixture of these two oppositely charged materials forms a high viscosity liquid that exhibits limited solubility. The mixture is highly tenacious to skin and similar substrates, and is difficult to remove with normal rinsing/cleansing procedures. Preparations have been made and tested.

Procedure Used for Obtaining Liquid Handwash Data

1. Sample liquid handwash formulas were prepared with polyquaternium 6 and anionic emollients present in different ratios and levels. Total active surfactant levels were maintained as constant. 2. These sample liquid hand wash formulas were subsequently diluted with water to 5% active to make "test solutions". (a typical dilution level for liquid hand wash usage, i.e., when liquid hand wash is used to cleanse hands it is normally mixed with water to be about 5% active).

3. Panelists then treated themselves with these test solutions. (two at a time, one on each arm) and then evaluated skin feel according to the following procedure:

(1) Panelists will answer prewash questionnaire.
(2) Panelists will apply 1.5 ml of wash solution to left forearm and massage for 30 seconds with fingertips of right hand.
(3) Panelists will rinse left arm for 15 seconds.
(4) Panelists will gently pat dry.
(5) Repeat steps 2 thru 4.
(6) Panelists will then apply 1.5 ml of the other wash solution to their right forearm and massage for 30 seconds with the fingertips of the left hand.
(7) Panelists will rinse left arm for 15 seconds.
(8) Panelists will gently pat dry.
(9) Repeat steps 6 thru 8.
(10) The skin feel questionnaire will be completed at 5 minutes, 10 minutes and 20 minutes after the second wash.

Results

1. A liquid handwash that contains 2% active polyquaternium 6 and 4% active sulfated castor oil (SCO) makes panelists feel much more moisturized than they did just before the test. (Baseline as reported on their prewash questionnaire). Handwash containing 2% polyquaternium 6 with 0% SCO made the product less moisturizing than baseline. Handwash containing 0% polyquaternium 6 with 4% SCO gave a moisturizing feel, but to a much lesser degree than the combination.

2. A liquid handwash that contains 2% active polyquaternium 6 and 2% active SCO makes panelists feel just as moisturized as the one which contains 2% active polyquaternium 6 and 4% active SCO. 2% polyquaternium 6 and 1% SCO also delivers a moisturizing feel, but to a lesser degree than 2% polyquaternium 6 and 4% SCO.

3. A liquid handwash that contains 1% active polyquaternium 6 and 1% active SCO also delivers a moisturizing benefit when compared to a handwash with 0% SCO and 0% polyquaternium 6.

4. A liquid handwash that contains 0.5% active polyquaternium 6 and 0.5% active SCO delivered no benefit when compared to a handwash with 0% SCO and 0% polyquaternium 6.

5. A liquid handwash that contains 2% active polyquaternium 6 and 4% active dimethicone copolyol phthalate also delivers a moisturizing benefit when compared to a handwash with 0% SCO and 0% polyquaternium 6.

6. A liquid handwash that contains 2% active polyquaternium 6 and 4% active isopropyl PPG-2-isodeceth-7 carboxylate (CAS #119456-36-9) delivered no benefit when compared to a handwash with 0% SCO and 0% polyquaternium 6.

The Procedure for Obtaining Data on Bath Products

Sample bath bead products were created. One contained 3.5% SCO and 1.6% polyquaternium 6 while the other contained 0% SCO and 0% polyquaternium 6. The product were then diluted to 0.1% volumetrically (typical usage levels for bath beads) in 2L. Panelists were then given the following instructions:

(1) Fill in the prewash questionnaire.
(2) Immerse appropriate hand in appropriate solution and move slowly for 2 minutes.
(3) Pat dry.
(4) Evaluate hands at 5, 10, and 20 minutes.

Results

The product containing 1.6% active polyquaternium 6 and 3.5% active SCO was shown to be more moisturizing than the formula with 0 polyquaternium 6 and 0 SCO.

Sample hand wash formulas and both bead formulas tested are set forth in Tables 1–5. A sample bar soap formula tested and demonstrated to show similar results is set forth in Table 6.

Shampoo Products

The inventive composition also finds utility as a superior "2-in-1" (cleansing and conditioning) shampoo. Typical shampoo formulations provide a cleansing action. Certain shampoos also contain conditioning agents, to avoid the repetitive process of first applying, lathering, and rinsing the shampoo, following by application and rinsing of the conditioner. The shampoos may be solutions, or emulsions. The complex formed by the cationic polymer and anionic emollient of the claimed invention provide excellent conditioning properties. Because of the charged nature of the complex, this complex deposits preferentially on the hair, ensuring a high degree of conditioning contact and efficacy. A sample conditioning shampoo formula is set forth in Table 7.

In a conditioning shampoo formulation, the cationic polymer and anionic emollient will be combined with an amount of a non-ionic or Zwitterionic surfactant effective to provide a cleansing effect. The complex formed is an effective conditioner. The surfactant is typically present in about 7.5–30%. The remaining optional ingredients are presents in amounts from 0–15% by weight.

TABLE 1

Sensory Evaluation of Complex Versus Componenets
Sample Handwash Formulas

| | polyquat 6 plus SCO | | polyquat. 6 only | | SCO only | |
|---|---|---|---|---|---|---|
| | Raw Material (w/w %) | Material % active | Raw Material (w/w %) | Material % active | Raw Material (w/w %) | Material % active |
| DI Water | 43.98 | | 49.7 | | 48.98 | |
| Cocamidopropyl betaine | 45 | 13.5 | 45 | 13.5 | 45 | 13.5 |
| Decyl polyglucose | | 0.0 | | 0.0 | | 0.0 |
| Polyquaternium 6 | 5 | 2.0 | 5 | 2.0 | | 0.0 |
| Sulfated castor oil | 5.72 | 4.0 | | 0.0 | 5.72 | 4.0 |

TABLE 1-continued

Sensory Evaluation of Complex Versus Componenets
Sample Handwash Formulas

| | polyquat. 6 plus SCO | | polyquat. 6 only | | SCO only | |
|---|---|---|---|---|---|---|
| | Raw Material (w/w %) | Material % active | Raw Material (w/w %) | Material % active | Raw Material (w/w %) | Material % active |
| Dimethicone copolyol phthalate | | 0.0 | | 0.0 | | 0.0 |
| DMDM hydantoin | 0.3 | 0.1 | 0.3 | | 0.3 | |
| Total active content | | 19.6 | | 15.5 | | 17.5 |
| Percent present in test solution (test solution is sample hand wash solution diluted to 5% active with DI water) | | 25.5 | | 32.3 | | 28.6 |

TABLE 2

Sensory Evaluation of Complex in Differing Ratios
Sample Handwash Formulas

| | 2% poltquat. 6, 4% SCO | | 2% polytquat. 6, 2% SCO | | 2% poltquat. 6, 1% SCO | |
|---|---|---|---|---|---|---|
| | Raw Material (w/w %) | Material % active | Raw Material (w/w %) | Material % active | Raw Material (w/w %) | Material % active |
| DI Water | 43.98 | | 46.84 | | 53.27 | |
| Cocamidopropyl betaine | 45 | 13.5 | 45 | 13.5 | 45 | 13.5 |
| Decyl polyglucose | | 0.0 | | 0.0 | | 0.0 |
| Polyquaternium 6 | 5 | 2.0 | 5 | 2.0 | | 0.0 |
| Sulfated castor oil | 5.72 | 4.0 | 2.86 | 2.0 | 1.43 | 1.0 |
| Dimethicone copolyol phthalate | | 0.0 | | 0.0 | | 0.0 |
| DMDM hydantoin | 0.3 | 0.1 | 0.3 | 0.1 | 0.3 | 0.1 |
| Total active content | | 19.6 | | 17.6 | | 14.6 |
| Percent present in test solution (test solution is sample hand wash solution diluted to 5% active with DI water) | | 25.5 | | 28.4 | | 34.2 |

TABLE 3

Sensory Evaluation of Complex Made with
anionic silicone
(dimethicone copolyol phthalate)
Sample Handwash Formulas

| | 4% amiomic silicone 2% polyquat. 6 | | 0% amiomic silicone 0% polyquat. 6 | |
|---|---|---|---|---|
| | Raw Material (w/w %) | Material % active | Raw Material (w/w %) | Material % active |
| DI Water | 63.7 | | 72.7 | |
| Cocamidopropyl betaine | 0 | 0.0 | 0 | 0.0 |
| Decyl polyglucose | 27 | 13.5 | 27 | 13.5 |
| Polyquaternium 6 | 5 | 2.0 | 0 | 0.0 |
| Sulfated castor oil | 0 | 0.0 | 0 | 0.0 |
| Dimethicone copolyol phthalate | 4 | 4.0 | | 0.0 |
| DMDM hydantoin | 0.3 | 0.1 | 0.3 | 0.1 |
| Total active content | | 19.6 | | 13.6 |

TABLE 3-continued

Sensory Evaluation of Complex Made with
anionic silicone
(dimethicone copolyol phthalate)
Sample Handwash Formulas

|  | 4% amiomic silicone 2% polyquat. 6 | | 0% amiomic silicone 0% polyquat. 6 | |
|---|---|---|---|---|
|  | Raw Material (w/w %) | Material % active | Raw Material (w/w %) | Material % active |
| Percent present in test solution (test solution is sample hand wash solution diluted to 5% active with DI water) |  | 25.5 |  | 36.7 |

TABLE 4

Sensory Evaluation of Complex Made with
anionic ester
(isopropyl PPG-2-isodeceth-7 carboxylate)
Sample Handwash Formulas

|  | 2% polyquat. 6 4% amiomic ester | | 0% polyquat. 6 0% amiomic ester | |
|---|---|---|---|---|
|  | Raw Material (w/w %) | Material % active | Raw Material (w/w %) | Material % active |
| DI Water | 45.7 |  | 54.7 |  |
| Cocamidopropyl betaine | 45 | 13.5 | 45 | 13.5 |
| Decyl polyglucose | 0 | 0.0 | 0 | 0.0 |
| Polyquaternium 6 | 5 | 2.0 | 0 | 0.0 |
| Sulfated castor oil | 0 | 0.0 | 0 | 0.0 |
| Isopropyl PPG-2-Isodeceth-7 Carboxylate phthalate | 4 | 4.0 |  | 0.0 |
| DMDM hydantoin | 0.3 | 0.1 | 0.3 | 0.1 |
| Total active content |  | 19.6 |  | 13.6 |
| Percent present in test solution (test solution is sample hand wash solution diluted to 5% active with DI water) |  | 25.5 |  | 36.7 |

TABLE 5

Bath Beads

| Part | Code | Ingredient | Percent | Wt (g) | Cost/lb. | Form cost |
|---|---|---|---|---|---|---|
|  |  | STP (Monsanto) | 12.00 | 120.00 | 0.44 | 0.0528 |
|  | Witco | Alpa Olefin Sulfonate (Witconate AOK) | 6.00 | 60.00 | 0.66 | 0.0518 |
|  | 9744-00-020 | Sulfated Castor Oil | 5.00 | 50.00 | 1.08 | 0.054 |
|  | 9743-00-020 | Polyquatemium-6 | 4.00 | 40.00 | 2.20 | 0.88 |
|  | 1394-00-020 | Cherry Almond | 0.00 | 0.00 | 6.00 | 0 |
|  | 9728-00-020 | Sodium Laureth Sulfate (70%) | 2.00 | 20.00 | 0.61 | 0.0122 |
|  | 9543-00-020 | Sodium Chloride | 71.00 | 710.00 | 0.09 | 0.0639 |
|  |  |  | 100.00 | 1000.00 |  | 0.3225 |

TABLE 6

EXAMPLE BAR SOAP FORMULA

| Raw Material Description | W/W % | Material % Active |
|---|---|---|
| Soap | 87.88 | 75.43 |
| Glycerin | | 0.58 |
| Sodium Chloride | | 0.62 |
| Sodium Citrate | | 0.20 |
| Tetrasodium EDTA | | 0.10 |
| PEG-150 Pentaerythrityl Tetrastearate | | 1.00 |
| Fatty Acid (Superfat) | | 6.00 |
| Sulfated Castor Oil | 1.00 | 0.70 |
| Polyquaternium-6 | 2.00 | 0.80 |
| Titanium Dioxide | | 0.50 |
| Etidronic Acid | | 0.02 |
| BHT | | 0.20 |
| Water remaining W/W % | | Balance |

TABLE 7

SAMPLE CONDITIONING SHAMPOO FORMULA

| Raw Material Description | Raw Material (w/w %) | Material Active % |
|---|---|---|
| DI Water | balance | balance |
| Cocamidopropyl Betaine | 45 | 13.5 |
| Laureth 4 | 4 | 4 |
| Polyquaternium 6 | 5 | 2 |
| Dimethicone Copolyol Pthalate | 4 | 4 |
| Fragrance | 0.3 | 0.3 |
| DMDM Hydantoin | 0.3 | 0.3 |

Optional Components

While the full method of effective deposition achieved by this invention has not been elucidated, other than empirically, it is believed that maintenance of sparing solubility in the solution preparation is a prerequisite to effective and tenacious emollient deposition. To that end, this composition does not admit of the inclusion of cationic surfactants other than the cationic polymers identified (polyquat 6, PEI) nor does the addition of cationic emollients improve results. Other neutral emollients, such as petrolatum, non-anionic silicones and the like may be added, in amounts up to 25%. Colorants/pigments, fragrances and the like, as well as preservatives and stabilizers are well known to those of skill in the art and are not further exemplified herein. Selection of the preferred embodiments set forth above generally give a pH of about 7–8. The addition of pH modifiers such as citric acid, lactic acid or salts thereof, may be employed, when necessary, to maintain an appropriate pH.

Surfactants may be present in the composition. While anionic surfactants are inappropriate, non-ionic surfactants, such as alcohol ethers (e.g., laureth-3, steareth-6), fatty acid alkanolamides, (e.g., cocamide DEA, lauramide MIPA), amine oxides (e.g., lauramine oxide, cocamidopropyl amine oxide), sorbitan esters (e.g., sorbitan laurate, sorbitan oleate, sorbitan palpitate) and alkyl polyglucosides (e.g., decyl polyglucose, lauryl polyglucose) may be used in addition, where the formula preparation requires additional surfactant presence. Typically, such surfactants are included for their cleansing abilities. Zwitterionic surfactants such as betaines (e.g., cocamidopropyl betaine) sultaines (e.g., cocamidopropyl hydroxysultaine) may be used. Zwitterionic surfactants are typically used to improve the properties addressed by the cationic/anionic complex of the invention, specifically, properties involved in skin feel and appearance. These optional surfactants may be present in amounts up to 40%.

Formulations are prepared by straight mixing of the components. Prior to the addition of pigments and colorants, the active ingredients, in water, give a clear solution, which precipitates on dilution.

In general, the cationic polymer is present in amounts of 0.5–10%, with a preferred range being 2–5%, while the anionic emollient is present in an amount of 1–30%, with a preferred range being 2–10%. Additional surfactants, optional ingredients identified above, and others, may be present in amounts up to a total of 40%. The balance, for liquid preparations, is water. Soap preparations typically include the active ingredients, such as polyquat 6 and SCO, in amounts up to 15%, based on conventional soap-based bar compositions.

The inventive compositions has been described in terms of specific example, as well as generic description. The addition of other optional elements, and alterations of non-critical percentages, to give equivalent results, remain within the ability of those of ordinary skill in the art without the exercise of inventive faculty. The invention is not so limited, save as recited in the claims set forth below.

What is claimed is:

1. A personal cleansing formulation, comprising:
   0.5–10%, by active weight, of a cationic polymer selected from the group consisting of polyquaternium 6 (polyquat 6), polyethylene imine (PEI) and mixtures thereof,
   1%–30% by active weight of an anionic emollient selected from the group consisting of sulfated castor oil (SCO), dimethicone copolyol phthalate (DCP) and mixtures thereof,
   0–40% of at least one component selected from the group consisting of a pigment, a fragrance, a preservative, a non-ionic surfactant, a Zwitterionic surfactant and a non-ionic emollient, and the balance water,
   wherein said composition, when applied to the skin followed by rinsing, acts as at least one of a skin moisturizer, skin hydration agent, skin smoother or skin softener.

2. The composition of claim 1, wherein said Zwitterionic surfactant is cocamidopropyl betaine.

3. The composition of claim 1, wherein said cationic polymer is present in an amount of 2–6%, by weight, and said anionic emollient is present in an amount of 1–10%, by weight.

4. The composition of claim 1, wherein said composition is in the form of a lotion.

5. The composition of claim 1, wherein said composition is the in the form of a soap bar.

6. A method of effecting of at least one of skin moisturizing, skin hydrating, skin smoothing and skin softening while washing, comprising applying the formulation of claim 1 to said skin, and subsequently rinsing said skin and allowing said skin to dry.

7. A conditioning shampoo formulation, comprising:
   0.5–10%, by active weight, of a cationic polymer selected from the group consisting of polyquat 6, PEI and mixtures thereof,
   1%–30% by active weight of anionic emollient selected from the group consisting of SCD, DCP and mixtures thereof
   at least one non-ionic or Zwitterionic surfactant present in amounts sufficient to provide a shampoo cleansing action, 0–15% of at least one component selected from the group consisting of a pigment, a fragrance and a preservative, and the balance water.

8. The shampoo formulation of claim 7, wherein said surfactant is a Zwitterionic surfactant, and comprises cocamidopropyl betaine.

9. The shampoo formulation of claim 7, wherein said cationic polymer is present in an amount of 2–6%, by weight, and said anionic emollient is present in an amount of 1–10%, by weight.

10. A method of cleaning and conditioning hair, comprising applying the shampoo formulation of claim 7 to said hair, causing said formulation to lather, and rinsing said lathered formulation from said hair.

* * * * *